US008715947B2

(12) United States Patent
Stern et al.

(10) Patent No.: US 8,715,947 B2
(45) Date of Patent: May 6, 2014

(54) INHIBITION OF THE INTERACTION BETWEEN 5T4 ONCOFOETAL GLYCOPROTEINS AND CXC CHEMOKINE RECEPTORS AS A METHOD OF IDENTIFYING CHEMOTAXIS INHIBITORS

(75) Inventors: Peter L. Stern, Manchester (GB); Vaskar Saha, Manchester (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 13/502,893

(22) PCT Filed: Oct. 20, 2010

(86) PCT No.: PCT/GB2010/001940
§ 371 (c)(1), (2), (4) Date: Jun. 29, 2012

(87) PCT Pub. No.: WO2011/048369
PCT Pub. Date: Apr. 28, 2011

(65) Prior Publication Data

US 2012/0282183 A1 Nov. 8, 2012

(30) Foreign Application Priority Data

Oct. 20, 2009 (GB) .................................. 0918383.1

(51) Int. Cl.
*G01N 33/567* (2006.01)
*G01N 33/574* (2006.01)

(52) U.S. Cl.
USPC ........................................ 435/7.21; 435/7.23

(58) Field of Classification Search
None
See application file for complete search history.

(56) References Cited

FOREIGN PATENT DOCUMENTS

WO 2007/106744 A2 9/2007

OTHER PUBLICATIONS

Southgate, Thomas D. et al., "CXCR4 Mediated Chemotaxis is Regulated by 5T4 Oncofetal Glycoprotein in Mouse Embryonic Cells", PLoS One, 5(4): 1-20 (2010).

Aslanian, A. et al., "Targeted Disruption of the Scavenger Receptor and Chemokine CXCL16 Accelerates Atherosclerosis", Circulation, 114(6): 583-90 (2006).

Awan, A. et al., "514 Interacts with TIP-2/GIPC, a PDZ Protein, with Implications for Metastasis", Biochem. Biophys. Res. Commun., 290: 1030-1036 (2002).

Balkwill, F. et al., "The significance of cancer cell expression of the chemokine receptor CXCR4", Cancer Biology, 14: 171-179 (2004).

Barbieri, F. et al., "Overexpression of Stromal Cell—Derived Factor 1 and Its Receptor CXCR4 Induces Autocrine/Paracrine Cell Proliferation in Human Pituitary Adenomas", Clin. Cancer Res., 14(16): 5022-32 (2008).

Bradstock, K.F. et al., "Effects of the chemokine stromal cell-derived factor-1 on the migration and localization of precursor-B acute lymphoblastic leukemia cells within bone marrow stromal layers", Leukemia, 14: 882-888 (2000).

Burger, J. et al., "CXCR4: a key receptor in the crosstalk between tumor cells and their microenvironment", Blood, 107(5): 1761-1767 (2006).

Burns, J.M. et al., "A novel chemokine receptor for SDF-1 and I-TAC involved in cell survival, cell adhesion, and tumor development", JEM, 203(9): 2201-2213 (2006).

Carsberg, C. et al., "Metastasis-associated 5T4 oncofoetal antigen is concentrated at microvillus projections of the plasma membrane", J. Cell Science, 108: 2905-2916 (1995).

Carsberg, C. et al., "Metastasis-Associated 5T4 Antigen Disrupts Cell-Cell Contacts and Induces Cellular Motility in Epithelial Cells", Int. J. Cancer, 68: 84-92 (1996).

Cavallaro, U. et al., "Cell Adhesion and Signalling by Cadherins and IG-Cams in Cancer", Nature, 4: 118-132 (2004).

Christopherson, K.W. et al., "Modulation of Hematopoietic Stem Cell Homing and Engraftment by CD26", Science, 305: 1000-1003 (2004).

Devries, M.E. et al., "Defining the Origins and Evolution of the Chemokine/Chemokine Receptor System", J. Immunol., 176: 401-415 (2006).

Eastham, A.M. et al., "Epithelial-MesenchymalTransition Events during Human Embryonic Stem Cell Differentiation", Cancer Res., 67(23): 11254-11262 (2007).

Forsberg, G. et al., "Therapy of human non-small-cell lung carcinoma using antibody targeting of a modified superantigen", British Journal of Cancer, 85(1): 129-136 (2001).

Ganju, R.K. et al., "The α-Chemokine, Stromal Cell-derived Factor-1α, Binds to the Transmembrane G-protein-coupled CXCR-4 Receptor and Activated Multiple Signal Transduction Pathways", J. Biol. Chem., 273(36): 23169-23175 (1996).

Griffiths, R.W. et al., "Expression of the 5T4 oncofoetal antigen in renal cell carcinoma: a potential target for T-cell-based immunotherapy", British Journal of Cancer, 93: 670-677 (2005).

Guarino, M. et al., "Epithelial-mesenchymal transition and tumour invasion", Int. J. Biochem. & Cell Biol., 39: 2153-2160 (2007).

Hardy, S. et al., "Construction of Adenovirus Vectors through Cre-Iox Recombination", J. Virol., 71(3): 1842-1849 (1997).

Hernandez-Lopez, C. et al., "CXCL12/CXCR4 signaling promotes human thymic dendritic cell survival regulating the Bc1-2/Bax ratio", Immunology Letters, 120: 72-78 (2008).

Heydtmann, M. et al., "CXC Chemokine Ligand 16 Promotes Integrin-Mediated Adhesion of Liver-Infiltrating Lymphocytes to Cholangiocytes and Hepatocytes within the Inflamed Human Liver", J. Immunol., 174: 1055-1062 (2005).

(Continued)

*Primary Examiner* — Robert Landsman

(74) *Attorney, Agent, or Firm* — Patrick J. Hagan; Dann, Doreman, Herrell and Skillman

(57) ABSTRACT

Methods and agents are disclosed based on the finding that 5T4 interacts with CXCR4 in the cell membrane to form a complex, and that the 5T4 transmembrane region is involved in the promotion of CXCR4 membrane expression and chemotactic response.

15 Claims, 32 Drawing Sheets

(56) References Cited

OTHER PUBLICATIONS

Hildinger, M. et al., "FMEV vectors: both retroviral long terminal repeat and leader are important for high expression in transduced hematopoietic cells", Gene Therapy, 5: 1575-1579 (1998).
Hole, N. et al., "A 72 kD trophoblast glycoprotein defined by a monoclonal antibody", Br. J. Cancer, 57: 239-46 (1988).
Hooper, M. et al., "HPRT-deficient (Lesch-Nyhan) mouse embryos derived from germline colonization by cultured cells", Nature, 326: 292-295 (1987).
Hu, J.S. et al., "AMD3465, a Novel CXCR4 Receptor Antagonist, Abrogated Schistosomal Antigen-elicited (Type-2) Pulmonary Granuloma Formation", Amer. J. Path., 169(2): 424-432 (2006).
Hu, W. et al., "CXCR6 is expressed in human prostate cancer in vivo and is involved in the in vitro invasion of PC3 and LNCap cells", Cancer Sci., 99(7): 1362-1369 (2008).
Juremalm, M. et al., "The chemokine receptor CXCR4 is expressed within the mast cell lineage and its ligand stromal cell-derived factor-1α acts as a mast cell chemotaxin", Eur. J. Immunol., 30: 3614-3622 (2000).
King, K.W. et al., "Organisation of the mouse and human 5T4 oncofoetal leucine-rich glycoprotein genes and expression in foetal and adult murine tissues", Biochimica et Biophysica Acta, 1445: 257-270 (1999).
Kobe, B. et al., "The leucine-rich repeat as a protein recognition motif", Current Opinion in Structural Biology, 11: 725-732 (2001).
Li, M. - M et al "Multiple roles of chemokine CXCL12 in the central nervous system: A migration from immunology to neurobiology", Progress in Neurobiology, 84: 116-131 (2008).
Lukacs, N. et al., "AMD3100, a CxCR4 Antagonist, Attenuates Allergic Lung Inflammation and Airway Hyperreactivity", Amer. J. Pathol., 160(4): 1353-1360 (2002).
Ma, Q. et al., "Impaired B-lymphopoiesis, myelopoiesis, and derailed cerebellar neuron migration in CXCR4- and SDS-1-deficient mice", Proc. Natl. Acad. Sci., 95: 9448-9453 (1998).
Mieke, W. et al., "Low Intercellular Adhesion Molecule 1 and High 5T4 Expression on Tumor Cells Correlate with Reduced Disease-free Survival in Colorectal Carcinoma Patients", Clinical Cancer Res., 3: 1923-1930 (1997).
Mikami, S. et al., "Blockade of CXCL12/CXCR4 Axis Ameliorates Murine Experimental Colitis", J. Pharmacol. Exper. Therap., 327(2): 383-392 (2008).
Myers, K.A. et al., "Isolation of a cDNA Encoding 5T4 Oncofetal Trophoblast Glycoprotein", J. Biol. Chem., 269(12): 9319-9324 (1994).
Nagasawa, T. et al., "Defects of B-cell lymphopoiesis and bone-marrow myelopoiesis in mice lacking the CXC chemokine PBSF/SDF-1", Nature, 382: 635-638 (1996).
Nanki, T. et al., "Pathogenic Role of the CXCL16-CXCR6 Pathway in Rheumatoid Arthritis", Arthritis & Rheumatism, 52(10): 3004-3014 (2005).
Naor, D. et al., "Involvement of CD44, a molecule with a thousand faces, in cancer dissemination", Seminars in Cancer Biol., 18: 260-267 (2008).
Orimo, A. et al., "Stromal Fibroblasts Present in Invasive Human Breast Carcinomas Promote Tumor Growth and Angiogenesis through Elevated SDF-1/CXCL12 Secretion", Cell, 121: 335-348 (2008).
Pello, O.M. et al., "Ligand stabilization of CXCR4/delta-opioid receptor heterodimers reveals a mechanism for immune response regulation", Eur. J. Immunol., 38: 537-549 (2008).
Shaw, D.M. et al., "A phase II study of a 5T4 oncofoetal antigen tumour-targeted superantigen (ABR-214936) therapy in patients with advanced renal cell carcinoma", British Journal of Cancer, 96: 567-574 (2007).
Sipkins, D.A. et al., "In vivo imaging of specialized bone marrow endothelial microdomains for tumour engraftment", Nature: 435: 969-973 (2005).
Southall, P.J. et al. "Immunohistological distribution of 5T4 antigen in normal and malignant tissues", Br. J. Cancer, 61: 89-95 (1990).
Southgate, T. et al., "Gene Transfer into Neural Cells in Vitro Using Adenoviral Vectors", Curr. Protoc. Neurosci., Chapter 4, Unit 4.23 (2001).
Spencer, H.L. et al., "E-Cadherin Inhibits Cell Surface Localization of the Pro-Migratory 5T4 Oncofetal Antigen in Mouse Embryonic Stem Cells", Molecular Biology of the Cell, 18: 2838-2851 (2007).
Starzynska, T. et al., "Prognostic significance of 5T4 oncofetal antigen expression in colorectal carcinoma", Br. J. Cancer, 69: 899-902 (1994).
Starzynska, T. et al., "5T4 oncofetal antigen in gastric carcinoma and its clinical significance", Eur. J. Gastroenterol. Hepatol., 10: 479-484 (1998).
Strader, C. et al., "The family of G-protein-coupled receptors", FASEB J., 9: 745-754 (1995).
Strefford, J.C. et al., "Complex genomic alterations and gene expression in acute lymphoblastic leukemia with intrachromosomal amplification of chromosome 21", PNAS, 103(21): 8167-8172 (2006).
Thelen, M. et al., "CXCR7, CXCR4 and CXCL12: An eccentric trio?", J. Neuroimmunol., 198: 9-13 (2008).
Tian, S. et al., "Distinct Functional Sites for Human Immunodeficiency Virus Type 1 and Stromal Cell-Derived Factor 1α on CXCR4 Transmembrane Helical Domains", J. Virol., 79(20): 12667-12673 (2005).
van Delft, F.W. et al., "Prospective gene expression analysis accurately subtypes acute leukaemia in children and establishes a commonality between hyperdiploidy and t(12;21) in acute lymphoblastic leukaemia", British Journal of Haematology, 130: 26-35 (2005).
Vandercappellen, J. et al., "The role of CXC chemokines and their receptors in cancer", Cancer Letters, 267: 226-44 (2008).
Ward, C.M. et al., "The 5T4 oncofoetal antigen is an early differentiation marker of mouse ES cells and its absence is a useful menas to assess pluripotency"', J. Cell Sci., 116: 4533-4542 (2003).
Ward, C.M. et al., "Cell surface 5T4 antigen is transiently upregulated during early human embryonic stem cell differentiation: Effect of 5T4 phenotype on neural lineage formation", Exp. Cell Res., 312: 1713-26 (2006).
Woods, A.M. et al., "Characterization of the murine 5T4 oncofoetal antigen: a target for immunotherapy in cancer", Biochem. J., 366: 353-365 (2002).
Wragg, A. et al., "VEGFR1/CXCR4-positive progenitor cells modulate local inflammation and augment tissue perfusion by a SDF-1-dependent mechanism", J. Mol. Med., 86: 1221-1232 (2008).
Wrigley, E. et al., "5T4 oncofetal antigen expression in ovarian carcinoma", Int. J. Gynecol. Cancer, 5: 269-274 (1995).
Wu, M. et al., "LRRC4 Inhibits Human Glioblastoma Cells Proliferation, Invasion, and proMMP-2 Activation by Reducing SDF-1alpha/CXCR4-Mediated ERK1/2 and Akt Signaling Pathways", J. Cell. Biochem., 103: 245-255 (2008).
Xu, J., "Preparation, Culture, and Immortalization of Mouse Embryonic Fibroblasts", Curr. Protoc. Mol. Biol., Chapter 28, Unit 28 1 (2005).
Xu, Y. et al., "Evaluation of "Credit Card" Libraries for Inhibition of HIV-1 gp41 Fusogenic Core Formation", J. Comb. Chem., 8: 531-539 (2006).
Zhang, L. et al., "Tissue Microenvironment Modulates CXCR4 Expression and Tumor Metastasis in Neuroblastoma", Neoplasia, 9(1): 36-46 (2007).
Zou, Y-R. et al., "Function of the chemokine receptor CXCR4 in haematopoiesis and in cerebellar development", Nature, 393: 595-599 (1998).

A
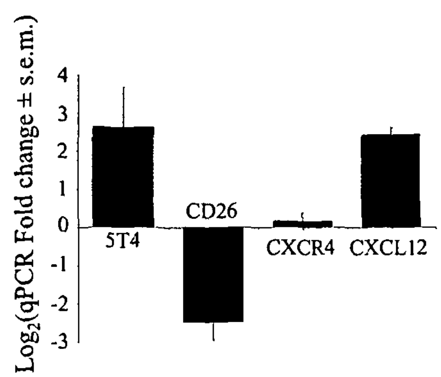
B
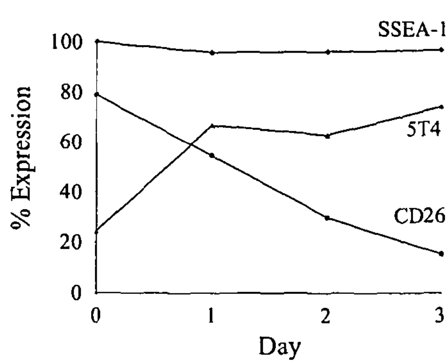
C
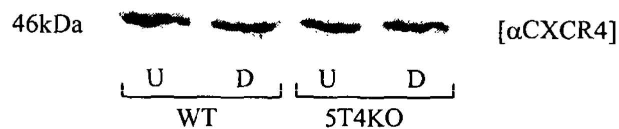
D
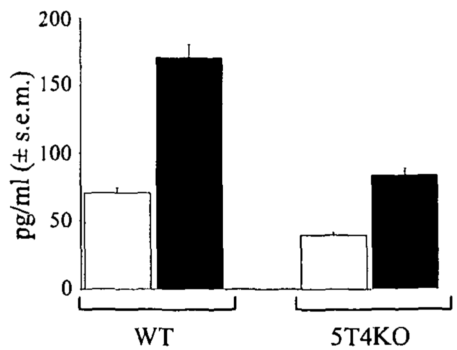
Figure 1A

A
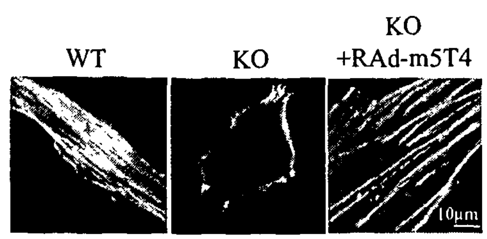
B
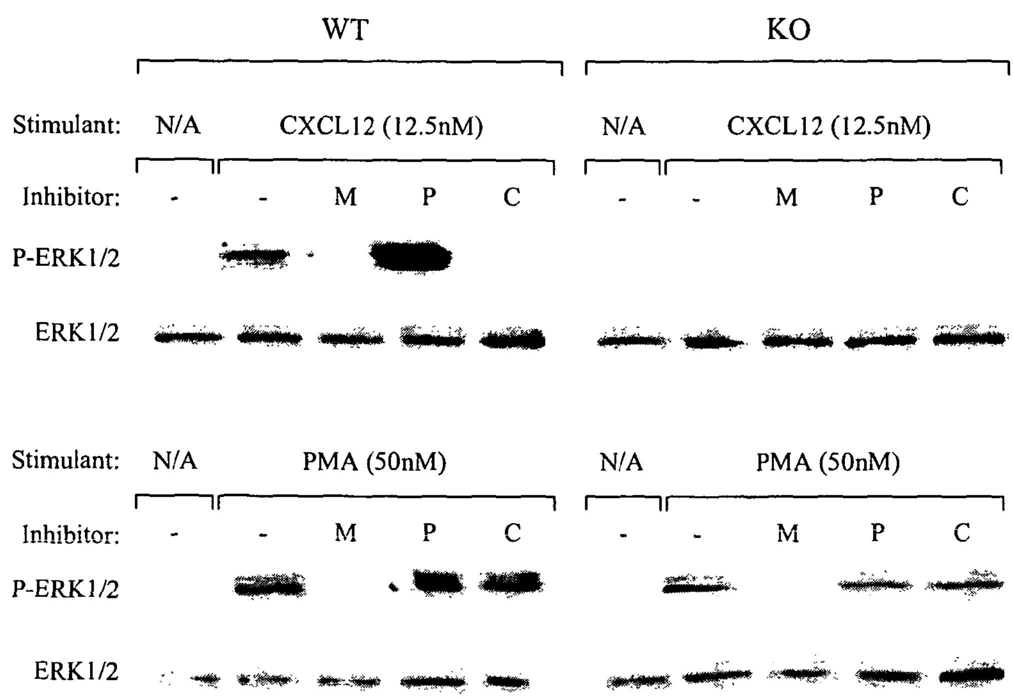
Figure 5

A
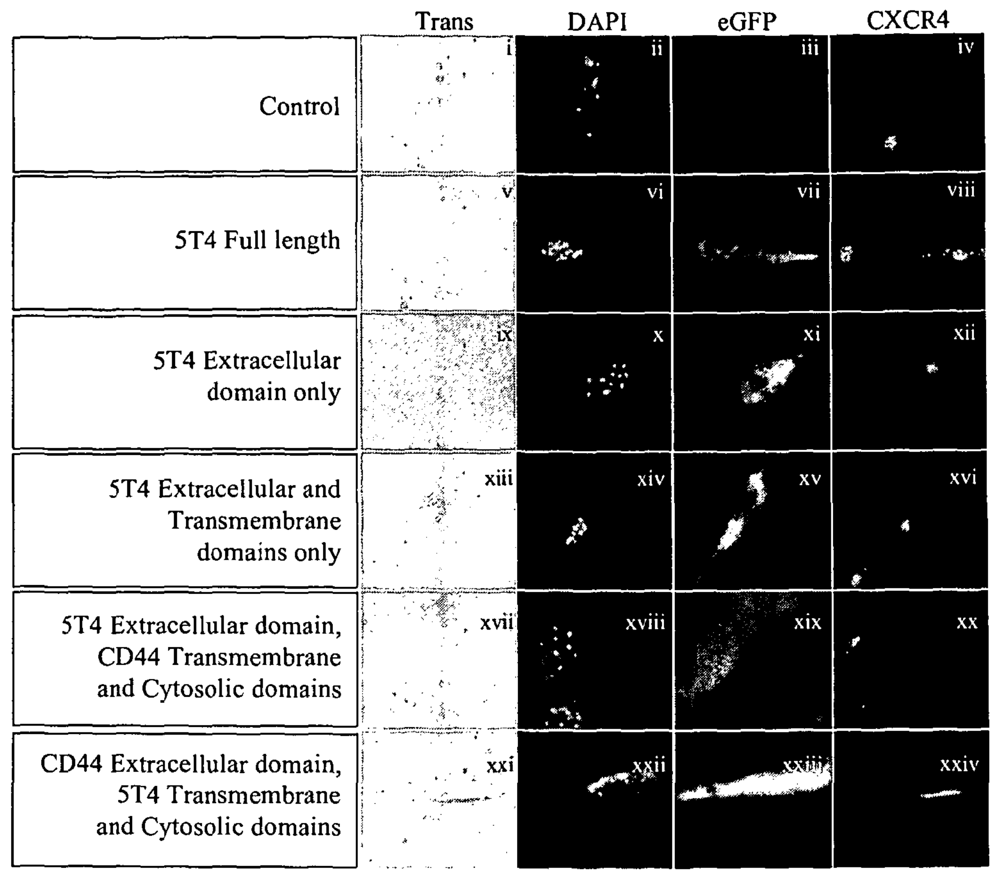
B
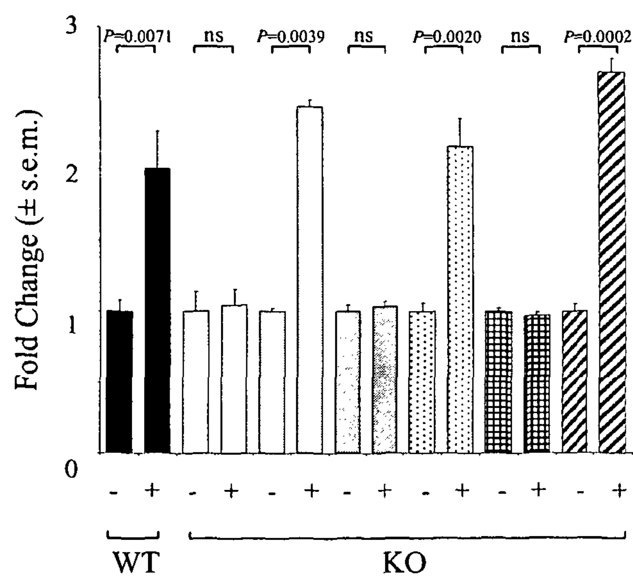
Figure 6

A
| Antibody | Subclass | Epitope |
|---|---|---|
| B5C9 | $IgG_1$ | Proximal LRR |
| P1C9 | $IgG_{2b}$ | Proximal LRR |
| B1C3 | $IgG_{2a}$ | Distal LRR |
| B3F1 | $IgG_{2a}$ | Distal LRR |
B
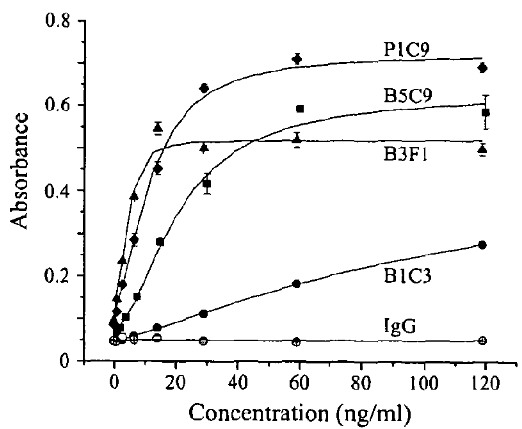
C
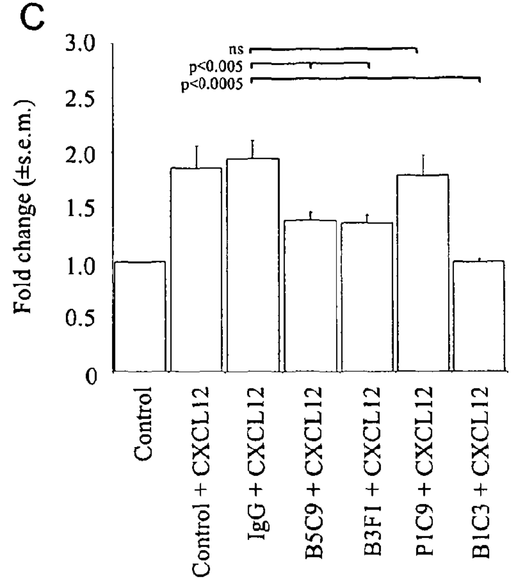
D
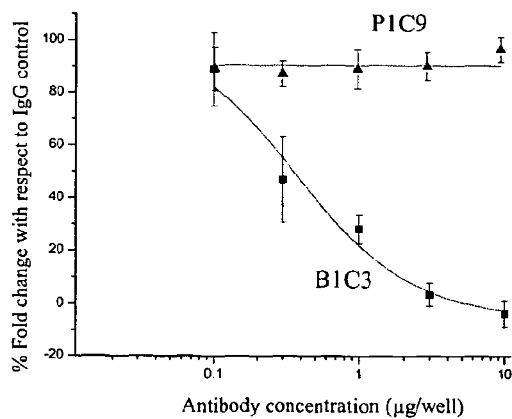
E
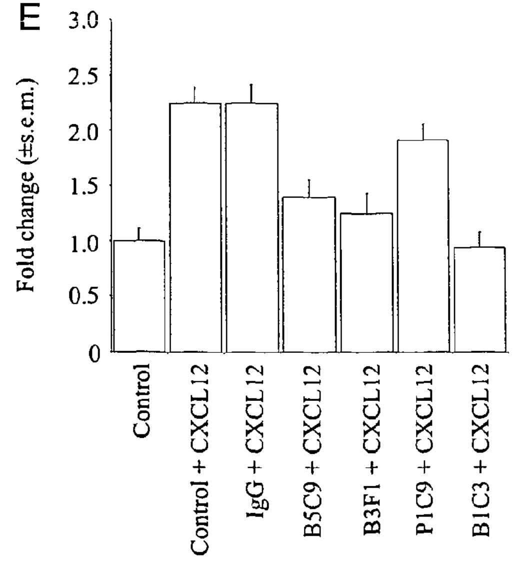
Figure 8

A
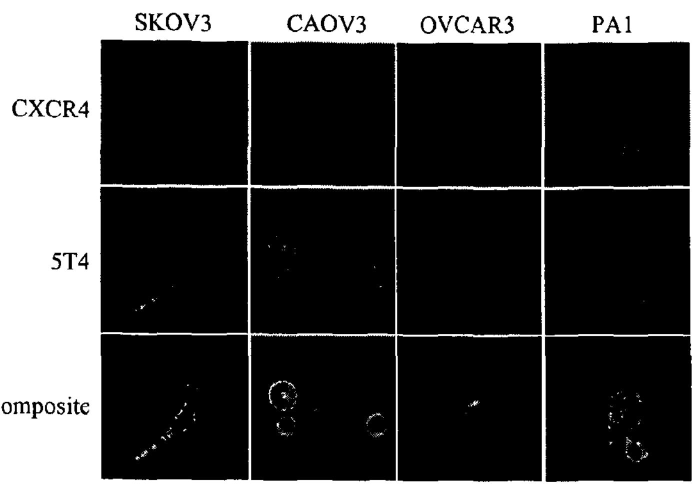
B
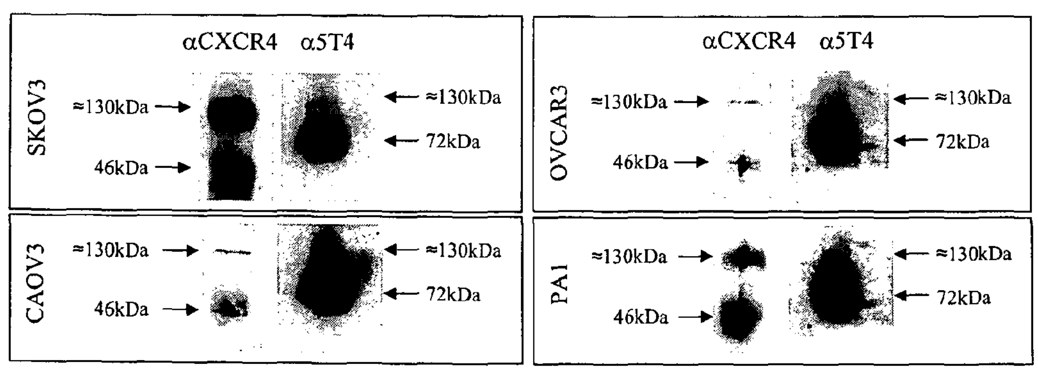
C
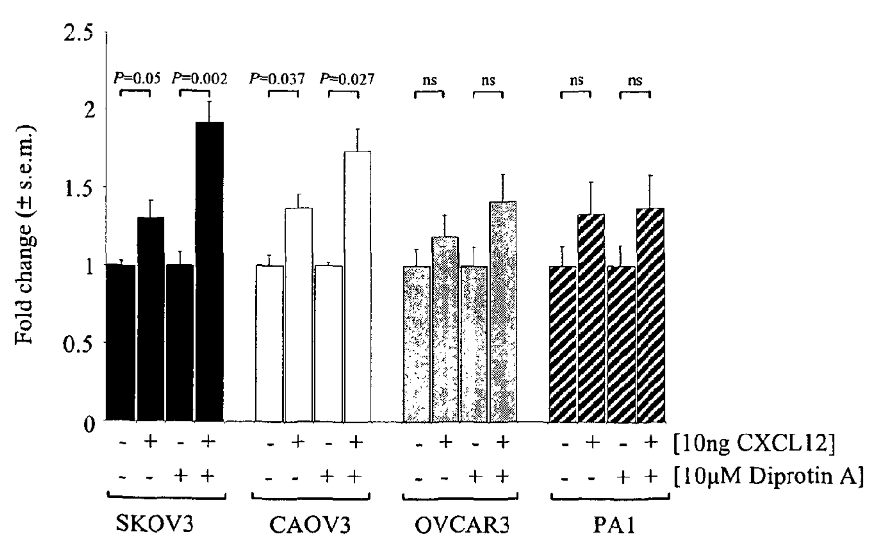
Figure 10

A
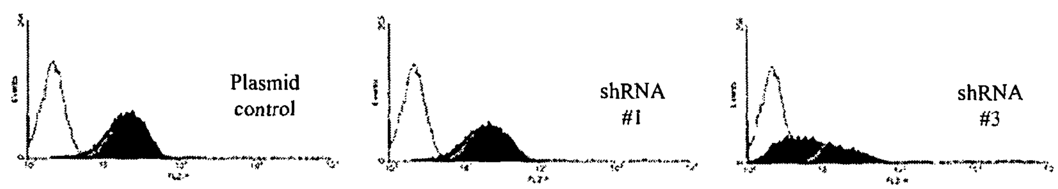
B
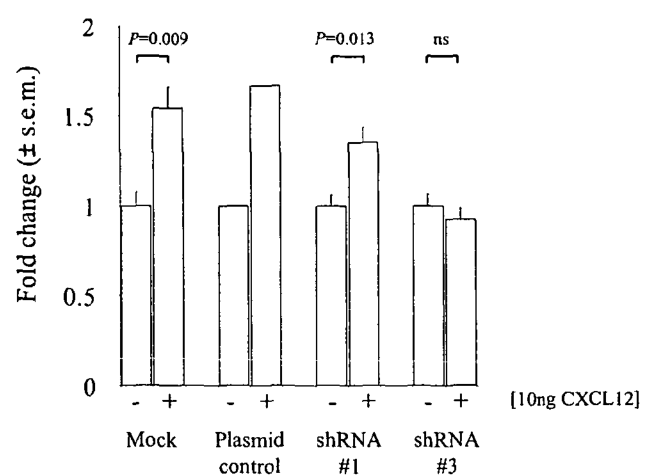
Figure 11

A
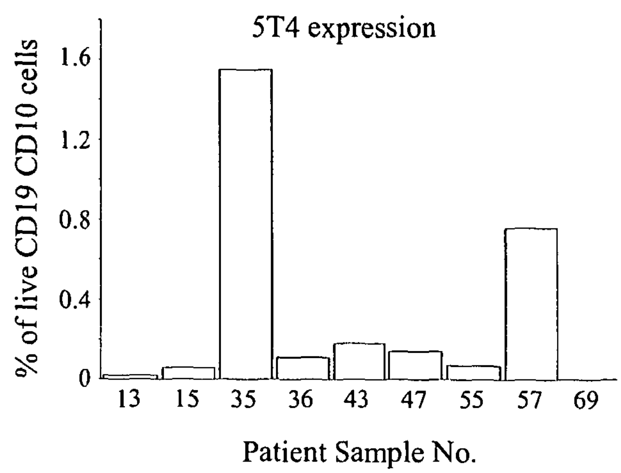
B
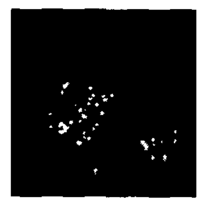
Patient Sample No. 57
Figure 13

A
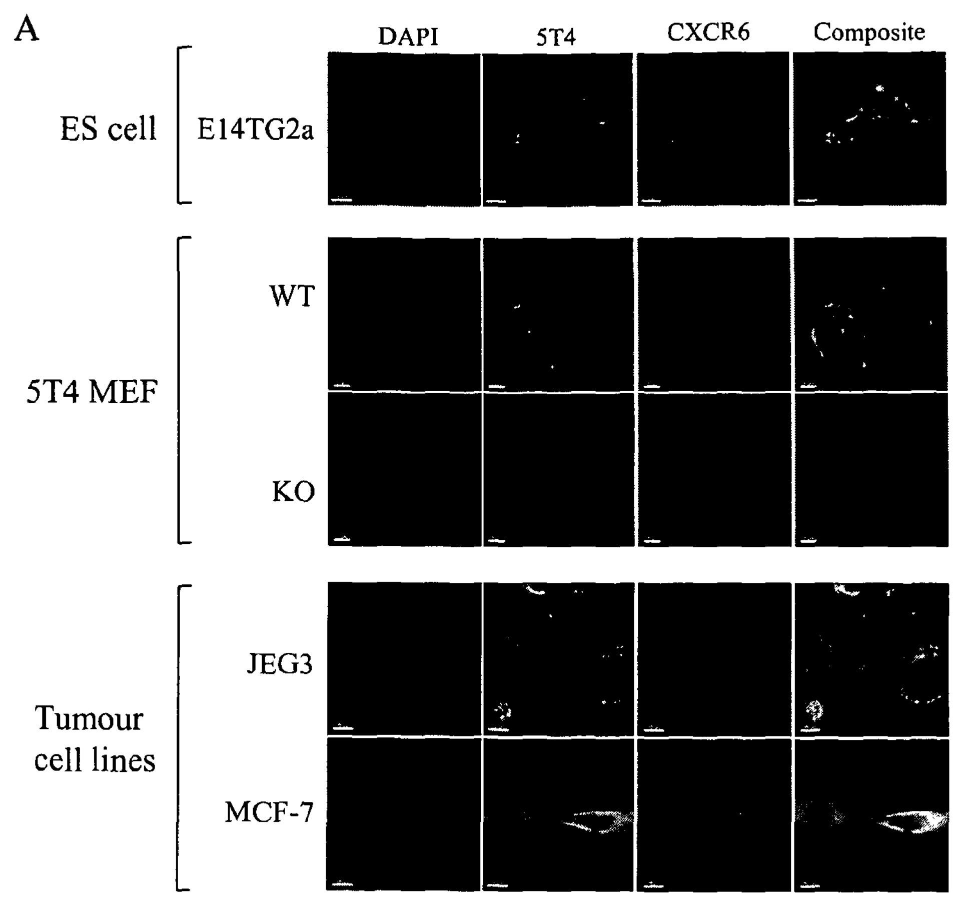
B
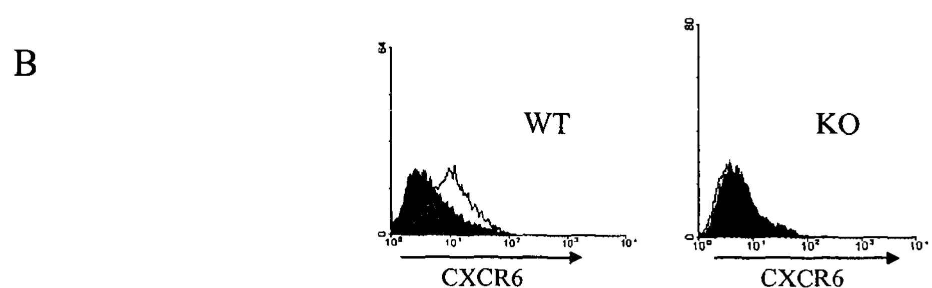
C
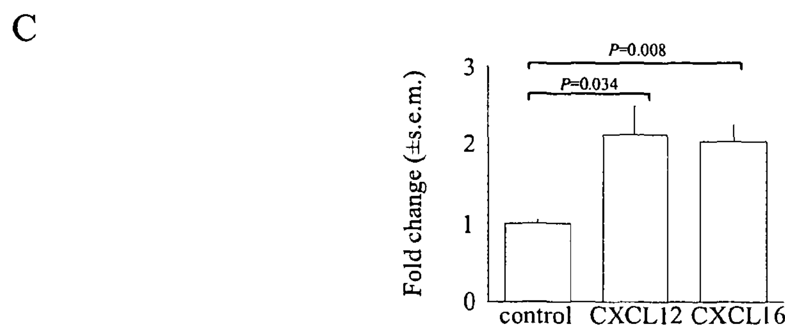
Figure 14

A
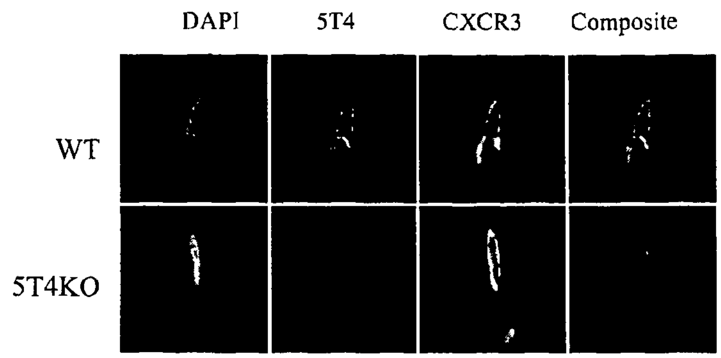
B
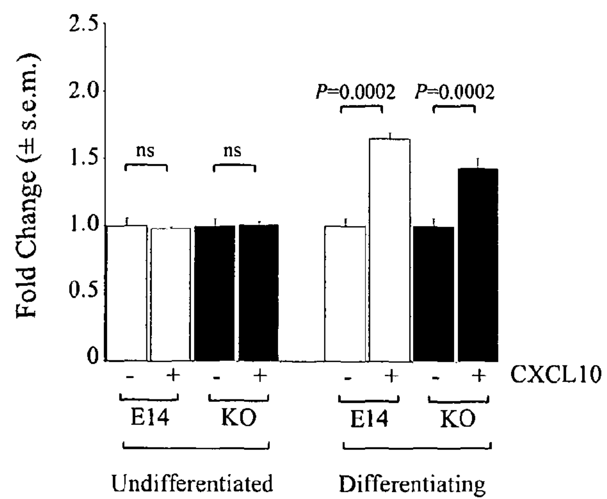
C
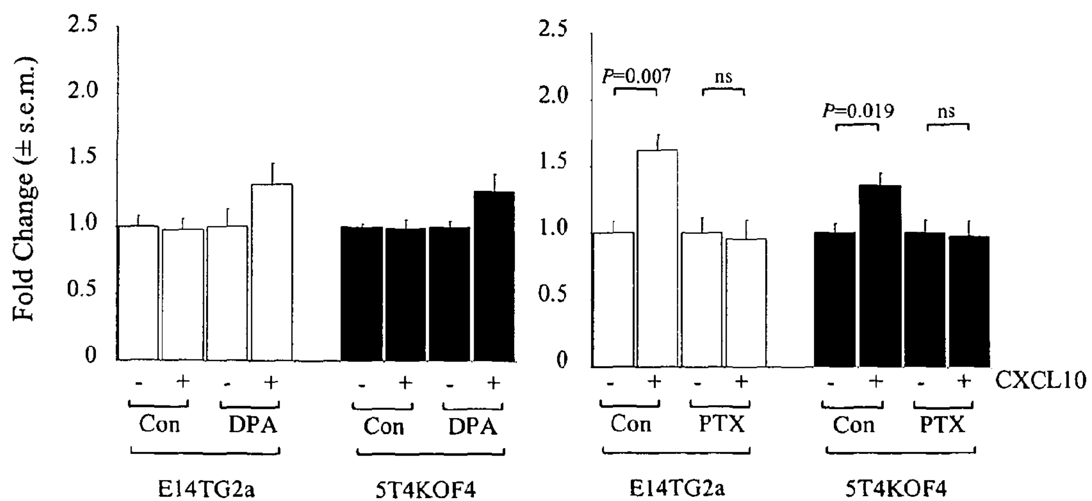
Figure 15

A

5T4 Transmembrane Domain

| | | |
|---|---|---|
| human | : | YVFLGIVLALIGAIFLLVLYL |
| mouse | : | YVFLGIVLALIGAIFLLVLYL |
| rat | : | YVFLGIVLALIGAIFLLVLYL |
| chimp | : | YVFLGIVLALIGAIFLLVLYL |
| macaque | : | YVFLGIVLALIGAIFLLVLYL |
| dog | : | YVFLGIVLALIGAIFLLVLYL |
| cattle | : | YVFLGIVLALIGAIFLLVLYL |
| opossum | : | YVFLGIVLALIGAIFLLVLYL |
| chicken | : | YVFLGIVLALIGAIFLLVLYL |
| platypus | : | YVFLGIVLALIGAIFLLVLYL |
| cat | : | YVFLGIVLALIGAIFLLVLYL |
| armadillo | : | YVFLGIVLALIGAIFLLVLYL |

B

Transmembrane Domain

| | | |
|---|---|---|
| 5T4 | : | YVFLG--IVLALIGAIFLLVLYL |
| PL5 | : | YVEFG--LVLALIGLIFLMVLYL |
| LRRC4 | : | -IIIGCFVAVTLIAAAMLIVFY- |

Figure 17

Human 5T4 paralogue (hPL5) (chromosome 11, location 11q13.4)
*Human Genomic*
>ref|NC_000011.8|NC_000011:74629070-74630891 Homo sapiens chromosome 11, reference assembly, complete sequence ATGAGTAACTTTCTCAGCCCACCCCTCATCCCTTCCTCCGGTAGTAGGAGCAGCTCTAAAGTCCTCCCCA
ACCCCCGAATTCTCCCTGGTGGTGACCCACCTGCCTGCTCTCCGCAGTCGGGCCCCGCCCCACACGTGCT
GGAGAAGGAGGAGGAAGGACCCAGCTTAAATGTTGGGGGTGGAGGAGGAGGAAAACCAAGTCGGAGCCTC
CAGGAGCCAAACTTCTCGGCAGCCCGGAGGGGCGGGGGCGGAGAGGATGAAGAGAAAGCGCAGCAGCCGA
CAGCCCTGATTCTCGGGAGCCTCCCACCCCGCCTCCCACGGCGAGGAGGGCGCGGAGACTCCGCTGGGGG
CGGAGGACGAGACCGGGAGGCGGGGAGGGGGGAGGCAAACCCTGCCCACTCGGCTCGGAGCCCGGAGCGG
CCGCGGAAGCCGGAGGCCGGCGCGCAGGGCGAGGGCACCGGGGGCGGGGGGCTCCGCTCCCCGTCTGACC
CCTCTTGCCCCCGGCCAGTCAGCCAGTAAGTGCGGCTCCTCAGACTTTCGAGACAGCGAACGGACCGACC
GGGACTGCCAGCCGCTCCGGGTCAAGGACTCGCCCCACCCGTGCCCCCCACCAGGCGCTCCCAACTCACT
GGTGAGCGCGGCGGCCCGGGCGCTGGATGCGGGGGCGGCCGCGATGGCCCCGCGCGCGGACAGCCGGGG
CTCCAGGGGCTGCTGCTCGTGGCGGCGGCGCTGAGCCAGCCCGCGGCACCCTGCCCCTTCCAGTGCTACT
GCTTCGGCGGCCCCAAGCTGCTGCTGCGCTGCGCGTCGGGAGCCGAGCTCCGCCAGCCTCCGCGGGACGT
GCCGCCCGACGCGCGCAACCTCACCATCGTAGGCGCCAACCTGACGGTGCTGCGCGCGGCCGCCTTCGCC
GGCGGGGACGGGGACGGCGACCAGGCGGCGGGCGTGCGCCTGCCGCTCCTGAGCGCGCTGCGCCTCACGC
ACAACCACATCGAGGTGGTGGAGGACGGCGCCTTCGACGGGCTGCCCAGCCTGGCGGCGCTCGACCTCAG
CCACAACCCGCTGCGCGCCCTGGGCGGCGGCGCCTTCCGCGGGCTGCCCGCGCTGCGCTCGCTGCAGCTC
AACCACGCGCTGGTGCGCGGCGGCCCCGCGCTGCTGGCCGCGCTGGACGCTGCGCTGGCACCGCTGGCCG
AGCTTCGCCTGCTGGGCCTAGCGGGCAACGCGCTGAGCCGTCTGCCGCCAGCCGCCCTGCGCCTGGCGCG
CCTGGAGCAGCTGGACGTGCGCCTCAACGCGCTGGCCGGCCTGGACCCCGACGAGCTGCGCGCGCTGGAG
CGCGATGGCGGCCTCCCCGGGCCGCGCCTGCTGCTCGCCGACAACCCCCTGCGCTGCGGCTGTGCCGCAC
GCCCCCTGCTGGCCTGGCTGCGCAACGCCACGGAGCGCGTGCCCGACTCGCGGCGCCTGCGCTGCGCCGC
CCCGCGGGCGCTGCTAGACCGGCCGCTACTGGACCTGGACGGGGCGCGGCTTCGCTGCGCGGACAGCGGC
GCCGACGCTCGCGGAGAGGAGGCGGAGGCCGCCGGCCCGGAGCTGGAAGCCTCCTACGTGTTCTTCGGGC
TGGTGCTGGCACTCATCGGCCTCATCTTCCTCATGGTGCTCTACCTAAACCGCCGCGGCATCCAGCGCTG
GATGCGCAACCTGCGCGAGGCGTGCCGGGACCAGATGGAGGGCTACCACTACCGCTACGAGCAGGACGCC
GACCCGCGCCGCGCGCCCGCGCCCGCCGCGCCCGCGGGCTCCCGCGCCACCTCCCCGGGCTCGGGGCTCT
GA

Figure 18

*Human mRNA (hPL5)*

>gi|113422496|ref|XM_497310.3| PREDICTED: Homo sapiens similar to hCG1820409 (LOC441617), mRNA ATGAGTAACTTTCTCAGCCCACCCCTCATCCCTTCCTCCGGTAGTAGGAGCAGCTCTAAAGTCCTCCCCA
ACCCCCGAATTCTCCCTGGTGGTGACCCACCTGCCTGCTCTCCGCAGTCGGGCCCCGCCCCACACGTGCT
GGAGAAGGAGGAGGAAGGACCCAGCTTAAATGTTGGGGGTGGAGGAGGAGGAAAACCAAGTCGGAGCCTC
CAGGAGCCAAACTTCTCGGCAGCCCGGAGGGGCGGGGGCGGAGAGGATGAAGAGAAAGCGCAGCAGCCGA
CAGCCCTGATTCTCGGGAGCCTCCCACCCCGCCTCCCACGGCGAGGAGGGCGCGGAGACTCCGCTGGGGG
CGGAGGACGAGACCGGGAGGCGGGGAGGGGGGAGGCAAACCCTGCCCACTCGGCTCGGAGCCCGGAGCGG
CCGCGGAAGCCGGAGGCCGGCGCGCAGGACTTTCGAGACAGCGAACGGACCGACCGGGACTGCCAGCCGC
TCCGGGTCAAGGACTCGCCCCACCCGTGCCCCCCACCAGGCGCTCCCAACTCACTGGTGAGCGCGGCGGC
CCGGGCGCTGGATGCGGGGGCGGCCGCGATGGCCCCGCGCGCGGGACAGCCGGGGCTCCAGGGGCTGCTG
CTCGTGGCGGCGGCGCTGAGCCAGCCCGCGGCACCCTGCCCCTTCCAGTGCTACTGCTTCGGCGGCCCCA
AGCTGCTGCTGCGCTGCGCGTCGGGAGCCGAGCTCCGCCAGCCTCCGCGGGACGTGCCGCCCGACGCGCG
CAACCTCACCATCGTAGGCGCCAACCTGACGGTGCTGCGCGCGGCCGCCTTCGCCGGCGGGGACGGGGAC
GGCGACCAGGCGGCGGGCGTGCGCCTGCCGCTCCTGAGCGCGCTGCGCCTCACGCACAACCACATCGAGG
TGGTGGAGGACGGCGCCTTCGACGGGCTGCCCAGCCTGGCGGCGCTCGACCTCAGCCACAACCCGCTGCG
CGCCCTGGGCGGCGGCGCCTTCCGCGGGCTGCCCGCGCTGCGCTCGCTGCAGCTCAACCACGCGCTGGTG
CGCGGCGGCCCCGCGCTGCTGGCCGCGCTGGACGCTGCGCTGGCACCGCTGGCCGAGCTTCGCCTGCTGG
GCCTAGCGGGCAACGCGCTGAGCCGTCTGCCGCCAGCCGCCCTGCGCCTGGCGCGCCTGGAGCAGCTGGA
CGTGCGCCTCAACGCGCTGGCCGGCCTGGACCCCGACGAGCTGCGCGCGCTGGAGCGCGATGGCGGCCTC
CCCGGGCCGCGCCTGCTGCTCGCCGACAACCCCCTGCGCTGCGGCTGTGCCGCACGCCCCCTGCTGGCCT
GGCTGCGCAACGCCACGGAGCGCGTGCCCGACTCGCGGCGCCTGCGCTGCGCCGCCCCGCGGGCGCTGCT
AGACCGGCCGCTACTGGACCTGGACGGGGCGCGGCTTCGCTGCGCGGACAGCGGCGCCGACGCTCGCGGA
GAGGAGGCGGAGGCCGCCGGCCCGGAGCTGGAAGCCTCCTACGTGTTCTTCGGGCTGGTGCTGGCACTCA
TCGGCCTCATCTTCCTCATGGTGCTCTACCTAAACCGCCGCGGCATCCAGCGCTGGATGCGCAACCTGCG
CGAGGCGTGCCGGGACCAGATGGAGGGCTACCACTACCGCTACGAGCAGGACGCCGACCCGCGCCGCGCG
CCCGCGCCCGCCGCGCCCGCGGGCTCCCGCGCCACCTCCCCGGGCTCGGGGCTCTGA

Human protein PL5
MAPRAGQPGLQGLLLVAAALSQPAAPCPFQCYCFGGPKLLLRCASGAELRQPPRDVPPD
ARNLTIVGANLTVLRAAAFAGGDGDGDQAAGVRLPLLSALRLTHNHIEVVEDGAFDGL
PSLAALDLSHNPLRALGGGAFRGLPALRSLQLNHALVRGGPALLAALDAALAPLAELRL
LGLAGNALSRLPPAALRLARLEQLDVRLNALAGLDPDELRALERDGGLPGPRLLLADNP
LRCGCAARPLLAWLRNATERVPDSRRLRCAAPRALLDRPLLDLDGARLRCADSGADAR
GEEAEAAGPELEASYVFFGLVLALIGLIFLMVLYLNRRGIQRWMRNLREACRDQMEGY
HYRYEQDADPRRAPAPAAPAGSRATSPGSGL

B

| | |
|---|---|
| Optimal Kozak sequence (Kozak, 1987) | GCCRCC**AUG**G |
| First in-frame AUG codon context | CGGAAA**AUG**A |
| Second in-frame AUG codon context | GCCGCG**AUG**G |

C

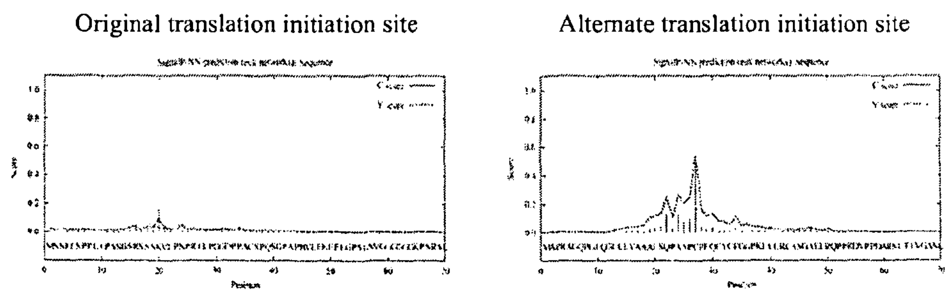

D

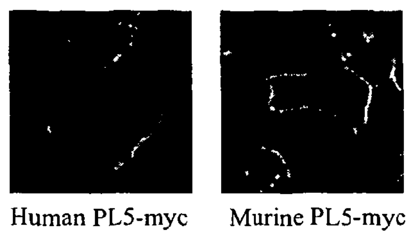

Figure 20

Human 5T4 aligned with human PL5, transmembrane region highlighted (*)

```
5T4 : MPGGCSRGPAAGDGRLRLARLALVLLGWVSSSSPTSSASSFSSSAPFLASAVSAQPPLPDQCPALCECSEAARTVKCVNRN
PL5 : ------MAPRAG--QPGLQGLLLVAAALSQPAAP----------CPFQCYCFGG-PKLLLRCASGAELRQPPRDVPPDARN

5T4 : LTEVPTDLPAYVRNLFLTGNQLAVLPAGAFARRPPLAELAALNLSGSRLDEVRAGAFEHLPSLRQLDLSHNPLADLSPFAF
PL5 : LTIVGANLTVLRAAAFAGGD-----GDGDQAAGVRLPLLSALRLTHNHLEVVEDGAFDGLPSLAALDLSHNPLRALGGGAF

5T4 : SGSNASVSAPSPLVELILNHIVPPEDERQNRSFEGMVVAALLAGRALQGLRRLELASNHFLYLPRDVLAQLPSLRHLDLSN
PL5 : RG-------LPALRSLQLNHALVRGG------------PALLA--ALD-----------------AALAPLAELRLLGLAG

5T4 : NSLVSLTYVSFRNLTHLESLHLEDNALKVLHNGTLAELQ---GLPHIRVFLDNNPWVCDCHMADMVTWLK-ETEVVQGKDR
PL5 : NALSRLPPAALR-LARLEQLDVRLNALAGLDPDELRALERDGGLEGPRLLLADNPLRCGCAARPLLAWLRNATERVPDSRR

                                                        *********************
5T4 : LTCAYPEKMRNRVLLELNSADLDCDP-----------ILPPSLQTSYVFLGIVLALIGAIFLLVLYLNRKGIKKWMHNIRD
PL5 : LRCAAPRALLDRPLLDLLGARLRCADSGADARGEEAEAAGPELEASYVFFGLVLALIGLIFLMVLYLNRRGIQRWMRNLRE
                                                        *********************

5T4 : ACRDHMEGYHYRYEINADPR-----------LTNLSSNSDV
PL5 : ACRDQMEGYHYRYEQDADPRRAPAPAAPAGSRATSPGSGL
```

Figure 21

Murine 5T4 paralogue (chromosome 7, location 7E2)(mPL5)
*Murine Genomic*
>ref|NC_000073.5|NC_000073:c106777643-106772343 Mus musculus chromosome 7, reference assembly (C57BL/6J)

AGCATCAAACAGACAGACATTTATTGAAATACCTACTGGACATAATACACTGGCAACTCCCGAAGGGAGA
GAGCCCTTCTTCCAGAGAACACAACAATTCCCTCATTCATACAACACAGAGAACACGACTCCCCTTGCCT
AATGATGTCCGTTCTTCTTAAGCTTCTCTTCCCCAGCTGAGGTGTTTAACACCAGTCAATGAAAGCTGCC
TGCAACTATGTAACCCCTCTCCCTCGGAGAAGGCAGTCAGCAGCAATGAGAAGGCAGCCACCATGAAAAC
CGGAGAGGGAGTTTTGGCCTTGGCAGTGGTCTACACTTCCGTAGGGACTGGAGGCAGGTCTCCATGCAGT
TAAGTGGGGGAAGCAGGCTGTTCTGGTCACTCATGATTTGAGCACTTGTGCTGTATGAGAAAAGGTACCT
GTGACCTCCAAAGGCCAAGGACATAGTCCAGAGCAGGAGAGGGCCCCGTCTGTACGCATTCACTTTCACA
AGAGTCTGCAAGCTGCCCCTCTAAGGCTGCAGTTGAACCTGTGTTGGCCCAGTGAGTGAACACTCAAGCA
CTTTGGTATGCTTCTGACTCTATGGACACATACCAGGTTACACTCAAAGCCGCTATGTACACAGGCACGA
ATGTGCCTGCATGTGTCTATGTGAGACACATTTGTTTGGAACTGCTGTGTGCAAGCCTCCCGTGCACATG
CATGCACATCCAAGTAAGAATAAATTTGATAGACCACACATGGGCATGTGTAAGTCTGTTTGTGTAAAGT
TTGCCTTTTTGTGTAGAGGCACACGTGTGTAAACTCAGGTGGCCATGTATACAGACATGTCCAGCTCTAA
AAGCTACTACTGTCATCTGCTAGCATCTGGAGGTTATCATGGAGACAGGACTAGGTCAATATGAGCTGAG
GGAGTCCAGCAAGATCACCAGCCTGGTCCTTAGTGTTGGTATTTGCCTGAGACCCAGGGAATGCAGGATA
TGCCTCAGAAAGTGGTTTCAATTTGCTGGTCGATCTTCTAAATGCAACTTCAGGGAAGAAACCAACCAGT
AGTCTTCAGTTCAGGAGAAAGAGACTGACTGATGCTTATGGGGAGGAGGGGAGCCTCTATCCCAACCAGC
TCTGCCAAGTAAGATACTCGAATGGCCTGCAGATCAAATGTCAGCTTCTCCAACCTGAATAATTCATGCC
AAGACCAGGAATGCTCCCTCCTCTGGAGTCTGTCTCTTTAAATCAGGTCTTGAGCTTCTCAATTCTGGAG
GAAAAAAAAAGTAAATAAGTAAAACCCAGAAAGAAAGAAAAACAAAACAAAACAAAACAAGCCTATTAAC
AGCTCAGCCCCCACCTCAGCCCTGGATTTTACCACACCCCCACCCTCCACTACAAAATCAGTTCCTGATT
TTCCTGCTCCTAGAGCCCTCTCCCCAACCGGCACACCACTCAATATTGACTGGTAGGGCAATTTGGAGGG
GAAGGGGCACAGTATCCTGGCAGTACTCAGTGCTGGGGCGGGGTGGGCAAGCAAAGAGCTGAATCACTCC
ACCCACCGCTCCCTGAGCCTAGGAGGGGCCCAGCCTGAAAGGTGGAACCAATGGGAGTGGTCTTGGCAGA
GGCAGAGCAGCCTGAATTAGGGCGCGGGAGATGTGGGGACAGAGGGTGTTTTAGAACATAGAAGAGGGTC
GATAAAAGACTGGACACACAGGACCTGCAGAGTTTTAGACACAGCCTAAGGGAACTGGGTTCGCAAAGGA
GACATCCAAGGCTAGGGATTTTCCAGGCTCGCTCCCTTAGCACAGCTCCTTTCCTTGACTACAAGAAGAG
TAACTTTGTCAGCCCACCCCTCAGCCCTGCCTCCTTTTCTAGGGACAGCTCTAAACTCTCCCACCTTCTC
TGGGTGCACAGATCCACCTGCCAGGTCAGCCCTGAGGGCCCCGCCCCACGTGTGCTTCGGAGGGAGGAGG
AAAGAAGCTGCCTAAACGAAGGGGGTGGGGAAAGAAGCAAGTCAGAGCTTGGGGAGCCAAACTTCTCAGC
AGCTCGTGAACTAGAGAGCAGGGGAGCAAGAGAGCGCAGCGGCCCTAAGCCTGCATCTCCGGAGCCTCCC
ACCCCGCCTCCCTTGCGAGGAGGTGCGGAGACTCCGCTGGGGGCGGAGGAGGCGGCCAGGAGGCGGGGAG
GGGGAGGCAAACCCTGCCCACTCGGCTCGGAGCCCGGAACAGCCGCGGAAGTCGGAGGCCGGAGCGCAGG
GCGACGAGGGCAGCGAGGGCGGGGGCTCCGCTCCCCGCCTGACCCCTGTAGCCCCCAGCCATCAAAGTG
AAGGCTCCTCGGACTTTACAAGCTGGAGGACGGACCGGTCGGAACTGTCAGCTGCTCCGGGTCAAGGTCT
AGCCCACAGCCACCTTCCCGTGCCACCCCCATCCCATCATCTCCAAACGCTCCCAATTCACTGGTGAGCG
CTGCGGGCCGGGGGCTGGATGCGGGGACGGCCGCGATGGCCCCGCGCGCGGGACAGCGGGGGCTCTGGAG
CCCGCTGCCAGGGCTGCTGCTCTTGGCGGCGGCGCTGAGCCGGCCCGCCGCGCCCTGTCCCTTCCAGTGT
TACTGCTTCGGCAGCCCCCGGTTAATGTTGCGCTGCGCGTCGGGCGCGGAGCTCCGGCAGCCGCCCCGGG
ACGTGCCACCCGACGCGCGCAACCTCACCATCGTGGGCGCCAACCTGACCGTGCTGCGCGCCGCAGCCTT
CGCGGGAGGGGGCGAGGGGGCGACGGACGGCGTGCGCCTACCGCTCCTTACCGCGCTGCGCCTCACACAC
AACAACATCGAGGTAGTAGAGGACGGTGCCTTCGACGGGTTGCCCAGCCTGGCGGCACTCGACCTAAGCC
ACAACCCGCTACGCGCCCTGGGCTACCGCGCCTTTCGCGGGCTGCCTGCGCTGCGCTCACTACAGCTCAA
TCACGCGCTGGCTCGAGGCAGCCCCGGGATGCTGGATGCACTGGACGCCGCTCTGGCCCCCCTGGCCGAG
CTTCGCCTGCTGGGCTTGGTAGGCAACGCGCTGAGCCGCCTGCCACTCGCCGCGCTGCGCCTGCCCCGCC
TGGAGCAGCTGGATGCGCGTGTCAACGCGCTGGCCGGCCTGGGCCCGGACGAGCTGAGCGCGCTTGAGCG
CGATGGCGACCTGCCCCAGCCGCGCCTGCTGCTGGCGGACAACCCACTGAGCTGTGGGTGCACCTCGCGC
CCCCTGCTGGCCTGGCTGCACAACGCCACCGAGCGCGTACCCGACGCGCGCCGCCTGCGCTGCGCTTCCC
CGCGCGTACTGTTGGACCGGCCTCTGATAGACCTGGACGAGGCGCGACTAGGTTGCTCCGACGGCGATGC
ACACGAGAGCGGGGAAGGGATAGACGTCGCCGGCCCGGAGTTGGAAGCCTCTTACGTCTTCTTCGGGCTG
GTGCTGGCACTCATCGGCCTCATCTTCCTCATGGTGCTCTACCTAAACCGCCGCGGCATCCAACGCTGGA
TGCACAATTTGCGCGAGGCCTGCAGAGATCAGATGGAGGGCTACCACTACCGCTACGAGCAGGATGCAGA

Figure 22A

CCCACGCCGCGCGCCTGCTCCGGCCGCCCCTGCCGGCTCCCGGGCCACTTCTCCAGGCTCGGGTCTCTGA
GCATCACCTCCCTAGTGGGAGGCTGTTCCTATCAGCTGATGACTTTACTTGGGCCATGCAGCCTTTCTCT
GCCTGGCCTGGGCCCCGGAGATAACACACTTACGAGTTTGGATCTCTGAGACCTTTGGATCAATCGTAGT
ATCTCTCCCATACAGAAATTCCAAGGTGTACTCTTTCCCTGGCCTTAGAGTTTCCAGATCAAAAACCCAG
AAATCTGTTTTCAGAAACAAATCCTGCCTGCCGGTCCTTACTGGACCATTGAAATTGAAATTCCTTCTCC
CTGTCCAGGCTCACCCAAAGATCCTGCTCTTCCATTTTGAAATCTCTAGCACTTTCTCCACCTTTCTATA
TGCTTTAAGCCAGACACCCTGGCTAGATTGCACTGACCCCTGCTCCAGGGTAGAAGACCTCAGTCCCTTT
CTCAGAGTTCTGGGGGGAGGGGGGTCTACCCTTCTGGTCTCTTTGGAAGGTTTTTATGAAGTTTGAGCT
TTTTGTCCCACCTCAGAACTCTGGGCTCTCCATCATGTAACCCAAATCTGAAGGCTTTCAGTGGTCTCCT
CTAATCTGATTTGCTTCATACCCTGGTTCTAGCTCAGGCCCTTCCATTCCTTGCTCTTGGCTGGGTTTCA
GCTCCGGCCTTGTCTCTTTCATGCCAGGGGCAAGGAAGGCTTGGTGTAGAATCCAAGCCTTAGCCTTTCT
GTTGCGGCTCTAATGTCCCAACAGAGTTTGTCCTCCATCTAAAAGTCAGCTCTTCACCCCAGTCACTTTC
ATGCCCTGGCCCAAGTCTTAGGCTCTCAGTCCCCTTGACATCCATCGCTGGCACTTTTACCATTCATTGA
CCAGGGGCCAGAGAGGGCTCTTCCCCCATGGTGGGGTGCTACCCACTGCCCTCCTAGGAGATGTTCTCCC
ATCCTGCAGGACAAGTAAAAGCACCCCCATAGCATATAGGCAGACTTGAGGGAGGAAGGGAGCAGGTGGG
GTGAGCAGGGTCTCCAATCCAGGGCCACTGGTCTGTCTGGAAACGTGAGGCTTGGAGCTGCTGCCCATCT
GTGCTCTGTGCTTCACCATCCACACGGTCCTCCCCTGGGAACTCCTTGCTACCACCTCTCATGCCTTCTG
GAAGGGGATGGAGTCTGACCTCTTGTCTCAGTCTCAGTGGAAAGCTTTCCTGGTCAAGGTCATGGCCTCA
GTGCCCTGCCTTCTGCATGATCCCAAAGCACAATGGTGAGTGAGGGGGAACTGCCTCCCTGCCTCTCACC
CTAAGTCAGGCAGAATGGCAGGCCTGTGCTGCCTCTGCACAGGAAGGTCTTCCTCCTCTGTATATCGGCT
TGAGGCCCGCTGTCCCCATCCTCAACTGAGAAATCTGGACCTCCCTTGGGCTGTTTTCTATAAAGTCTGC
AATAATCTCCGATGCTCTCTGCTCTTGTAAGTGGTTCTGTGTTTGTCCTACTGACCTTGGGGCATTGGTG
GGCGTGAAAGGTGACAAGAGGTGGCCATTTGGGGCAGTGGCCCTTATGCACTCTCTGGAGATGTGGGAAA
AAGAAACAGGCTGTGAGTACACATAGCAAGACTGAGGCTAGACACAGGGGGTGGGGGTGCTCTCCGTCAT
TCTCCAGCCTGCTTTTTAATGGTCTGAAACGGGCTTATCCACAGCCAGCAT

Figure 22B

*Murine mRNA (mPL5)*
>gi|94380878|ref|XM_486328.4| PREDICTED: Mus musculus predicted gene,
EG245190 (EG245190), mRNA

```
AGCATCAAACAGACAGACATTTATTGAAATACCTACTGGACATAATACACTGGCAACTCCCGAAGGGAGA
GAGCCCTTCTTCCAGAGAACACAACAATTCCCTCATTCATACAACACAGAGAACACGACTCCCCTTGCCT
AATGATGTCCGTTCTTCTTAAGCTTCTCTTCCCCAGCTGAGGTGTTTAACACCAGTCAATGAAAGCTGCC
TGCAACTATGTAACCCCTCTCCCTCGGAGAAGGCAGTCAGCAGCAATGAGAAGGCAGCCACCATGAAAAC
CGGAGAGGGAGTTTTGGCCTTGGCAGTGGTCTACACTTCCGTAGGGACTGGAGGCAGGTCTCCATGCAGT
TAAGTGGGGGAAGCAGGCTGTTCTGGTCACTCATGATTTGAGCACTTGTGCTGTATGAGAAAAGGTACCT
GTGACCTCCAAAGGCCAAGGACATAGTCCAGAGCAGGAGAGGGCCCCGTCTGTACGCATTCACTTTCACA
AGAGTCTGCAAGCTGCCCCTCTAAGGCTGCAGTTGAACCTGTGTTGGCCCAGTGAGTGAACACTCAAGCA
CTTTGGTATGCTTCTGACTCTATGGACACATACCAGGTTACACTCAAAGCCGCTATGTACACAGGCACGA
ATGTGCCTGCATGTGTCTATGTGAGACACATTTGTTTGGAACTGCTGTGTGCAAGCCTCCCGTGCACATG
CATGCACATCCAAGTAAGAATAAATTTGATAGACCACACATGGGCATGTGTAAGTCTGTTTGTGTAAAGT
TTGCCTTTTTGTGTAGAGGCACACGTGTGTAAACTCAGGTGGCCATGTATACAGACATGTCCAGCTCTAA
AAGCTACTACTGTCATCTGCTAGCATCTGGAGGTTATCATGGAGACAGGACTAGGTCAATATGAGCTGAG
GGAGTCCAGCAAGATCACCAGCCTGGTCCTTAGTGTTGGTATTTGCCTGAGACCCAGGGAATGCAGGATA
TGCCTCAGAAAGTGGTTTCAATTTGCTGGTCGATCTTCTAAATGCAACTTCAGGGAAGAAACCAACCAGT
AGTCTTCAGTTCAGGAGAAAGAGACTGACTGATGCTTATGGGGAGGAGGGGAGCCTCTATCCCAACCAGC
TCTGCCAAGTAAGATACTCGAATGGCCTGCAGATCAAATGTCAGCTTCTCCAACCTGAATAATTCATGCC
AAGACCAGGAATGCTCCCTCCTCTGGAGTCTGTCTCTTTAAATCAGGTCTTGAGCTTCTCAATTCTGGAG
GAAAAAAAAAGTAAATAAGTAAAACCCAGAAAGAAAGAAAAACAAAACAAAACAAAACAAGCCTATTAAC
AGCTCAGCCCCCACCTCAGCCCTGGATTTTACCACACCCCCACCCTCCACTACAAAATCAGTTCCTGATT
TTCCTGCTCCTAGAGCCCTCTCCCCAACCGGCACACCACTCAATATTGACTGGTAGGGCAATTTGGAGGG
GAAGGGGCACAGTATCCTGGCAGTACTCAGTGCTGGGGCGGGGTGGCAAGCAAAGAGCTGAATCACTCC
ACCCACCGCTCCCTGAGCCTAGGAGGGGCCCAGCCTGAAAGGTGGAACCAATGGGAGTGGTCTTGGCAGA
GGCAGAGCAGCCTGAATTAGGGCGCGGAGATGTGGGGACAGAGGGTGTTTTAGAACATAGAAGAGGGTC
GATAAAAGACTGGACACACAGGACCTGCAGAGTTTTAGACACAGCCTAAGGGAACTGGGTTCGCAAAGGA
GACATCCAAGGCTAGGGATTTTCCAGGCTCGCTCCCTTAGCACAGCTCCTTTCCTTGACTACAAGAAGAG
TAACTTTGTCAGCCCACCCCTCAGCCCTGCCTCCTTTTCTAGGGACAGCTCTAAACTCTCCCACCTTCTC
TGGGTGCACAGATCCACCTGCCAGGTCAGCCCTGAGGGCCCCGCCCCACGTGTGCTTCGGAGGGAGGAGG
AAAGAAGCTGCCTAAACGAAGGGGGTGGGGAAAGAAGCAAGTCAGAGCTTGGGGAGCCAAACTTCTCAGC
AGCTCGTGAACTAGAGAGCAGGGGAGCAAGAGAGCGCAGCGGCCCTAAGCCTGCATCTCCGGAGCCTCCC
ACCCCGCCTCCCTTGCGAGGAGGTGCGGAGACTCCGCTGGGGGCGGAGGAGGCGGCCAGGAGGCGGGGAG
GGGGAGGCAAACCCTGCCCACTCGGCTCGGAGCCCGGAACAGCCGCGGAAGTCGGAGGCCGGAGCGCAGG
GCGACGAGGGCAGCGAGGGCGGGGGGCTCCGCTCCCCGCCTGACCCCTGTAGCCCCCAGCCATCAAAGTG
AAGGCTCCTCGGACTTTACAAGCTGGAGGACGGACCGGTCGGAACTGTCAGCTGCTCCGGGTCAAGGTCT
AGCCCACAGCCACCTTCCCGTGCCACCCCCATCCCATCATCTCCAAACGCTCCCAATTCACTGGTGAGCG
CTGCGGGCCGGGGGCTGGATGCGGGGACGGCCGCGATGGCCCCGCGCGCGGACAGCGGGGGCTCTGGAG
CCCGCTGCCAGGGCTGCTGCTCTTGGCGGCGGCGCTGAGCCGGCCCGCCGCGCCCTGTCCCTTCCAGTGT
TACTGCTTCGGCAGCCCCCGGTTAATGTTGCGCTGCGCGTCGGGCGCGGAGCTCCGGCAGCCGCCCCGGG
ACGTGCCACCCGACGCGCGCAACCTCACCATCGTGGGCGCCAACCTGACCGTGCTGCGCGCCGCAGCCTT
CGCGGGAGGGGGCGAGGGGGCGACGGACGGCGTGCGCCTACCGCTCCTTACCGCGCTGCGCCTCACACAC
AACAACATCGAGGTAGTAGAGGACGGTGCCTTCGACGGGTTGCCCAGCCTGGCGGCACTCGACCTAAGCC
ACAACCCGCTACGCGCCCTGGGCTACCGCGCCTTTCGCGGGCTGCCTGCGCTGCGCTCACTACAGCTCAA
TCACGCGCTGGCTCGAGGCAGCCCCGGGATGCTGGATGCACTGGACGCCGCTCTGGCCCCCCTGGCCGAG
CTTCGCCTGCTGGGCTTGGTAGGCAACGCGCTGAGCCGCCTGCCACTCGCCGCGCTGCGCCTGCCCCGCC
TGGAGCAGCTGGATGCGCGTGTCAACGCGCTGGCCGGCCTGGGCCCGGACGAGCTGAGCGCGCTTGAGCG
CGATGGCGACCTGCCCCAGCCGCGCCTGCTGCTGGCGGACAACCCACTGAGCTGTGGGTGCACCTCGCGC
CCCCTGCTGGCCTGGCTGCACAACGCCACCGAGCGCGTACCCGACGCGCGCCGCCTGCGCTGCGCTTCCC
CGCGCGTACTGTTGGACCGGCCTCTGATAGACCTGGACGAGGCGCGACTAGGTTGCTCCGACGGCGATGC
ACACGAGAGCGGGGAAGGGATAGACGTCGCCGGCCCGGAGTTGGAAGCCTCTTACGTCTTCTTCGGGCTG
GTGCTGGCACTCATCGGCCTCATCTTCCTCATGGTGCTCTACCTAAACCGCCGCGGCATCCAACGCTGGA
TGCACAATTTGCGCGAGGCCTGCAGAGATCAGATGGAGGGCTACCACTACCGCTACGAGCAGGATGCAGA
CCCACGCCGCGCGCCTGCTCCGGCCGCCCCTGCCGGCTCCCGGGCCACTTCTCCAGGCTCGGGTCTCTGA
```

Figure 23A

GCATCACCTCCCTAGTGGGAGGCTGTTCCTATCAGCTGATGACTTTACTTGGGCCATGCAGCCTTTCTCT
GCCTGGCCTGGGCCCCGGAGATAACACACTTACGAGTTTGGATCTCTGAGACCTTTGGATCAATCGTAGT
ATCTCTCCCATACAGAAATTCCAAGGTGTACTCTTTCCCTGGCCTTAGAGTTTCCAGATCAAAAACCCAG
AAATCTGTTTTCAGAAACAAATCCTGCCTGCCGGTCCTTACTGGACCATTGAAATTGAAATTCCTTCTCC
CTGTCCAGGCTCACCCAAAGATCCTGCTCTTCCATTTTGAAATCTCTAGCACTTTCTCCACCTTTCTATA
TGCTTTAAGCCAGACACCCTGGCTAGATTGCACTGACCCCTGCTCCAGGGTAGAAGACCTCAGTCCCTTT
CTCAGAGTTCTGGGGGGAGGGGGGGTCTACCCTTCTGGTCTCTTTGGAAGGTTTTTATGAAGTTTGAGCT
TTTTGTCCCACCTCAGAACTCTGGGCTCTCCATCATGTAACCCAAATCTGAAGGCTTTCAGTGGTCTCCT
CTAATCTGATTTGCTTCATACCCTGGTTCTAGCTCAGGCCCTTCCATTCCTTGCTCTTGGCTGGGTTTCA
GCTCCGGCCTTGTCTCTTTCATGCCAGGGGCAAGGAAGGCTTGGTGTAGAATCCAAGCCTTAGCCTTTCT
GTTGCGGCTCTAATGTCCCAACAGAGTTTGTCCTCCATCTAAAAGTCAGCTCTTCACCCCAGTCACTTTC
ATGCCCTGGCCCAAGTCTTAGGCTCTCAGTCCCCTTGACATCCATCGCTGGCACTTTTACCATTCATTGA
CCAGGGGCCAGAGAGGGCTCTTCCCCCATGGTGGGGTGCTACCCACTGCCCTCCTAGGAGATGTTCTCCC
ATCCTGCAGGACAAGTAAAAGCACCCCCATAGCATATAGGCAGACTTGAGGGAGGAAGGGAGCAGGTGGG
GTGAGCAGGGTCTCCAATCCAGGGCCACTGGTCTGTCTGGAAACGTGAGGCTTGGAGCTGCTGCCCATCT
GTGCTCTGTGCTTCACCATCCACACGGTCCTCCCCTGGGAACTCCTTGCTACCACCTCTCATGCCTTCTG
GAAGGGGATGGAGTCTGACCTCTTGTCTCAGTCTCAGTGGAAAGCTTTCCTGGTCAAGGTCATGGCCTCA
GTGCCCTGCCTTCTGCATGATCCCAAAGCACAATGGTGAGTGAGGGGGAACTGCCTCCCTGCCTCTCACC
CTAAGTCAGGCAGAATGGCAGGCCTGTGCTGCCTCTGCACAGGAAGGTCTTCCTCCTCTGTATATCGGCT
TGAGGCCCGCTGTCCCCATCCTCAACTGAGAAATCTGGACCTCCCTTGGGCTGTTTTCTATAAAGTCTGC
AATAATCTCCGATGCTCTCTGCTCTTGTAAGTGGTTCTGTGTTTGTCCTACTGACCTTGGGGCATTGGTG
GGCGTGAAAGGTGACAAGAGGTGGCCATTTGGGGCAGTGGCCCTTATGCACTCTCTGGAGATGTGGGAAA
AAGAAACAGGCTGTGAGTACACATAGCAAGACTGAGGCTAGACACAGGGGGTGGGGGTGCTCTCCGTCAT
TCTCCAGCCTGCTTTTTAATGGTCTGAAACGGGCTTATCCACAGCCAGCAT

Figure 23B

*Murine Protein (mPL5)*
>gi|51829389|ref|XP_486328.1| PREDICTED: similar to hCG1820409 [Mus musculus]

MAPRAGQRGLWSPLPGLLLLAAALSRPAAPCPFQCYCFGSPRLMLRCASGAEL
RQPPRDVPPDARNLTIVGANLTVLRAAAFAGGGEGATDGVRLPLLTALRLTHN
NIEVVEDGAFDGLPSLAALDLSHNPLRALGYRAFRGLPALRSLQLNHALARGS
PGMLDALDAALAPLAELRLLGLVGNALSRLPLAALRLPRLEQLDARVNALAG
LGPDELSALERDGDLPQPRLLLADNPLSCGCTSRPLLAWLHNATERVPDARRL
RCASPRVLLDRPLIDLDEARLGCSDGDAHESGEGIDVAGPELEASYVFFGLVLA
LIGLIFLMVLYLNRRGIQRWMHNLREACRDQMEGYHYRYEQDADPRRAPAPA
APAGSRATSPGSGL

Figure 24

Murine amino acid alignment with murine 5T4, transmembrane region highlighted (*)

```
m5T4     : -MEGAGSRGPSAGDGRLRLARLALVLLGWVSASAPSSSVPSSSTSPAAFLASGSAQPPPPAERCPAPCECSEAAR-TVKCVN-RN :  81
m5T4para : MAPRAGQRG-------------------------LWSPLPG-------LLLLAAALSRPAAPCPFQCYCFGSPRLMLRCASGAE :  52

m5T4     : LLEVPADLPPYVRNLFLTGNQMTVLPAGAFARQPP-------LADLEALNLSGNHLKEVCAGAFEHLPGLRRLDLSHNPLTNLS : 158
m5T4para : LPQPPRDVPPDARNLTIVGANLTVLRAAAFAGGGEGATDGVRLPLLTALRLTHNNIEVVEDGAFDGLPSLAALDLSHNPLRALG : 136

m5T4     : AFAFAGSNASVSAPSPLEELILNHIVPPEDQRQNGSFEGMVAFEGMVAAALRSGLALRGLTRLELASNHFLFLPRDLLAQLPSL : 242
m5T4para : YRAFRG-------LPALRSLQLNHALARGSP-------------GMLDALDAA-------------------------LAPLAEL : 176

m5T4     : RYLDLRNNSLVSLTYVSFRNLTHLESLHLEDNALKVLHNSTLAEWHG---LAHVKVFLDNNPWVCDCYMADMVAWLK-ETEVVP : 322
m5T4para : RLLGLVGNALSRLPLPALR-LPRLEQLDARVNALAGLGPDELSALERDGDLPQPRLLLADNPLSCGCTSRPLLAWLHNATERVP : 259

                                                       *********************
m5T4     : LKARLTCAFPEKMRNRGLLDLNSSDLDCD-----------AVLPQSLQTSYVFLGIVLALIGAIFLLVLYLNRKGIKKWMHNIF : 395
m5T4para : DARRLRCASPRVLLDRPLIDLLEARLGCSDGDAHESGEGIDVAGPELEASYVFPGLVLALIGLIFLMVLYLNRRGIQRWMHNLR : 343

m5T4     : DACRDHMEGYHYRYEINADPF-----------LTNLSSNSDV : 426
m5T4para : EACRDQMEGYHYRYEQDADPRRAPAPAAPAGSRATSPGSGL : 384
```

Figure 25

5T4 paralogue Expressed Sequence Tags

*5T4 Paralogue mRNA*

>gi|26328418|dbj|AK032609.1| Mus musculus adult male olfactory brain cDNA, RIKEN full-length enriched library, clone:6430704N06 product:hypothetical Cysteine-rich flanking region, C-terminal containing protein, full insert sequence

```
GCAGCCCCGGGATGCTGGATGCACTGGACGCCGCTCTGGCCCCCCTGGCCGAGCTTCGCCTGCTGGGCTT
GGTAGGCAACGCGCTGAGCCGCCTGCCACTCGCCGCGCTGCGCCTGCCCCGCCTGGAGCAGCTGGATGCG
CGTGTCAACGCGCTGGCCGGCCTGGGCCCGGACGAGCTGAGCGCGCTTGAGCGCGATGGCGACCTGCCCC
AGCCGCGCCTGCTGCTGGCGGACAACCCACTGAGCTGTGGGTGCACCTCGCGCCCCCTGCTGGCCTGGCT
GCACAACGCCACCGAGCGCGTACCCGACGCGCGCCGCCTGCGCTGCGCTTCCCCGCGCGTACTGTTGGAC
CGGCCTCTGATAGACCTGGACGAGGCGCGACTAGGTTGCTCCGACGGCGATGCACACGAGAGCGGGGAAG
GGATAGACGTCGCCGGCCCGGAGTTGGAAGCCTCTTACGTCTTCTTCGGGCTGGTGCTGGCACTCATCGG
CCTCATCTTCCTCATGGTGCTCTACCTAAACCGCCGCGGCATCCAACGCTGGATGCACAATTTGCGCGAG
GCCTGCAGAGATCAGATGGAGGGCTACCACTACCGCTACGAGCAGGATGCAGACCCACGCCGCGCGCCTG
CTCCGGCCGCCCCTGCCGGCTCCCGGGCCACTTCTCCAGGCTCGGGTCTCTGAGCATCACCTACCTAGTG
GGAGGCTGTTCCTATCAGCTGATGACTTTACTTGGGCCATGCAGCCTTTCTCTGCCTGGCCTGGGCCCAG
GAGATAACACACTTACGAGTTTGGATCTCTGAGACCTTTGGATCAATCGTAGTATCTCTCCCATACAGAA
ATTCCAAGGTGTACTCTTTCCCTGGCCTTAGAGTTTCCAGATCAAAAACCCAGAAATCTGTTTTCAGAAA
CAAATCCTGCCTGCCGGTCCTTACTGGACCATTGAAATTGAAATTCCTTCTCCCTGTCCAGGCTCACCCA
AAGATCCTGCTCTTCCATTTTGAAATCTCTAGCACTTTCTCCACCTTTCTATATGCTTTAAGCCAGACAC
CCTGGCTAGATTGCACTGACCCCTGCTCCAGGGTAGAAGACCTCAGTCCCTTTCTCAGAGTTCTGGGGGG
AGGGGGGGTCTACCCTTCTGGTCTCTTTGGAAGGTTTTTATGAAGTTTGAGCTTTTTGTCCCACCTCAGA
ACTCTGGGCTCTCCATCATGTAACCCAAATCTGAAGGCTTTCAGTGGTCTCCTCTAATCTGATTTGCTTC
ATACCCTGGTTCTAGCTCAGGCCCTTCCATTCCTTGCTCTTGGCTGGGTTTCAGCTCCGGCCTTGTCTCT
TTCATGCCAGGGGCAAGGAAGGCTTGGTGTAGAATCCAAGCCTTAGCCTTTCTGTTGCGGCTCTAATGTC
CCAACAGAGTTTGTCCTCAATCTAAAAGTCAGCTCTTCACCCCAGTCACTTTCATGCCCTGGCCCAAGTC
TTAGGCTCTCAGTCCCCTTGACATCCATCGCTGGCACTTTTACCATTCATTGACCAGGGGCCAGAGAGGG
CTCTTCCCCCATGGTGGGGTGCTACCCACTGCCCTCCTAGGAGATGTTCTCCCATCCTGCAGGACAAGTA
AAAGCACCCCCATAGCATATAGGCAGACTTGAGGGAGGAAGGGAGCAGGTGGGGTGAGCAGGGTCTCCAA
TCCAGGGCCACTGGTCTGTCTGGAAACGTGAGGCTTGGAGCTGCTGCCCATCTGTGCTCTGTGCTTCACC
ATCCACACGGTCCTCCCCTGGGAACTCCTTGCTACCACCTCTCATGCCTTCTGGAAGGGGATGGAGTCTG
ACCTCTTGTCTCAGTCTCAGTGGAAAGCTTTCCTGGTCAAGGTCATGGCCTCAGTGCCCCTGCCTTCTGC
ATGATCCCAAAGCACAATGGTGAGTGAGGGGGAACTGCCTCCCTGCCTCTCACCCTAAGTCAGGCAGAAT
GGCAGGCCTGTGCTGCCTCTGCACAGGAAGGTCTTCCTCCTCTGTATATCGGCTTGAGGCCCGCTGTCCC
CATCCTCAACTGAGAAATCTGGACCTCCCTTGGGCTGTTTTCTATAAAGTCTGCAATAATCTCCGATGCT
CTCTGCTCTTGG
```

Figure 26

*mRNA translation (mPL5)*

>gi|26328419|dbj|BAC27948.1| unnamed protein product [Mus musculus]

```
SPGMLDALDAALAPLAELRLLGLVGNALSRLPLAALRLPRLEQLDARVNALAGLGPDELSALERDGDLPQ
PRLLLADNPLSCGCTSRPLLAWLHNATERVPDARRLRCASPRVLLDRPLIDLDEARLGCSDGDAHESGEG
IDVAGPELEASYVFFGLVLALIGLIFLMVLYLNRRGIQRWMHNLREACRDQMEGYHYRYEQDADPRRAPA
PAAPAGSRATSPGSGL
```

Figure 27

Murine amino acid alignment of EST with 5T4 paralogue, transmembrane region highlighted (*)

```
m5T4para : MAPRAGQRGLWSPLPGLLLLAAALSRPAAPCPFQCYCFGSPRLMLRCASGAELRQPPRDVPPDARNL :  67
EST      : ------------------------------------------------------------------- :   -

m5T4para : TIVGANLTVLRAAAFAGGGEGATDGVRLPLLTALRLTHNNIEVVEDGAFDGLPSLAALDLSHNPLRA : 134
EST      : ------------------------------------------------------------------- :   -

m5T4para : LGYRAFRGLPALRSLQLNHALARGSPGMLDALDAALAPLAELRLLGLVGNALSRLPLAALRLPRLEQ : 201
EST      : ------------------------SPGMLDALDAALAPLAELRLLGLVGNALSRLPLAALRLPRLEQ :  43

m5T4para : LDARVNALAGLGPDELSALERDGDLPQPRLLLADNPLSCGCTSRPLLAWLHNATERVPDARRLRCAS : 268
EST      : LDARVNALAGLGPDELSALERDGDLPQPRLLLADNPLSCGCTSRPLLAWLHNATERVPDARRLRCAS : 110

                                                     **********************
m5T4para : PRVLLDRPLIDLDEARLGCSDGDAHESGEGIDVAGPELEASYVFFGLVLALIGLIFLMVLYLNRRGI : 335
EST      : PRVLLDRPLIDLDEARLGCSDGDAHESGEGIDVAGPELEASYVFFGLVLALIGLIFLMVLYLNRRGI : 177

m5T4para : QRWMHNLREACRDQMEGYHYRYEQDADPRRAPAPAAPAGSRATSPGSGL : 384
EST      : QRWMHNLREACRDQMEGYHYRYEQDADPRRAPAPAAPAGSRATSPGSGL : 226
```

Human 5T4 paralogue RT-PCR 1 2 3

1 – genomic DNA (positive control)
2 – SHSY-5Y cDNA
3 – water (negative control)

B

```
>gi|169203011|ref|XM_001717487.1|
PREDICTED: Homo sapiens similar to hCG1820409 (LOC441617), mRNA Length=1020
GENE ID: 441617 LOC441617 | similar to hCG1820409 [Homo sapiens]
Score =  372 bits (201),  Expect = 4e-100
Identities = 206/208 (99%), Gaps = 1/208 (0%)
Strand=Plus/Plus

Query  78   GCGGCTTCGCTGCGCGGACAGCGGCGCCGACGCTCGCGGAGAGGAGGCGGAGGCCGCCGG  137
            ||||||||||||||||||||||||||||||||||||||||||||||||||||||||||||
Sbjct  714  GCGGCTTCGCTGCGCGGACAGCGGCGCCGACGCTCGCGGAGAGGAGGCGGAGGCCGCCGG  773

Query  138  CCCGGAGCTGGAAGCCTCCTACGTGTTCTTCGGGCTGGTGCTGGCACTCATCGGCCTCAT  197
            ||||||||||||||||||||||||||||||||||||||||||||||||||||||||||||
Sbjct  774  CCCGGAGCTGGAAGCCTCCTACGTGTTCTTCGGGCTGGTGCTGGCACTCATCGGCCTCAT  833

Query  198  CTTCCTCATGGTGCTCTACCTAAACCGCCGCGGCATCCAGCGCTGGATGCGCAACCTGCG  257
            ||||||||||||||||||||||||||||||||||||||||||||||||||||||||||||
Sbjct  834  CTTCCTCATGGTGCTCTACCTAAACCGCCGCGGCATCCAGCGCTGGATGCGCAACCTGCG  893

Query  258  CGAGGCGTGCCGGGACCAGATA-AGGGC  284
            ||||||||||||||||||||   |||||
Sbjct  894  CGAGGCGTGCCGGGACCAGATGGAGGGC  921
```

C 1 2 3 4

1 – genomic DNA (positive control)
2 – water (negative control)
3 – SHSY-5Y cDNA –RT
4 – SHSY-5Y cDNA +RT

Figure 29

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1

agctcttcgg taccctcgtc                                    20


<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2

gttgcggttc acgcactta                                     19


<210> SEQ ID NO 3
<211> LENGTH: 22
<212> TYPE: DNA
<213> ORGANISM: Artificial Sequence
```

<220> FEATURE:
<223> OTHER INFORMATION: Primer

<400> SEQUENCE: 3
ggcaatttgt aaaaatggga tt 22

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
aggttacata ccctccatat gacc 24

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
tccaaattcc ccagcaga 18

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
ctgaacccat cgctgcttag ac 22

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
caggacctgt ggccaagttc tt 22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
agctgaggat cacggctagc tt 22

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
gcggcttcgc tgcgcggac 19

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
atctggtccc ggcacgcctc g 21

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
aatggcaccc tggctgagtt g 21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
tctggggtcc gcattgattt c 21

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
catggagccc atctaccttg tg 22

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
gctgttgtcg aaggggtctc cg 22

<210> SEQ ID NO 15
<211> LENGTH: 21
<212> TYPE: PRT
<213> ORGANISM: Artificial Sequence
<220> FEATURE:
<223> OTHER INFORMATION: 5T4 Transmembrane Domain

<400> SEQUENCE: 15

```
Tyr Val Phe Leu Gly Ile Val Leu Ala Leu Ile Gly Ala Ile Phe Leu
 1               5                  10                  15

Leu Val Leu Tyr Leu
            20
```

<210> SEQ ID NO 16
<211> LENGTH: 21
<212> TYPE: PRT
<213> ORGANISM: Artificial Sequence
<220> FEATURE:
<223> OTHER INFORMATION: Transmembrane Domain

<400> SEQUENCE: 16

```
Tyr Val Phe Phe Gly Leu Val Leu Ala Leu Ile Gly Leu Ile Phe Leu
 1               5                  10                  15

Met Val Leu Tyr Leu
            20
```

<210> SEQ ID NO 17
<211> LENGTH: 21
<212> TYPE: PRT
<213> ORGANISM: Artificial Sequence
<220> FEATURE:
<223> OTHER INFORMATION: Transmembrane Domain

<400> SEQUENCE: 17

```
Ile Ile Ile Gly Cys Phe Val Ala Val Thr Leu Leu Ala Ala Ala Met
 1               5                  10                  15

Leu Ile Val Phe Tyr
            20
```

<210> SEQ ID NO 18
<211> LENGTH: 1822
<212> TYPE: DNA
<213> ORGANISM: Homo Sapiens

<400> SEQUENCE: 18

```
atgagtaact ttctcagccc acccctcatc ccttcctccg gtagtaggag cagctctaaa      60

gtcctcccca acccccgaat tctccctggt ggtgacccac ctgcctgctc tccgcagtcg     120

ggccccgccc cacacgtgct ggagaaggag gaggaaggac ccagcttaaa tgttgggggt     180

ggaggaggag gaaaaccaag tcggagcctc caggagccaa acttctcggc agcccggagg     240

ggcgggggcg gagaggatga agagaaagcg cagcagccga cagccctgat tctcgggagc     300

ctcccacccc gcctcccacg gcgaggaggg cgcggagact ccgctggggg cggaggacga     360

gaccgggagg cggggagggg ggaggcaaac cctgcccact cggctcggag cccggagcgg     420

ccgcggaagc cggaggccgg cgcgcagggc gagggcaccg ggggcggggg gctccgctcc     480

ccgtctgacc cctcttgccc ccggccagtc agccagtaag tgcggctcct cagactttcg     540

agacagcgaa cggaccgacc gggactgcca gccgctccgg gtcaaggact cgccccaccc     600

gtgcccccca ccaggcgctc ccaactcact ggtgagcgcg gcggcccggg cgctggatgc     660

gggggcggcc gcgatggccc cgcgcgcggg acagccgggg ctccaggggc tgctgctcgt     720

ggcggcggcg ctgagccagc ccgcggcacc ctgccccttc cagtgctact gcttcggcgg     780

ccccaagctg ctgctgcgct gcgcgtcggg agccgagctc cgccagcctc cgcgggacgt     840

gccgcccgac gcgcgcaacc tcaccatcgt aggcgccaac ctgacggtgc tgcgcgcggc     900

cgccttcgcc ggcggggacg gggacggcga ccaggcggcg ggcgtgcgcc tgccgctcct     960

gagcgcgctg cgcctcacgc acaaccacat cgaggtggtg gaggacggcg ccttcgacgg    1020

gctgcccagc ctggcggcgc tcgacctcag ccacaacccg ctgcgcgccc tgggcggcgg    1080

cgccttccgc gggctgcccg cgctgcgctc gctgcagctc aaccacgcgc tggtgcgcgg    1140

cggccccgcg ctgctggccg cgctggacgc tgcgctggca ccgctggccg agcttcgcct    1200

gctgggccta gcgggcaacg cgctgagccg tctgccgcca gccgccctgc gcctggcgcg    1260

cctggagcag ctggacgtgc gcctcaacgc gctggccggc ctggaccccg acgagctgcg    1320

cgcgctggag cgcgatggcg gcctccccgg gccgcgcctg ctgctcgccg acaacccccct    1380
```

```
gcgctgcggc tgtgccgcac gccccctgct ggcctggctg cgcaacgcca cggagcgcgt   1440

gcccgactcg cggcgcctgc gctgcgccgc cccgcgggcg ctgctagacc ggccgctact   1500

ggacctggac ggggcgcggc ttcgctgcgc ggacagcggc gccgacgctc gcggagagga   1560

ggcggaggcc gccggcccgg agctggaagc ctcctacgtg ttcttcgggc tggtgctggc   1620

actcatcggc ctcatcttcc tcatggtgct ctacctaaac cgccgcggca tccagcgctg   1680

gatgcgcaac ctgcgcgagg cgtgccggga ccagatggag ggctaccact accgctacga   1740

gcaggacgcc gacccgcgcc gcgcgcccgc gcccgccgcg cccgcgggct cccgcgccac   1800

ctccccgggc tcggggctct ga                                            1822
```

<210> SEQ ID NO 19
<211> LENGTH: 1737
<212> TYPE: DNA
<213> ORGANISM: Homo Sapiens

<400> SEQUENCE: 19

```
atgagtaact ttctcagccc accccctcatc ccttcctccg gtagtaggag cagctctaaa     60

gtcctcccca acccccgaat tctccctggt ggtgacccac ctgcctgctc tccgcagtcg    120

ggccccgccc cacacgtgct ggagaaggag gaggaaggac ccagcttaaa tgttgggggt    180

ggaggaggag gaaaaccaag tcggagcctc caggagccaa acttctcggc agcccggagg    240

ggcgggggcg gagaggatga agagaaagcg cagcagccga cagccctgat tctcgggagc    300

ctcccacccc gcctcccacg gcgaggaggg cgcggagact ccgctggggg cggaggacga    360

gaccgggagg cggggagggg ggaggcaaac cctgcccact cggctcggag cccggagcgg    420

ccgcggaagc cggaggccgg cgcgcaggac tttcgagaca gcgaacggac cgaccgggac    480

tgccagccgc tccgggtcaa ggactcgccc cacccgtgcc ccccaccagg cgctcccaac    540

tcactggtga gcgcggcggc ccgggcgctg gatgcggggg cggccgcgat ggccccgcgc    600

gcgggacagc cggggctcca ggggctgctg ctcgtggcgg cggcgctgag ccagcccgcg    660

gcaccctgcc ccttccagtg ctactgcttc ggcggcccca agctgctgct gcgctgcgcg    720

tcgggagccg agctccgcca gcctccgcgg gacgtgccgc ccgacgcgcg caacctcacc    780

atcgtaggcg ccaacctgac ggtgctgcgc gcggccgcct tcgccggcgg ggacggggac    840

ggcgaccagg cggcgggcgt gcgcctgccg ctcctgagcg cgctgcgcct cacgcacaac    900

cacatcgagg tggtggagga cggcgccttc gacgggctgc ccagcctggc ggcgctcgac    960

ctcagccaca acccgctgcg cgccctgggc ggcggcgcct tccgcgggct gcccgcgctg   1020

cgctcgctgc agctcaacca cgcgctggtg cgcggcggcc ccgcgctgct ggccgcgctg   1080

gacgctgcgc tggcaccgct ggccgagctt cgcctgctgg gcctagcggg caacgcgctg   1140

agccgtctgc cgccagccgc cctgcgcctg gcgcgcctgg agcagctgga cgtgcgcctc   1200

aacgcgctgg ccggcctgga ccccgacgag ctgcgcgcgc tggagcgcga tggcggcctc   1260

cccgggccgc gcctgctgct cgccgacaac cccctgcgct gcggctgtgc cgcacgcccc   1320

ctgctggcct ggctgcgcaa cgccacggag cgcgtgcccg actcgcggcg cctgcgctgc   1380

gccgccccgc gggcgctgct agaccggccg ctactggacc tggacggggc gcggcttcgc   1440

tgcgcggaca gcggcgccga cgctcgcgga gaggaggcgg aggccgccgg cccggagctg   1500

gaagcctcct acgtgttctt cgggctggtg ctggcactca tcggcctcat cttcctcatg   1560

gtgctctacc taaaccgccg cggcatccag cgctggatgc gcaacctgcg cgaggcgtgc   1620

cgggaccaga tggagggcta ccactaccgc tacgagcagg acgccgaccc gcgccgcgcg   1680
```

```
cccgcgcccg ccgcgcccgc gggctcccgc gccacctccc cgggctcggg gctctga      1737


<210> SEQ ID NO 20
<211> LENGTH: 382
<212> TYPE: PRT
<213> ORGANISM: Homo Sapiens

<400> SEQUENCE: 20

Met Ala Pro Arg Ala Gly Gln Pro Gly Leu Gln Gly Leu Leu Leu Val
 1               5                  10                  15

Ala Ala Ala Leu Ser Gln Pro Ala Ala Pro Cys Pro Phe Gln Cys Tyr
            20                  25                  30

Cys Phe Gly Gly Pro Lys Leu Leu Leu Arg Cys Ala Ser Gly Ala Glu
        35                  40                  45

Leu Arg Gln Pro Pro Arg Asp Val Pro Pro Asp Ala Arg Asn Leu Thr
    50                  55                  60

Ile Val Gly Ala Asn Leu Thr Val Leu Arg Ala Ala Ala Phe Ala Gly
65                  70                  75                  80

Gly Asp Gly Asp Gly Asp Gln Ala Ala Gly Val Arg Leu Pro Leu Leu
                85                  90                  95

Ser Ala Leu Arg Leu Thr His Asn His Ile Glu Val Val Glu Asp Gly
            100                 105                 110

Ala Phe Asp Gly Leu Pro Ser Leu Ala Ala Leu Asp Leu Ser His Asn
        115                 120                 125

Pro Leu Arg Ala Leu Gly Gly Gly Ala Phe Arg Gly Leu Pro Ala Leu
    130                 135                 140

Arg Ser Leu Gln Leu Asn His Ala Leu Val Arg Gly Gly Pro Ala Leu
145                 150                 155                 160

Leu Ala Ala Leu Asp Ala Ala Leu Ala Pro Leu Ala Glu Leu Arg Leu
                165                 170                 175

Leu Gly Leu Ala Gly Asn Ala Leu Ser Arg Leu Pro Pro Ala Ala Leu
            180                 185                 190

Arg Leu Ala Arg Leu Glu Gln Leu Asp Val Arg Leu Asn Ala Leu Ala
        195                 200                 205

Gly Leu Asp Pro Asp Glu Leu Arg Ala Leu Glu Arg Asp Gly Gly Leu
    210                 215                 220

Pro Gly Pro Arg Leu Leu Leu Ala Asp Asn Pro Leu Arg Cys Gly Cys
225                 230                 235                 240

Ala Ala Arg Pro Leu Leu Ala Trp Leu Arg Asn Ala Thr Glu Arg Val
                245                 250                 255

Pro Asp Ser Arg Arg Leu Arg Cys Ala Ala Pro Arg Ala Leu Leu Asp
            260                 265                 270

Arg Pro Leu Leu Asp Leu Asp Gly Ala Arg Leu Arg Cys Ala Asp Ser
        275                 280                 285

Gly Ala Asp Ala Arg Gly Glu Glu Ala Glu Ala Ala Gly Pro Glu Leu
    290                 295                 300

Glu Ala Ser Tyr Val Phe Phe Gly Leu Val Leu Ala Leu Ile Gly Leu
305                 310                 315                 320

Ile Phe Leu Met Val Leu Tyr Leu Asn Arg Arg Gly Ile Gln Arg Trp
                325                 330                 335

Met Arg Asn Leu Arg Glu Ala Cys Arg Asp Gln Met Glu Gly Tyr His
            340                 345                 350

Tyr Arg Tyr Glu Gln Asp Ala Asp Pro Arg Arg Ala Pro Ala Pro Ala
        355                 360                 365
```

```
Ala Pro Ala Gly Ser Arg Ala Thr Ser Pro Gly Ser Gly Leu
    370                 375                 380


<210> SEQ ID NO 21
<211> LENGTH: 10
<212> TYPE: RNA
<213> ORGANISM: Artificial Sequence
<220> FEATURE:
<223> OTHER INFORMATION: Kozak Sequence
<220> FEATURE:
<221> NAME/KEY: misc_feature
<222> LOCATION: 4
<223> OTHER INFORMATION: r = a or g

<400> SEQUENCE: 21

gccrccaugg                                                              10


<210> SEQ ID NO 22
<211> LENGTH: 10
<212> TYPE: RNA
<213> ORGANISM: Artificial Sequence
<220> FEATURE:
<223> OTHER INFORMATION: Synthetic Sequence

<400> SEQUENCE: 22

cggaaaauga                                                              10


<210> SEQ ID NO 23
<211> LENGTH: 10
<212> TYPE: RNA
<213> ORGANISM: Artificial Sequence
<220> FEATURE:
<223> OTHER INFORMATION: Synthetic Sequence

<400> SEQUENCE: 23

gccgcgaugg                                                              10


<210> SEQ ID NO 24
<211> LENGTH: 420
<212> TYPE: PRT
<213> ORGANISM: Homo Sapiens

<400> SEQUENCE: 24

Met Pro Gly Gly Cys Ser Arg Gly Pro Ala Ala Gly Asp Gly Arg Leu
 1               5                  10                  15

Arg Leu Ala Arg Leu Ala Leu Val Leu Leu Gly Trp Val Ser Ser Ser
            20                  25                  30

Ser Pro Thr Ser Ser Ala Ser Ser Phe Ser Ser Ser Ala Pro Phe Leu
        35                  40                  45

Ala Ser Ala Val Ser Ala Gln Pro Pro Leu Pro Asp Gln Cys Pro Ala
    50                  55                  60

Leu Cys Glu Cys Ser Glu Ala Ala Arg Thr Val Lys Cys Val Asn Arg
65                  70                  75                  80

Asn Leu Thr Glu Val Pro Thr Asp Leu Pro Ala Tyr Val Arg Asn Leu
                85                  90                  95

Phe Leu Thr Gly Asn Gln Leu Ala Val Leu Pro Ala Gly Ala Phe Ala
            100                 105                 110

Arg Arg Pro Pro Leu Ala Glu Leu Ala Ala Leu Asn Leu Ser Gly Ser
        115                 120                 125

Arg Leu Asp Glu Val Arg Ala Gly Ala Phe Glu His Leu Pro Ser Leu
    130                 135                 140

Arg Gln Leu Asp Leu Ser His Asn Pro Leu Ala Asp Leu Ser Pro Phe
145                 150                 155                 160
```

```
Ala Phe Ser Gly Ser Asn Ala Ser Val Ser Ala Pro Ser Pro Leu Val
                165                 170                 175

Glu Leu Ile Leu Asn His Ile Val Pro Pro Glu Asp Glu Arg Gln Asn
            180                 185                 190

Arg Ser Phe Glu Gly Met Val Val Ala Ala Leu Leu Ala Gly Arg Ala
        195                 200                 205

Leu Gln Gly Leu Arg Arg Leu Glu Leu Ala Ser Asn His Phe Leu Tyr
    210                 215                 220

Leu Pro Arg Asp Val Leu Ala Gln Leu Pro Ser Leu Arg His Leu Asp
225                 230                 235                 240

Leu Ser Asn Asn Ser Leu Val Ser Leu Thr Tyr Val Ser Phe Arg Asn
                245                 250                 255

Leu Thr His Leu Glu Ser Leu His Leu Glu Asp Asn Ala Leu Lys Val
            260                 265                 270

Leu His Asn Gly Thr Leu Ala Glu Leu Gln Gly Leu Pro His Ile Arg
        275                 280                 285

Val Phe Leu Asp Asn Asn Pro Trp Val Cys Asp Cys His Met Ala Asp
    290                 295                 300

Met Val Thr Trp Leu Lys Glu Thr Glu Val Val Gln Gly Lys Asp Arg
305                 310                 315                 320

Leu Thr Cys Ala Tyr Pro Glu Lys Met Arg Asn Arg Val Leu Leu Glu
                325                 330                 335

Leu Asn Ser Ala Asp Leu Asp Cys Asp Pro Ile Leu Pro Pro Ser Leu
            340                 345                 350

Gln Thr Ser Tyr Val Phe Leu Gly Ile Val Leu Ala Leu Ile Gly Ala
        355                 360                 365

Ile Phe Leu Leu Val Leu Tyr Leu Asn Arg Lys Gly Ile Lys Lys Trp
    370                 375                 380

Met His Asn Ile Arg Asp Ala Cys Arg Asp His Met Glu Gly Tyr His
385                 390                 395                 400

Tyr Arg Tyr Glu Ile Asn Ala Asp Pro Arg Leu Thr Asn Leu Ser Ser
                405                 410                 415

Asn Ser Asp Val
            420
```

<210> SEQ ID NO 25
<211> LENGTH: 5301
<212> TYPE: DNA
<213> ORGANISM: Mus musculus

<400> SEQUENCE: 25

```
agcatcaaac agacagacat ttattgaaat acctactgga cataatacac tggcaactcc      60

cgaagggaga gagcccttct tccagagaac acaacaattc cctcattcat acaacacaga     120

gaacacgact ccccttgcct aatgatgtcc gttcttctta agcttctctt ccccagctga     180

ggtgtttaac accagtcaat gaaagctgcc tgcaactatg taacccctct ccctcggaga     240

aggcagtcag cagcaatgag aaggcagcca ccatgaaaac cggagaggga gttttggcct     300

tggcagtggt ctacacttcc gtagggactg gaggcaggtc tccatgcagt taagtggggg     360

aagcaggctg ttctggtcac tcatgatttg agcacttgtg ctgtatgaga aaaggtacct     420

gtgacctcca aaggccaagg acatagtcca gagcaggaga gggccccgtc tgtacgcatt     480

cactttcaca agagtctgca agctgcccct ctaaggctgc agttgaacct gtgttggccc     540

agtgagtgaa cactcaagca ctttggtatg cttctgactc tatggacaca taccaggtta     600
```

-continued

```
cactcaaagc cgctatgtac acaggcacga atgtgcctgc atgtgtctat gtgagacaca    660
tttgtttgga actgctgtgt gcaagcctcc cgtgcacatg catgcacatc caagtaagaa    720
taaatttgat agaccacaca tgggcatgtg taagtctgtt tgtgtaaagt ttgccttttt    780
gtgtagaggc acacgtgtgt aaactcaggt ggccatgtat acagacatgt ccagctctaa    840
aagctactac tgtcatctgc tagcatctgg aggttatcat ggagacagga ctaggtcaat    900
atgagctgag ggagtccagc aagatcacca gcctggtcct tagtgttggt atttgcctga    960
gacccaggga atgcaggata tgcctcagaa agtggtttca atttgctggt cgatcttcta   1020
aatgcaactt cagggaagaa accaaccagt agtcttcagt tcaggagaaa gagactgact   1080
gatgcttatg gggaggaggg gagcctctat cccaaccagc tctgccaagt aagatactcg   1140
aatggcctgc agatcaaatg tcagcttctc caacctgaat aattcatgcc aagaccagga   1200
atgctccctc ctctggagtc tgtctcttta aatcaggtct tgagcttctc aattctggag   1260
gaaaaaaaaa gtaaataagt aaaacccaga aagaaagaaa aacaaaacaa aacaaaacaa   1320
gcctattaac agctcagccc ccacctcagc cctggatttt accacacccc caccctccac   1380
tacaaaatca gttcctgatt ttcctgctcc tagagccctc tccccaaccg gcacaccact   1440
caatattgac tggtagggca atttggaggg gaaggggcac agtatcctgg cagtactcag   1500
tgctggggcg gggtgggcaa gcaaagagct gaatcactcc acccaccgct ccctgagcct   1560
aggaggggcc cagcctgaaa ggtggaacca atgggagtgg tcttggcaga ggcagagcag   1620
cctgaattag ggcgcgggag atgtggggac agagggtgtt ttagaacata gaagagggtc   1680
gataaaagac tggacacaca ggacctgcag agttttagac acagcctaag ggaactgggt   1740
tcgcaaagga gacatccaag gctagggatt ttccaggctc gctcccttag cacagctcct   1800
ttccttgact acaagaagag taactttgtc agcccacccc tcagccctgc ctccttttct   1860
agggacagct ctaaactctc ccaccttctc tgggtgcaca gatccacctg ccaggtcagc   1920
cctgagggcc ccgccccacg tgtgcttcgg agggaggagg aaagaagctg cctaaacgaa   1980
gggggtgggg aaagaagcaa gtcagagctt ggggagccaa acttctcagc agctcgtgaa   2040
ctagagagca ggggagcaag agagcgcagc ggccctaagc ctgcatctcc ggagcctccc   2100
accccgcctc ccttgcgagg aggtgcggag actccgctgg gggcggagga ggcggccagg   2160
aggcggggag ggggaggcaa accctgccca ctcggctcgg agcccggaac agccgcggaa   2220
gtcggaggcc ggagcgcagg gcgacgaggg cagcgagggc ggggggctcc gctccccgcc   2280
tgacccctgt agcccccagc catcaaagtg aaggctcctc ggactttaca agctggagga   2340
cggaccggtc ggaactgtca gctgctccgg gtcaaggtct agcccacagc caccttcccg   2400
tgccaccccc atcccatcat ctccaaacgc tcccaattca ctggtgagcg ctgcgggccg   2460
ggggctggat gcggggacgg ccgcgatggc cccgcgcgcg ggacagcggg ggctctggag   2520
cccgctgcca gggctgctgc tcttggcggc ggcgctgagc cggcccgccg cgccctgtcc   2580
cttccagtgt tactgcttcg gcagcccccg gttaatgttg cgctgcgcgt cgggcgcgga   2640
gctccggcag ccgccccggg acgtgccacc cgacgcgcgc aacctcacca tcgtgggcgc   2700
caacctgacc gtgctgcgcg ccgcagcctt cgcgggaggg ggcgaggggg cgacggacgg   2760
cgtgcgccta ccgctcctta ccgcgctgcg cctcacacac aacaacatcg aggtagtaga   2820
ggacggtgcc ttcgacgggt tgcccagcct ggcggcactc gacctaagcc acaacccgct   2880
acgcgccctg ggctaccgcg cctttcgcgg gctgcctgcg ctgcgctcac tacagctcaa   2940
tcacgcgctg gctcgaggca gccccgggat gctggatgca ctggacgccg ctctggcccc   3000
```

```
cctggccgag cttcgcctgc tgggcttggt aggcaacgcg ctgagccgcc tgccactcgc   3060
cgcgctgcgc ctgccccgcc tggagcagct ggatgcgcgt gtcaacgcgc tggccggcct   3120
gggcccggac gagctgagcg cgcttgagcg cgatggcgac ctgccccagc cgcgcctgct   3180
gctggcggac aacccactga gctgtgggtg cacctcgcgc cccctgctgg cctggctgca   3240
caacgccacc gagcgcgtac ccgacgcgcg ccgcctgcgc tgcgcttccc cgcgcgtact   3300
gttggaccgg cctctgatag acctggacga ggcgcgacta ggttgctccg acggcgatgc   3360
acacgagagc ggggaaggga tagacgtcgc cggcccggag ttggaagcct cttacgtctt   3420
cttcgggctg gtgctggcac tcatcggcct catcttcctc atggtgctct acctaaaccg   3480
ccgcggcatc caacgctgga tgcacaattt gcgcgaggcc tgcagagatc agatggaggg   3540
ctaccactac cgctacgagc aggatgcaga cccacgccgc gcgcctgctc cggccgcccc   3600
tgccggctcc cgggccactt ctccaggctc gggtctctga gcatcacctc cctagtggga   3660
ggctgttcct atcagctgat gactttactt gggccatgca gcctttctct gcctggcctg   3720
ggccccggag ataacacact tacgagtttg gatctctgag acctttggat caatcgtagt   3780
atctctccca tacagaaatt ccaaggtgta ctctttccct ggccttagag tttccagatc   3840
aaaaacccag aaatctgttt tcagaaacaa atcctgcctg ccggtcctta ctggaccatt   3900
gaaattgaaa ttccttctcc ctgtccaggc tcacccaaag atcctgctct tccattttga   3960
aatctctagc actttctcca cctttctata tgctttaagc cagacaccct ggctagattg   4020
cactgacccc tgctccaggg tagaagacct cagtcccttt ctcagagttc tgggggggagg   4080
gggggtctac ccttctggtc tctttggaag gtttttatga agtttgagct tttgtcccca   4140
cctcagaact ctgggctctc catcatgtaa cccaaatctg aaggctttca gtggtctcct   4200
ctaatctgat ttgcttcata ccctggttct agctcaggcc cttccattcc ttgctcttgg   4260
ctgggtttca gctccggcct tgtctctttc atgccagggg caaggaaggc ttggtgtaga   4320
atccaagcct tagcctttct gttgcggctc taatgtccca acagagtttg tcctccatct   4380
aaaagtcagc tcttcacccc agtcactttc atgccctggc ccaagtctta ggctctcagt   4440
ccccttgaca tccatcgctg gcacttttac cattcattga ccaggggcca gagagggctc   4500
ttcccccatg gtggggtgct acccactgcc ctcctaggag atgttctccc atcctgcagg   4560
acaagtaaaa gcacccccat agcatatagg cagacttgag ggaggaaggg agcaggtggg   4620
gtgagcaggg tctccaatcc agggccactg gtctgtctgg aaacgtgagg cttggagctg   4680
ctgcccatct gtgctctgtg cttcaccatc cacacggtcc tcccctggga actccttgct   4740
accacctctc atgccttctg gaaggggatg gagtctgacc tcttgtctca gtctcagtgg   4800
aaagctttcc tggtcaaggt catggcctca gtgccctgcc ttctgcatga tcccaaagca   4860
caatggtgag tgagggggaa ctgcctccct gcctctcacc ctaagtcagg cagaatggca   4920
ggcctgtgct gcctctgcac aggaaggtct tcctcctctg tatatcggct tgaggcccgc   4980
tgtccccatc ctcaactgag aaatctggac ctcccttggg ctgttttcta taaagtctgc   5040
aataatctcc gatgctctct gctcttgtaa gtggttctgt gtttgtccta ctgaccttgg   5100
ggcattggtg ggcgtgaaag gtgacaagag gtggccattt ggggcagtgg cccttatgca   5160
ctctctggag atgtgggaaa aagaaacagg ctgtgagtac acatagcaag actgaggcta   5220
gacacagggg gtgggggtgc tctccgtcat tctccagcct gctttttaat ggtctgaaac   5280
gggcttatcc acagccagca t                                             5301
```

<210> SEQ ID NO 26

<211> LENGTH: 5301
<212> TYPE: DNA
<213> ORGANISM: Mus musculus

<400> SEQUENCE: 26
agcatcaaac agacagacat ttattgaaat acctactgga cataatacac tggcaactcc 60
cgaagggaga gagcccttct tccagagaac acaacaattc cctcattcat acaacacaga 120
gaacacgact ccccttgcct aatgatgtcc gttcttctta agcttctctt ccccagctga 180
ggtgtttaac accagtcaat gaaagctgcc tgcaactatg taacccctct ccctcggaga 240
aggcagtcag cagcaatgag aaggcagcca ccatgaaaac cggagaggga gttttggcct 300
tggcagtggt ctacacttcc gtagggactg gaggcaggtc tccatgcagt taagtggggg 360
aagcaggctg ttctggtcac tcatgatttg agcacttgtg ctgtatgaga aaaggtacct 420
gtgacctcca aaggccaagg acatagtcca gagcaggaga gggccccgtc tgtacgcatt 480
cactttcaca agagtctgca agctgcccct ctaaggctgc agttgaacct gtgttggccc 540
agtgagtgaa cactcaagca ctttggtatg cttctgactc tatggacaca taccaggtta 600
cactcaaagc cgctatgtac acaggcacga atgtgcctgc atgtgtctat gtgagacaca 660
tttgtttgga actgctgtgt gcaagcctcc cgtgcacatg catgcacatc caagtaagaa 720
taaatttgat agaccacaca tgggcatgtg taagtctgtt tgtgtaaagt ttgccttttt 780
gtgtagaggc acacgtgtgt aaactcaggt ggccatgtat acagacatgt ccagctctaa 840
aagctactac tgtcatctgc tagcatctgg aggttatcat ggagacagga ctaggtcaat 900
atgagctgag ggagtccagc aagatcacca gcctggtcct tagtgttggt atttgcctga 960
gacccaggga atgcaggata tgcctcagaa agtggtttca atttgctggt cgatcttcta 1020
aatgcaactt cagggaagaa accaaccagt agtcttcagt tcaggagaaa gagactgact 1080
gatgcttatg gggaggaggg gagcctctat cccaaccagc tctgccaagt aagatactcg 1140
aatggcctgc agatcaaatg tcagcttctc caacctgaat aattcatgcc aagaccagga 1200
atgctccctc ctctggagtc tgtctcttta aatcaggtct tgagcttctc aattctggag 1260
gaaaaaaaaa gtaaataagt aaaacccaga aagaaagaaa aacaaaacaa aacaaaacaa 1320
gcctattaac agctcagccc ccacctcagc cctggatttt accacacccc caccctccac 1380
tacaaaatca gttcctgatt ttcctgctcc tagagccctc tccccaaccg gcacaccact 1440
caatattgac tggtagggca atttggaggg gaaggggcac agtatcctgg cagtactcag 1500
tgctggggcg gggtgggcaa gcaaagagct gaatcactcc acccaccgct ccctgagcct 1560
aggaggggcc cagcctgaaa ggtggaacca atgggagtgg tcttggcaga ggcagagcag 1620
cctgaattag ggcgcgggag atgtggggac agagggtgtt ttagaacata gaagagggtc 1680
gataaaagac tggacacaca ggacctgcag agttttagac acagcctaag ggaactgggt 1740
tcgcaaagga gacatccaag gctagggatt ttccaggctc gctcccttag cacagctcct 1800
ttccttgact acaagaagag taactttgtc agcccacccc tcagccctgc ctccttttct 1860
agggacagct ctaaactctc ccaccttctc tgggtgcaca gatccacctg ccaggtcagc 1920
cctgagggcc ccgccccacg tgtgcttcgg agggaggagg aaagaagctg cctaaacgaa 1980
gggggtgggg aaagaagcaa gtcagagctt ggggagccaa acttctcagc agctcgtgaa 2040
ctagagagca ggggagcaag agagcgcagc ggccctaagc ctgcatctcc ggagcctccc 2100
accccgcctc ccttgcgagg aggtgcggag actccgctgg gggcggagga ggcggccagg 2160
aggcggggag ggggaggcaa accctgccca ctcggctcgg agcccggaac agccgcggaa 2220

```
gtcggaggcc ggagcgcagg gcgacgaggg cagcgagggc ggggggctcc gctccccgcc   2280

tgacccctgt agcccccagc catcaaagtg aaggctcctc ggactttaca agctggagga   2340

cggaccggtc ggaactgtca gctgctccgg gtcaaggtct agcccacagc caccttcccg   2400

tgccaccccc atcccatcat ctccaaacgc tcccaattca ctggtgagcg ctgcgggccg   2460

ggggctggat gcggggacgg ccgcgatggc cccgcgcgcg ggacagcggg ggctctggag   2520

cccgctgcca gggctgctgc tcttggcggc ggcgctgagc cggcccgccg cgccctgtcc   2580

cttccagtgt tactgcttcg gcagcccccg gttaatgttg cgctgcgcgt cgggcgcgga   2640

gctccggcag ccgccccggg acgtgccacc cgacgcgcgc aacctcacca tcgtgggcgc   2700

caacctgacc gtgctgcgcg ccgcagcctt cgcgggaggg ggcgaggggg cgacggacgg   2760

cgtgcgccta ccgctcctta ccgcgctgcg cctcacacac aacaacatcg aggtagtaga   2820

ggacggtgcc ttcgacgggt tgcccagcct ggcggcactc gacctaagcc acaacccgct   2880

acgcgccctg ggctaccgcg cctttcgcgg gctgcctgcg ctgcgctcac tacagctcaa   2940

tcacgcgctg gctcgaggca gccccgggat gctggatgca ctggacgccg ctctggcccc   3000

cctggccgag cttcgcctgc tgggcttggt aggcaacgcg ctgagccgcc tgccactcgc   3060

cgcgctgcgc ctgccccgcc tggagcagct ggatgcgcgt gtcaacgcgc tggccggcct   3120

gggcccggac gagctgagcg cgcttgagcg cgatggcgac ctgccccagc cgcgcctgct   3180

gctggcggac aacccactga gctgtgggtg cacctcgcgc cccctgctgg cctggctgca   3240

caacgccacc gagcgcgtac ccgacgcgcg ccgcctgcgc tgcgcttccc cgcgcgtact   3300

gttggaccgg cctctgatag acctggacga ggcgcgacta ggttgctccg acggcgatgc   3360

acacgagagc ggggaaggga tagacgtcgc cggcccggag ttggaagcct cttacgtctt   3420

cttcgggctg gtgctggcac tcatcggcct catcttcctc atggtgctct acctaaaccg   3480

ccgcggcatc caacgctgga tgcacaattt gcgcgaggcc tgcagagatc agatggaggg   3540

ctaccactac cgctacgagc aggatgcaga cccacgccgc gcgcctgctc cggccgcccc   3600

tgccggctcc cgggccactt ctccaggctc gggtctctga gcatcacctc cctagtggga   3660

ggctgttcct atcagctgat gactttactt gggccatgca gcctttctct gcctggcctg   3720

ggccccggag ataacacact tacgagtttg gatctctgag acctttggat caatcgtagt   3780

atctctccca tacagaaatt ccaaggtgta ctctttccct ggccttagag tttccagatc   3840

aaaaacccag aaatctgttt tcagaaacaa atcctgcctg ccggtcctta ctggaccatt   3900

gaaattgaaa ttccttctcc ctgtccaggc tcacccaaag atcctgctct tccattttga   3960

aatctctagc actttctcca cctttctata tgctttaagc cagacaccct ggctagattg   4020

cactgacccc tgctccaggg tagaagacct cagtcccttt ctcagagttc tgggggggagg   4080

gggggtctac ccttctggtc tctttggaag gtttttatga agtttgagct tttgtcccca   4140

cctcagaact ctgggctctc catcatgtaa cccaaatctg aaggctttca gtggtctcct   4200

ctaatctgat ttgcttcata ccctggttct agctcaggcc cttccattcc ttgctcttgg   4260

ctgggtttca gctccggcct tgtctctttc atgccagggg caaggaaggc ttggtgtaga   4320

atccaagcct tagcctttct gttgcggctc taatgtccca acagagtttg tcctccatct   4380

aaaagtcagc tcttcacccc agtcactttc atgccctggc ccaagtctta ggctctcagt   4440

ccccttgaca tccatcgctg gcacttttac cattcattga ccaggggcca gagagggctc   4500

ttcccccatg gtggggtgct acccactgcc ctcctaggag atgttctccc atcctgcagg   4560

acaagtaaaa gcacccccat agcatatagg cagacttgag ggaggaaggg agcaggtggg   4620
```

```
gtgagcaggg tctccaatcc agggccactg gtctgtctgg aaacgtgagg cttggagctg   4680

ctgcccatct gtgctctgtg cttcaccatc cacacggtcc tcccctggga actccttgct   4740

accacctctc atgccttctg gaaggggatg gagtctgacc tcttgtctca gtctcagtgg   4800

aaagctttcc tggtcaaggt catggcctca gtgccctgcc ttctgcatga tcccaaagca   4860

caatggtgag tgagggggaa ctgcctccct gcctctcacc ctaagtcagg cagaatggca   4920

ggcctgtgct gcctctgcac aggaaggtct tcctcctctg tatatcggct tgaggcccgc   4980

tgtccccatc ctcaactgag aaatctggac ctcccttggg ctgttttcta taaagtctgc   5040

aataatctcc gatgctctct gctcttgtaa gtggttctgt gtttgtccta ctgaccttgg   5100

ggcattggtg ggcgtgaaag gtgacaagag gtggccattt ggggcagtgg cccttatgca   5160

ctctctggag atgtgggaaa aagaaacagg ctgtgagtac acatagcaag actgaggcta   5220

gacacagggg gtgggggtgc tctccgtcat tctccagcct gctttttaat ggtctgaaac   5280

gggcttatcc acagccagca t                                             5301
```

```
<210> SEQ ID NO 27
<211> LENGTH: 384
<212> TYPE: PRT
<213> ORGANISM: Mus musculus

<400> SEQUENCE: 27

Met Ala Pro Arg Ala Gly Gln Arg Gly Leu Trp Ser Pro Leu Pro Gly
1               5                   10                  15

Leu Leu Leu Leu Ala Ala Ala Leu Ser Arg Pro Ala Ala Pro Cys Pro
            20                  25                  30

Phe Gln Cys Tyr Cys Phe Gly Ser Pro Arg Leu Met Leu Arg Cys Ala
        35                  40                  45

Ser Gly Ala Glu Leu Arg Gln Pro Pro Arg Asp Val Pro Pro Asp Ala
    50                  55                  60

Arg Asn Leu Thr Ile Val Gly Ala Asn Leu Thr Val Leu Arg Ala Ala
65                  70                  75                  80

Ala Phe Ala Gly Gly Gly Glu Gly Ala Thr Asp Gly Val Arg Leu Pro
                85                  90                  95

Leu Leu Thr Ala Leu Arg Leu Thr His Asn Asn Ile Glu Val Val Glu
            100                 105                 110

Asp Gly Ala Phe Asp Gly Leu Pro Ser Leu Ala Ala Leu Asp Leu Ser
        115                 120                 125

His Asn Pro Leu Arg Ala Leu Gly Tyr Arg Ala Phe Arg Gly Leu Pro
    130                 135                 140

Ala Leu Arg Ser Leu Gln Leu Asn His Ala Leu Ala Arg Gly Ser Pro
145                 150                 155                 160

Gly Met Leu Asp Ala Leu Asp Ala Ala Leu Ala Pro Leu Ala Glu Leu
                165                 170                 175

Arg Leu Leu Gly Leu Val Gly Asn Ala Leu Ser Arg Leu Pro Leu Ala
            180                 185                 190

Ala Leu Arg Leu Pro Arg Leu Glu Gln Leu Asp Ala Arg Val Asn Ala
        195                 200                 205

Leu Ala Gly Leu Gly Pro Asp Glu Leu Ser Ala Leu Glu Arg Asp Gly
    210                 215                 220

Asp Leu Pro Gln Pro Arg Leu Leu Leu Ala Asp Asn Pro Leu Ser Cys
225                 230                 235                 240

Gly Cys Thr Ser Arg Pro Leu Leu Ala Trp Leu His Asn Ala Thr Glu
                245                 250                 255
```

```
Arg Val Pro Asp Ala Arg Arg Leu Arg Cys Ala Ser Pro Arg Val Leu
            260                 265                 270

Leu Asp Arg Pro Leu Ile Asp Leu Asp Glu Ala Arg Leu Gly Cys Ser
        275                 280                 285

Asp Gly Asp Ala His Glu Ser Gly Glu Gly Ile Asp Val Ala Gly Pro
    290                 295                 300

Glu Leu Glu Ala Ser Tyr Val Phe Phe Gly Leu Val Leu Ala Leu Ile
305                 310                 315                 320

Gly Leu Ile Phe Leu Met Val Leu Tyr Leu Asn Arg Arg Gly Ile Gln
                325                 330                 335

Arg Trp Met His Asn Leu Arg Glu Ala Cys Arg Asp Gln Met Glu Gly
            340                 345                 350

Tyr His Tyr Arg Tyr Glu Gln Asp Ala Asp Pro Arg Arg Ala Pro Ala
        355                 360                 365

Pro Ala Ala Pro Ala Gly Ser Arg Ala Thr Ser Pro Gly Ser Gly Leu
    370                 375                 380


<210> SEQ ID NO 28
<211> LENGTH: 426
<212> TYPE: PRT
<213> ORGANISM: Mus musculus

<400> SEQUENCE: 28

Met Pro Gly Ala Gly Ser Arg Gly Pro Ser Ala Gly Asp Gly Arg Leu
 1               5                  10                  15

Arg Leu Ala Arg Leu Ala Leu Val Leu Leu Gly Trp Val Ser Ala Ser
            20                  25                  30

Ala Pro Ser Ser Ser Val Pro Ser Ser Ser Thr Ser Pro Ala Asp Phe
        35                  40                  45

Leu Ala Ser Gly Ser Ala Gln Pro Pro Pro Ala Glu Arg Cys Pro Ala
    50                  55                  60

Ala Cys Glu Cys Ser Glu Ala Ala Arg Thr Val Lys Cys Val Asn Arg
65                  70                  75                  80

Asn Leu Leu Glu Val Pro Ala Asp Leu Pro Pro Tyr Val Arg Asn Leu
                85                  90                  95

Phe Leu Thr Gly Asn Gln Met Thr Val Leu Pro Ala Gly Ala Phe Ala
            100                 105                 110

Arg Gln Pro Pro Leu Ala Asp Leu Glu Ala Leu Asn Leu Ser Gly Asn
        115                 120                 125

His Leu Lys Glu Val Cys Ala Gly Ala Phe Glu His Leu Pro Gly Leu
    130                 135                 140

Arg Arg Leu Asp Leu Ser His Asn Pro Leu Thr Asn Leu Ser Ala Phe
145                 150                 155                 160

Val Phe Ala Gly Ser Asn Ala Ser Val Ser Ala Pro Ser Pro Leu Glu
                165                 170                 175

Glu Leu Ile Leu Asn His Ile Val Pro Pro Glu Asp Gln Arg Gln Asn
            180                 185                 190

Gly Ser Phe Glu Gly Met Val Ala Phe Glu Gly Met Val Ala Ala Ala
        195                 200                 205

Leu Arg Ser Gly Leu Ala Leu Arg Gly Leu Thr Arg Leu Glu Leu Ala
    210                 215                 220

Ser Asn His Phe Leu Phe Leu Pro Arg Asp Leu Leu Ala Gln Leu Pro
225                 230                 235                 240

Ser Leu Arg Tyr Leu Asp Leu Arg Asn Asn Ser Leu Val Ser Leu Thr
                245                 250                 255
```

```
Tyr Ala Ser Phe Arg Asn Leu Thr His Leu Glu Ser Leu His Leu Glu
            260                 265                 270

Asp Asn Ala Leu Lys Val Leu His Asn Ser Thr Leu Ala Glu Trp Gln
        275                 280                 285

Gly Leu Ala His Val Lys Val Phe Leu Asp Asn Asn Pro Trp Val Cys
    290                 295                 300

Asp Cys Tyr Met Ala Asp Met Val Ala Trp Leu Lys Glu Thr Glu Val
305                 310                 315                 320

Val Pro Asp Lys Ala Arg Leu Thr Cys Ala Phe Pro Glu Lys Met Arg
                325                 330                 335

Asn Arg Gly Leu Leu Asp Leu Asn Ser Ser Asp Leu Asp Cys Asp Ala
            340                 345                 350

Val Leu Pro Gln Ser Leu Gln Thr Ser Tyr Val Phe Leu Gly Ile Val
        355                 360                 365

Leu Ala Leu Ile Gly Ala Ile Phe Leu Leu Val Leu Tyr Leu Asn Arg
    370                 375                 380

Lys Gly Ile Lys Lys Trp Met His Asn Ile Arg Asp Ala Cys Arg Asp
385                 390                 395                 400

His Met Glu Gly Tyr His Tyr Arg Tyr Glu Ile Asn Ala Asp Pro Arg
                405                 410                 415

Leu Thr Asn Leu Ser Ser Asn Ser Asp Val
            420                 425
```

<210> SEQ ID NO 29
<211> LENGTH: 2112
<212> TYPE: DNA
<213> ORGANISM: Mus musculus

<400> SEQUENCE: 29

```
gcagccccgg gatgctggat gcactggacg ccgctctggc ccccctggcc gagcttcgcc     60

tgctgggctt ggtaggcaac gcgctgagcc gcctgccact cgccgcgctg cgcctgcccc    120

gcctggagca gctggatgcg cgtgtcaacg cgctggccgg cctgggcccg gacgagctga    180

gcgcgcttga gcgcgatggc gacctgcccc agccgcgcct gctgctggcg gacaacccac    240

tgagctgtgg gtgcacctcg cgccccctgc tggcctggct gcacaacgcc accgagcgcg    300

tacccgacgc gcgccgcctg cgctgcgctt ccccgcgcgt actgttggac cggcctctga    360

tagacctgga cgaggcgcga ctaggttgct ccgacggcga tgcacacgag agcggggaag    420

ggatagacgt cgccggcccg gagttggaag cctcttacgt cttcttcggg ctggtgctgg    480

cactcatcgg cctcatcttc ctcatggtgc tctacctaaa ccgccgcggc atccaacgct    540

ggatgcacaa tttgcgcgag gcctgcagag atcagatgga gggctaccac taccgctacg    600

agcaggatgc agacccacgc cgcgcgcctg ctccggccgc ccctgccggc tcccgggcca    660

cttctccagg ctcgggtctc tgagcatcac ctacctagtg ggaggctgtt cctatcagct    720

gatgacttta cttgggccat gcagcctttc tctgcctggc ctgggcccag gagataacac    780

acttacgagt ttggatctct gagacctttg gatcaatcgt agtatctctc ccatacagaa    840

attccaaggt gtactctttc cctggcctta gagtttccag atcaaaaacc cagaaatctg    900

ttttcagaaa caaatcctgc ctgccggtcc ttactggacc attgaaattg aaattccttc    960

tccctgtcca ggctcaccca aagatcctgc tcttccattt tgaaatctct agcactttct   1020

ccacctttct atatgcttta agccagacac cctggctaga ttgcactgac ccctgctcca   1080

gggtagaaga cctcagtccc tttctcagag ttctgggggg aggggggtc tacccttctg   1140

gtctctttgg aaggttttta tgaagtttga gctttttgtc ccacctcaga actctgggct   1200
```

```
ctccatcatg taacccaaat ctgaaggctt tcagtggtct cctctaatct gatttgcttc   1260

ataccctggt tctagctcag gcccttccat tccttgctct tggctgggtt tcagctccgg   1320

ccttgtctct ttcatgccag gggcaaggaa ggcttggtgt agaatccaag ccttagcctt   1380

tctgttgcgg ctctaatgtc ccaacagagt ttgtcctcaa tctaaaagtc agctcttcac   1440

cccagtcact ttcatgccct ggcccaagtc ttaggctctc agtccccttg acatccatcg   1500

ctggcacttt taccattcat tgaccagggg ccagagaggg ctcttccccc atggtggggt   1560

gctacccact gccctcctag gagatgttct cccatcctgc aggacaagta aaagcacccc   1620

catagcatat aggcagactt gagggaggaa gggagcaggt ggggtgagca gggtctccaa   1680

tccagggcca ctggtctgtc tggaaacgtg aggcttggag ctgctgccca tctgtgctct   1740

gtgcttcacc atccacacgg tcctcccctg ggaactcctt gctaccacct ctcatgcctt   1800

ctggaagggg atggagtctg acctcttgtc tcagtctcag tggaaagctt tcctggtcaa   1860

ggtcatggcc tcagtgcccc tgccttctgc atgatcccaa agcacaatgg tgagtgaggg   1920

ggaactgcct ccctgcctct caccctaagt caggcagaat ggcaggcctg tgctgcctct   1980

gcacaggaag gtcttcctcc tctgtatatc ggcttgaggc ccgctgtccc catcctcaac   2040

tgagaaatct ggacctccct tgggctgttt tctataaagt ctgcaataat ctccgatgct   2100

ctctgctctt gg                                                       2112
```

```
<210> SEQ ID NO 30
<211> LENGTH: 226
<212> TYPE: PRT
<213> ORGANISM: Mus musculus

<400> SEQUENCE: 30

Ser Pro Gly Met Leu Asp Ala Leu Asp Ala Ala Leu Ala Pro Leu Ala
 1               5                  10                  15

Glu Leu Arg Leu Leu Gly Leu Val Gly Asn Ala Leu Ser Arg Leu Pro
            20                  25                  30

Leu Ala Ala Leu Arg Leu Pro Arg Leu Glu Gln Leu Asp Ala Arg Val
        35                  40                  45

Asn Ala Leu Ala Gly Leu Gly Pro Asp Glu Leu Ser Ala Leu Glu Arg
    50                  55                  60

Asp Gly Asp Leu Pro Gln Pro Arg Leu Leu Leu Ala Asp Asn Pro Leu
65                  70                  75                  80

Ser Cys Gly Cys Thr Ser Arg Pro Leu Leu Ala Trp Leu His Asn Ala
                85                  90                  95

Thr Glu Arg Val Pro Asp Ala Arg Arg Leu Arg Cys Ala Ser Pro Arg
            100                 105                 110

Val Leu Leu Asp Arg Pro Leu Ile Asp Leu Asp Glu Ala Arg Leu Gly
        115                 120                 125

Cys Ser Asp Gly Asp Ala His Glu Ser Gly Glu Gly Ile Asp Val Ala
    130                 135                 140

Gly Pro Glu Leu Glu Ala Ser Tyr Val Phe Phe Gly Leu Val Leu Ala
145                 150                 155                 160

Leu Ile Gly Leu Ile Phe Leu Met Val Leu Tyr Leu Asn Arg Arg Gly
                165                 170                 175

Ile Gln Arg Trp Met His Asn Leu Arg Glu Ala Cys Arg Asp Gln Met
            180                 185                 190

Glu Gly Tyr His Tyr Arg Tyr Glu Gln Asp Ala Asp Pro Arg Arg Ala
        195                 200                 205
```

-continued

```
Pro Ala Pro Ala Ala Pro Ala Gly Ser Arg Ala Thr Ser Pro Gly Ser
    210                 215                 220

Gly Leu
225


<210> SEQ ID NO 31
<211> LENGTH: 208
<212> TYPE: DNA
<213> ORGANISM: Homo sapiens

<400> SEQUENCE: 31

gcggcttcgc tgcgcggaca gcggcgccga cgctcgcgga gaggaggcgg aggccgccgg     60

cccggagctg gaagcctcct acgtgttctt cgggctggtg ctggcactca tcggcctcat    120

cttcctcatg gtgctctacc taaaccgccg cggcatccag cgctggatgc gcaacctgcg    180

cgaggcgtgc cgggaccaga tggagggc                                       208


<210> SEQ ID NO 32
<211> LENGTH: 207
<212> TYPE: DNA
<213> ORGANISM: Homo sapiens

<400> SEQUENCE: 32

gcggcttcgc tgcgcggaca gcggcgccga cgctcgcgga gaggaggcgg aggccgccgg     60

cccggagctg gaagcctcct acgtgttctt cgggctggtg ctggcactca tcggcctcat    120

cttcctcatg gtgctctacc taaaccgccg cggcatccag cgctggatgc gcaacctgcg    180

cgaggcgtgc cgggaccaga taagggc                                        207
```

INHIBITION OF THE INTERACTION BETWEEN 5T4 ONCOFOETAL GLYCOPROTEINS AND CXC CHEMOKINE RECEPTORS AS A METHOD OF IDENTIFYING CHEMOTAXIS INHIBITORS

FIELD OF THE INVENTION

The present invention relates to methods, particularly methods of screening test agents, methods of treatment and methods of patient stratification, involving a glycoprotein that is involved in cancer metastasis, and to products for use in such methods.

BACKGROUND TO THE INVENTION

Treatment of cancer metastasis, the spread and growth of tumour cells to distant sites, presents a significant challenge despite the identification of a number of mediators that are implicated in the process. Indeed, spread of cancer to distant sites is almost universally associated with poor prognosis and, in many cases, resistance to effective treatment. For example, in childhood acute lymphoblastic leukaemia (ALL) certain high-risk cytogenetic subtypes not only have higher relapse rate but are also more likely to relapse in extramedullary sites such as the CNS. Methods for identification of tumour subtypes that are prone to spread and/or relapse are currently sub-optimal. In the case of ALL, current methods for establishing a prognosis involve, for example, cytogenetic analysis (e.g. FISH) requiring specialist knowledge and expertise, particularly for interpretation of results.

Epithelial-mesenchymal transition (EMT) occurs during embryonic development and is believed to be important for the metastatic spread of epithelial tumours [17]. It is characterized by an E- to N-cadherin switch, increased vimentin expression, upregulation of E-cadherin repressor molecules and increased gelatinase activity and motility [18].

CD26 is a cell surface protease which cleaves the chemokine CXCL12 [19]. CXCL12 has been shown to regulate many biological processes but also plays an important role in tumourigenesis [20, 21]. CXCL12 binds to the widely expressed cell surface chemokine receptor CXCR4 [22, 23] and to the recently identified receptor CXCR7/RDC1 [24] leading to a signalling cascade resulting in downstream phosphorylation of proteins such as ERK1/2 and AKT [25, 26]. Like CXCL12, CXCR4 expression has also been associated with tumourigenesis in many cancers including breast, ovarian, renal, prostate, and neuroblastoma [20-22]. These CXCR4-expressing tumours preferentially spread to tissues that highly express CXCL12, including brain, lung, liver, lymph nodes and bone marrow [20-22].

The chemokine receptor CXCR6, which binds the ligand CXCL16 is upregulated in certain tumours, for example human prostate cancer, and increases the metastatic progression of these cells by enhancing CXCL16 mediated chemotaxis [51].

5T4 oncofetal glycoprotein was discovered while searching for molecules with invasive properties likely to be shared by trophoblast and cancer cells [1]. It is expressed by many different carcinomas while showing only low levels in some normal tissues [2]. 5T4 expression has been shown to influence adhesion, cytoskeletal organization and motility, properties [3-5] which might account for its association with poorer clinical outcome in some cancers [6-9]. The ≈72 kDa transmembrane molecule has an N-glycosylated extracellular domain with two leucine rich repeat (LRR) regions with associated N and C terminal flanking regions separated by a hydrophilic sequence as well as a short cytoplasmic region [10, 11]. Leucine rich repeats are found in proteins with diverse functions and are frequently associated with protein-protein interaction [12]. It has recently been shown that upregulation of 5T4 expression is a marker of loss of pluripotency in the early differentiation of human and murine embryonic stem cells [13, 14] and forms an integrated component of an EMT [15-16].

Despite advances in the treatment of many cancers, provision of therapeutic agents and treatment strategies for preventing or limiting the spread of cancer cells is currently hampered by an incomplete picture of the mechanistic details of metastasis. Accordingly, there remains a need for methods to identify and utilise agents that inhibit the spread of cancer cells, and methods to identify tumours at high risk of metastasis.

DISCLOSURE OF THE INVENTION

The present inventors have now found that 5T4 interacts with CXCR4 in the cell membrane to form a complex, and that the 5T4 transmembrane region is involved in the promotion of CXCR4 membrane expression and chemotactic response. CXCR4 mediates the CXCL12-directed migration of many cancer cells to metastatic sites through the promotion of angiogenesis and migration of tumour cells, including but not limited to those originating in breast, lung, ovarian, renal, prostate, gastric, oral, cervix, non-small cell lung carcinoma, (NSCLC), colorectal, glioma and neuroblastoma tissue [20-22]; these being tumour types which also express 5T4 glycoprotein [2, 9, 45]. Therefore, interference with the co-expression and/or membrane localisation of 5T4 and CXCR4 in a tumour cell and/or targeting a complex comprising 5T4 and CXCR4 with, e.g. antibody-delivered drugs, represent significant new approaches to targeting and treating metastasis. Furthermore, co-expression and co-localisation of 5T4 and CXCR6, but not CXCR3 or CXCR7, described herein, indicates that the 5T4 interaction with CXCR4 or CXCR6 may represent a transmembrane interaction common to a subset of the CXC chemokine receptor subfamily. Therefore, interference with the co-expression of 5T4 and a CXC chemokine receptor (such as CXCR4 or CXCR6) in a tumour cell and/or targeting a putative complex comprising 5T4 and a CXC chemokine receptor (such as CXCR4 or CXCR6) with, e.g. antibody-delivered drugs, may likewise be useful for targeting and treating a chemotaxis-related condition, e.g. cancer spread or inflammation. Moreover, the discovery of elevated levels of 5T4 expression in a subset of high risk human pre-B ALL indicates that 5T4 expression and/or cell surface localisation of 5T4 may be used as a marker for certain cancer subtypes that are prone to spread, relapse and/or which may fail to respond to conventional leukaemia therapy.

Accordingly, in a first aspect the present invention provides a method for identifying a chemotaxis inhibitor, comprising:

providing a 5T4 polypeptide, a CXC chemokine receptor polypeptide and a test agent under conditions in which, in the absence of the test agent, the 5T4 polypeptide and the CXC chemokine receptor polypeptide are able to interact; and determining whether the test agent inhibits the interaction between the 5T4 polypeptide and the CXC chemokine receptor polypeptide, wherein inhibition of said interaction indicates that the test agent is a chemotaxis inhibitor. As used herein in connection with this and other aspects of the invention, interaction between the 5T4 polypeptide and the CXC chemokine receptor polypeptide may be direct (e.g. wherein the two polypeptides physically contact in a protein-protein interaction) or indirect (e.g. wherein the 5T4 polypeptide and the CXC chemokine receptor polypeptide each contribute to a complex which may comprise other polypeptides, including one or more intermediary polypeptides). Preferably, determining whether the test agent inhibits the interaction between the 5T4 polypeptide and the CXC chemokine receptor polypeptide comprises detecting a complex comprising the 5T4 polypeptide and the CXC chemokine receptor polypeptide, and wherein a decrease in the level of said complex and/or a decrease in the formation of said complex in the presence of the test agent, as compared with in the absence of the test agent, indicates that the test agent is a chemotaxis inhibitor. The test agent may interfere with the physical interaction of the 5T4 polypeptide and the CXC chemokine receptor polypeptide, e.g. by binding to a site on the 5T4 polypeptide that is involved in the binding of the 5T4 polypeptide to the CXC chemokine receptor polypeptide or by binding to a site on the CXC chemokine receptor polypeptide that is involved in the binding of the CXC chemokine receptor polypeptide to the 5T4 polypeptide. Alternatively, the test agent may bind to a site on the 5T4 polypeptide or the CXC chemokine receptor polypeptide that is remote from the sites involved in the physical interaction between the two polypeptides. For example, the test agent may act as an allosteric inhibitor which alters or stabilises the conformation of the 5T4 polypeptide or the CXC chemokine receptor polypeptide such that interaction between the two polypeptides is prevented or reduced. The CXC chemokine receptor polypeptide may be a CXC chemokine receptor subfamily member other than CXCR3 and CXCR7. Preferably, the CXC chemokine receptor polypeptide is a CXCR4 or CXCR6 polypeptide as defined further herein.

The present inventors have identified a complex of approximately 130 kDa (as determined by PAGE) comprising the 5T4 polypeptide and a CXC chemokine receptor polypeptide (in particular the CXCR4 protein). The complex has been found to be stable in the cell membrane and was able to remain intact following non-ionic detergent solubilisation and unreduced PAGE. Accordingly, in some cases the test agent may inhibit the interaction between the 5T4 polypeptide and the CXC chemokine receptor polypeptide by inhibiting formation of the complex, destabilising the complex or enhancing the break-up of the complex.

The method of this and other aspects of the invention may be carried out in the form of a cell-free screening assay, e.g., in which the 5T4 polypeptide, the CXC chemokine receptor polypeptide and the test agent are provided in a membrane preparation or in an aqueous preparation. Preferably, the method is carried out in the form of a cell-based assay, wherein the 5T4 polypeptide and the CXC chemokine receptor polypeptide are expressed by a cell and the cell is contacted with the test agent. The method of this and other aspects of the invention may be carried out in vitro. However, in some cases the method of the invention may comprise one or more additional in vivo steps.

Proper functioning of CXCR4, in particular CXCR4 recognition of the ligand CXCL12 and consequent chemotaxis of the cell, is believed to require the presence of CXCR4 at the cell surface. The results described further herein indicate that 5T4 interacts with CXCR4 so as to promote the cell surface expression of CXCR4.

Furthermore, studies in MEFs and mES cells suggest that CXCR6 expression at the cell surface also depends on 5T4 expression at the cell surface and may be required for response to the CXCR6 ligand, CXCL16. Accordingly, in some cases of the method of this aspect of the invention determining whether the test agent inhibits the interaction between the 5T4 polypeptide and the CXC chemokine receptor polypeptide comprises detecting cell surface expression of the CXC chemokine receptor polypeptide and/or a complex comprising the CXC chemokine receptor polypeptide (e.g. a complex comprising the CXC chemokine receptor polypeptide and the 5T4 polypeptide and optionally one or more other components), wherein a decrease in the cell surface expression of the CXC chemokine receptor polypeptide and/or said complex in the presence of the test agent, as compared with in the absence of the test agent, indicates that the test agent is a chemotaxis inhibitor. Cell surface expression of the CXC chemokine receptor polypeptide and/or a complex comprising the CXC chemokine receptor polypeptide may be conveniently detected using an antibody or fragment thereof that is capable of binding to the CXC chemokine receptor polypeptide and/or which is capable of binding (e.g. selectively binding) said complex. Preferably, the antibody is labelled or is contacted with a secondary antibody that is labelled or comprises a moiety capable of generating a detectable signal. Localisation of the CXC chemokine receptor polypeptide and/or said complex at the cell surface may be determined using a cell imaging technique, e.g. fluorescence labelling and fluorescence microscopy as is known in the art. A preferred technique for detecting cell surface localisation of the CXC chemokine receptor polypeptide and/or said complex is flow cytometry, particularly fluorescence-activated cell sorting ("FACS"). Preferably, FACS is used to determine presence of said complex at the cell surface, e.g. using a fluorescent labelled antibody that selectively binds said complex.

In some cases the method of this aspect of the invention further comprises assessing CXC chemokine receptor-mediated chemotaxis of the cell in the presence of the test agent, as compared with in the absence of the test agent. As noted above, 5T4 promotes cell surface expression of CXCR4, which is believed to be necessary for CXCL12-CXCR4-mediated chemotaxis. Likewise, it is believed that 5T4 promotes cell surface expression of CXCR6, which is believed to be necessary for CXCL16-CXCR6-mediated chemotaxis. Therefore, a further step of assessing CXC chemokine receptor-mediated chemotaxis (e.g. chemotaxis towards an appropriate CXC ligand, such as CXCL12 for CXCR4 or CXCL16 for CXCR6) provides a confirmation of the functional inhibition of chemotaxis by the test agent. Chemotaxis may be assessed using a cellular motility assay as is known in the art. For example, a cell that expresses 5T4 and CXC chemokine receptor may be contacted with the test agent before or after exposure to a CXCR ligand (e.g. CXCL12 or CXCL16 for CXCR4 or CXCR6, respectively). The chemotaxis response of the cell may be quantified, e.g., by measuring migration of the cell across a transwell. Preferably, the method comprises assessing chemotaxis of a plurality of cells.

Activation of CXC chemokine receptors by their ligands also results in functional consequences other than chemotaxis, such as cell proliferation and cell survival. Upon ligand binding the chemokine receptor CXCR4 is capable of eliciting multiple cellular functions aside from chemotaxis. For example, the overexpression of CXCR4 in pituitary adenomas contributes to pituitary cell proliferation and possibly adenoma development [54]. Signals from the CXCR4 receptor have also been implicated in the regulation of the Bcl-2/Bax ratio to promote dendritic cell survival in the thymus [55].

Accordingly, in some cases the method of this aspect of the invention further comprises assessing CXC chemokine receptor-mediated cell proliferation and/or cell survival in the presence of the test agent, as compared with in the absence of the test agent.

In accordance with the method of this and other aspects of the invention the cell is preferably a cancer cell. Particularly preferred cells are tumour cells (primary tumours or derived cell lines) that are 5T4 +ve and CXC chemokine receptor +ve (e.g. CXCR4 +ve and/or CXCR6 +ve). The cell may be selected from a cancer cell of breast, ovarian, renal, prostate, gastric, oral, cervix, NSCLC, colorectal, glioma, neuroblastoma or acute lymphoblastic leukaemia origin (particularly a high risk cytogenetic subtype of pre-B ALL). Alternatively, the cell may be an embryonic stem cell. Particularly preferred cell types are: SHSY-5Y neuroblastoma, E14TG2a [29], MCF-7, MDA-MB-231, JEG-3, SupB15, SD1, REH, Nalm-6, Tom-1, SKOV3, CAOV3, OVCAR3 and PA1. The cell may be obtained from or derived from a 5T4 null (e.g. knockout) rodent, a 5T4 wild-type rodent or a rodent which is heterozygous for 5T4 knockout (e.g. a 5T4 null mouse, WT mouse or a mouse heterozygous for 5T4). Preferably, a cell obtained or derived from a 5T4 knockout rodent is an embryonic stem cell or an embryonic fibroblast.

Chemotaxis, particularly chemotaxis in response to CXCL12 or CXCL16, is an important feature of metastasis. Therefore, an inhibitor of the interaction between 5T4 and a CXC chemokine receptor may exhibit anti-cancer therapeutic activity, particularly inhibition or prevention of metastasis (e.g. spread of 5T4 +ve and CXCR4 +ve cancer cells to CXCL12-expressing sites or spread of 5T4 +ve and CXCR6 +ve cancer cells to CXCL16-expressing sites). Accordingly, the method of this aspect of the invention may further comprise an in vivo step of assessing metastasis of a cancer in a non-human animal model to which the test agent has been administered, as compared with metastasis of a cancer in a control non-human animal model to which the test agent has not been administered. The non-human animal model may be a mammalian laboratory animal species such as a rodent (e.g. mouse, rat), rabbit, cat, dog or non-human primate. In some cases the mouse may be a 5T4 null mouse (e.g. 5T4 KO mouse), which may be useful, for example, as a negative control. In some cases a 5T4-ve animal (e.g. a 5T4 null mouse) may be the recipient of a 5T4 positive and CXC chemokine receptor positive tumour (e.g. a 5T4 +ve and CXCR4 +ve tumour), e.g. an implanted tumour. In this way the effect of drug treatment may be assessed in the absence of any influence through normal tissue 5T4/CXCR4 expression.

The cancer preferably comprises 5T4 +ve and CXC chemokine receptor +ve cells (e.g. CXCR4 +ve and/or CXCR6 +ve cells). Preferably the cancer is cancer of breast, ovarian, renal, prostate, gastric, oral, cervix, NSCLC, colorectal, glioma neuroblastoma or acute lymphoblastic leukaemia origin (particularly a high risk cytogenetic subtype of pre-B ALL).

As described further herein, the present inventors have found that the transmembrane domain of the 5T4 polypeptide is largely or entirely responsible for the promotion of cell surface expression of CXCR4 by 5T4. Accordingly, in some cases of the method of this and other aspects of the invention the 5T4 polypeptide comprises at least a transmembrane domain and, optionally, an extracellular domain and/or a cytoplasmic domain. However, in many cases a therapeutic agent which is directed to a cell surface target is preferred because this avoids certain difficulties associated with penetrating the cell membrane, particularly when the agent comprises a bulky peptide or antibody. For this reason screening assays that are designed to detect promising agents directed to a cell surface targets are often preferred. Accordingly, in preferred cases of the method of this and other aspects of the invention the 5T4 polypeptide comprises at least a transmembrane domain and an extracellular domain and optionally a cytoplasmic domain.

In accordance with the method of this and other aspects of the invention the 5T4 polypeptide may comprise at least the transmembrane domain, and optionally the extracellular domain and/or a cytoplasmic domain, of:

(i) the human 5T4 polypeptide having the amino acid sequence disclosed at NCBI Accession No: NP_006661, GI: 5729718;
(ii) a variant (such as a splice variant), paralogue, orthologue or derivative of (i) having at least 70%, at least 80%, at least 90%, at least 95% or at least 99% amino acid sequence identity to (i) calculated over the full-length of (i) or calculated over at least the transmembrane domain of (i);
(iii) the human 5T4 paralogue polypeptide having the amino acid sequence shown in FIG. 20A at;
(iv) the mouse 5T4 polypeptide having the amino acid sequence disclosed at NCBI Accession No: NP_035757, GI: 31543887;
(v) a variant (such as a splice variant), paralogue, orthologue or derivative of any of (iii) or (iv) having at least 70%, at least 80%, at least 90%, at least 95% or at least 99% amino acid sequence identity to any of (iii) or (iv) calculated over the full-length of any of (iii) or (iv) or calculated over at least the transmembrane domain of (iii) or (iv);
(vi) the mouse 5T4 paralogue polypeptide having the predicted amino acid sequence disclosed at NCBI Accession No: XP_486328, GI: 51829389;
(vii) a rat paralogue having the amino acid sequence disclosed at NCBI Accession No: XP00101215, GI: 109459106; or
(viii) a fragment of any one of (i)-(vii) having at least 20, at least 30, at least 50, at least 100 or at least 200 amino acids. Preferably, said fragment (viii) comprises a transmembrane domain. Preferably, the 5T4 polypeptide comprises a transmembrane domain having the amino acid sequence of the human 5T4 transmembrane domain shown in FIG. 17*a*. In accordance with the method of this and other aspects of the invention, a further preferred 5T4 polypeptide comprises:

the rat 5T4 polypeptide having the amino acid sequence disclosed at NCBI Accession No: AAH87011, GI: 56268820;

a variant (such as a splice variant), paralogue, orthologue or derivative of said rat 5T4 polypeptide, having at least 70%, at least 80%, at least 90%, at least 95% or at least 99% amino acid sequence identity to said rat 5T4 polypeptide calculated over the full-length of said rat 5T4 polypeptide or calculated over at least the transmembrane domain of said rat 5T4 polypeptide; or a fragment of any one of said rat 5T4 polypeptide or said variant, paralogue, orthologue or derivative, having at least 20, at least 30, at least 50, at least 100 or at least 200 amino acids.

The CXC chemokine receptor subfamily is currently considered to comprise CXCR1, CXCR2, CXCR3, CXCR4, CXCR5, CXCR6 and CXCR7. In accordance with the method of this and other aspects of the invention the CXC chemokine receptor polypeptide may be a CXC chemokine receptor subfamily member other than CXCR3 and CXCR7. Preferably, the CXC chemokine receptor polypeptide is CXCR4 polypeptide or a CXCR6 polypeptide.

The CXCR4 polypeptide may have the amino acid sequence of:

(i) the human CXCR4 polypeptide having the amino acid sequence disclosed at NCBI Accession No: CAA12166, GI: 3059120;

(ii) a variant (such as a splice variant), paralogue, orthologue or derivative of (i) having at least 70%, at least 80%, at least 90%, at least 95% or at least 99% amino acid sequence identity to (i) calculated over the full-length of (i);

(iii) the mouse CXCR4 polypeptide having the amino acid sequence disclosed at NCBI Accession No: AAH98322, GI: 68226707;

(iv) a variant (such as a splice variant), paralogue, orthologue or derivative of (iii) having at least 70%, at least 80%, at least 90%, at least 95% or at least 99% amino acid sequence identity to (iii) calculated over the full-length of (iii);

(v) the rat CXCR4 polypeptide having the amino acid sequence disclosed at NCBI Accession No: AAL47855, GI: 17902281;

(vi) a variant (such as a splice variant), paralogue, orthologue or derivative of (v) having at least 70%, at least 80%, at least 90%, at least 95% or at least 99% amino acid sequence identity to (v) calculated over the full-length of (v);

(vii) a fragment of any one of (i)-(vi) having at least 100, at least 200, at least 250, or at least 300 amino acids. Preferably, said fragment (vii) comprises a CXCL12-binding domain.

The CXCR6 polypeptide may have the amino acid sequence of:

(i) the human CXCR6 polypeptide having the amino acid sequence disclosed at NCBI Accession No: O00574, GI: 3121816;

(ii) a variant (such as a splice variant), paralogue, orthologue or derivative of (i) having at least 70%, at least 80%, at least 90%, at least 95% or at least 99% amino acid sequence identity to (i) calculated over the full-length of (i);

(iii) the mouse CXCR6 polypeptide having the amino acid sequence disclosed at NCBI Accession No: NP_109637, GI: 157266315;

(iv) a variant (such as a splice variant), paralogue, orthologue or derivative of (iii) having at least 70%, at least 80%, at least 90%, at least 95% or at least 99% amino acid sequence identity to (iii) calculated over the full-length of (iii);

(v) the rat CXCR6 polypeptide having the amino acid sequence disclosed at NCBI Accession No: NP_001096057, GI: 156564361;

(vi) a variant (such as a splice variant), paralogue, orthologue or derivative of (v) having at least 70%, at least 80%, at least 90%, at least 95% or at least 99% amino acid sequence identity to (v) calculated over the full-length of (v);

(vii) a fragment of any one of (i)-(vi) having at least 100, at least 200, at least 250, or at least 300 amino acids. Preferably, said fragment (vii) comprises a CXCL16 binding domain.

A variety of suitable test agents may be employed in the method of this aspect of the invention. The test agent may be, e.g., a small molecule, an antibody molecule, a peptide or a nucleic acid. In some cases the method of this aspect of the invention comprises screening a library of test agents, e.g. an antibody library such as an scFv library. Preferably, the test agent comprises an agent selected from:

an antibody or fragment thereof capable of binding the 5T4 polypeptide;

an antibody or fragment thereof capable of binding the CXC chemokine receptor polypeptide;

an antibody or fragment thereof capable of binding to both the 5T4 polypeptide and the CXC chemokine receptor polypeptide; and an antibody or fragment thereof which selectively binds a complex which comprises the 5T4 polypeptide and the CXC chemokine receptor polypeptide (e.g. a 5T4-CXCR4 complex or a 5T4-CXCR6 complex). In accordance with the method of the first aspect of the invention 5T4 polypeptide preferably comprises an extracellular domain and the test agent preferably comprises an antibody or fragment thereof that binds the extracellular domain of the 5T4 polypeptide. More preferably, the test agent comprises an antibody or fragment thereof which selectively binds a complex which comprises the 5T4 polypeptide and the CXC chemokine receptor polypeptide (e.g. a 5T4-CXCR4 complex or a 5T4-CXCR6 complex). The test agent may be a small molecule capable of inhibiting a protein-protein interaction, particularly a small molecule capable of interfering with protein-protein interactions that occur within a membrane. A suitable library of compounds, known as a "credit card" library, has been disclosed [52; the entire contents of which are expressly incorporated herein by reference in their entirety].

In accordance with the method of the first aspect of the invention the test agent may be found not to inhibit the interaction between the 5T4 polypeptide and the CXC chemokine receptor polypeptide. Preferably, however, the test agent is found to inhibit the interaction between 5T4 polypeptide and the CXC chemokine receptor polypeptide. A test agent which is found to exhibit said inhibitory activity may be further characterised and/or subjected to additional testing such as testing in a chemotaxis assay and/or an in vivo assay for the ability to inhibit metastasis, as described herein. In this way, the 5T4-CXC chemokine receptor polypeptide interaction assay may be utilised as an initial screen, for example, to identify promising candidates to be put forward for the more difficult and potentially more costly stages of testing such as testing in vivo for metastasis inhibitory activity.

In some cases the method of this aspect of the invention further comprises isolating the test agent and, optionally, formulating the test agent into a pharmaceutical composition with at least one pharmaceutically acceptable salt, carrier or excipient. The test agent or pharmaceutical composition comprising the test agent may be used in a method of treatment of cancer, in particular in the treatment of prevention of metastasis. Preferred methods of treatment are as defined in connection with the sixth aspect of the invention.

In a second aspect, the present invention provides an antibody or fragment thereof that binds to:

a 5T4 polypeptide;

a CXC chemokine receptor polypeptide; and/or a complex comprising the 5T4 polypeptide and the CXC chemokine receptor polypeptide, wherein said antibody or fragment thereof inhibits interaction between the 5T4 polypeptide and the CXC chemokine receptor polypeptide or inhibits the activity of said complex (in particular signal transduction activity in response to a chemokine ligand). A preferred antibody or fragment thereof in accordance with the invention selectively binds a complex which comprises a 5T4 polypeptide, as defined herein, and a CXC chemokine receptor polypeptide, as defined herein, (e.g. a 5T4-CXCR4 complex or a 5T4-CXCR6 complex).

Preferably, the antibody or fragment thereof binds said complex in preference to a 5T4 polypeptide or a CXC chemokine receptor polypeptide which is not in the form of the complex (i.e. the antibody or fragment thereof may exhibit limited or no binding to an individual polypeptide member of said complex). Preferably, the antibody or fragment thereof exhibits at least 10-fold, at least 100-fold or at least 1000-fold greater binding affinity for said complex than for a 5T4 polypeptide that is not complexed with a CXC chemokine receptor polypeptide.

The antibody or fragment thereof, in accordance with this aspect of the invention, may be identified or identifiable in a method according to the first aspect of the invention. The skilled person is able to provide antibodies and antibody fragments comprising antibody binding domains that are capable of binding to a 5T4 polypeptide as defined in relation to the first aspect of the invention, are capable of binding to a CXC chemokine receptor polypeptide as defined in relation to the first aspect of the invention or are able to bind to a complex comprising a 5T4 polypeptide and a CXC chemokine receptor polypeptide (e.g. a 5T4-CXCR4 complex or a 5T4-CXCR6 complex). Such antibodies or fragments may be readily screened for the ability to inhibit the interaction of the 5T4 polypeptide and the CXC chemokine receptor polypeptide using a method in accordance with the first aspect of the invention. A suitable antibody may in some cases be isolated from a library of antibody molecules (e.g. a phage display library) using, e.g., a complex comprising a 5T4 polypeptide and a CXC chemokine receptor polypeptide as an antigen.

Alternatively or additionally, a suitable antibody may be raised by administering, particularly injecting, a complex comprising a 5T4 polypeptide and a CXC chemokine receptor polypeptide into an animal (such as a rodent, rabbit or other laboratory mammal). Preferably, an antibody may be raised by injecting said complex into a 5T4 null mouse. In some cases, the antibody or fragment in accordance with the second aspect of the invention inhibits formation of a complex comprising the 5T4 polypeptide and the CXCR4 polypeptide or inactivates said complex (e.g. by binding to said complex and preventing or inhibiting signal transduction mediated by the complex in response to a chemokine). The antibody or fragment of this aspect of the invention preferably binds to an epitope present on the extracellular domain of a 5T4 polypeptide or an extracellular portion of a complex comprising the 5T4 polypeptide and a CXC chemokine receptor polypeptide.

In a third aspect the present invention provides an antibody or fragment thereof as defined in connection with the second aspect of the invention for use in a method of medical treatment.

In a fourth aspect the present invention provides an antibody or fragment thereof as defined in connection with the second aspect of the invention for use in the prevention or treatment of metastasis or an inflammatory condition.

Preferably, said metastasis is of a cancer which comprises at least one 5T4 polypeptide-positive and CXC chemokine receptor polypeptide-positive (e.g. CXCR4-positive or CXCR6-positive) cell. The metastasis may be of a cancer of breast, ovarian, renal, prostate, gastric, oral, cervix, NSCLC, colorectal, glioma, neuroblastoma or acute lymphoblastic leukaemia (ALL) origin. The antibody or fragment thereof as defined in connection with the second aspect of the invention may be for use in a method of treatment of Pre-B ALL, in particular a high risk cytogenetic subtype of pre-B ALL (e.g. Ph+, iAMP21, MLL and/or hypodiploidy pre-B ALL). The pre-B ALL may be pre-B ALL exhibiting elevated expression 5T4 (such as elevated expression of a 5T4 gene), e.g. elevated expression in comparison with the 5T4 gene expression level of a bone marrow sample obtained from a subject having low risk ALL which exhibits hyperdiploidy and/or the TEL-AML1 fusion. The pre-B ALL may comprise extramedullary ALL. The ALL may comprise cells the exhibit cell surface expression of CXCR4, in particular cell surface expression of a complex comprising a 5T4 polypeptide and a CXCR4 polypeptide. A convenient method to determine whether a cell (e.g. a cancer cell or leukaemic lymphocyte) exhibits cell surface expression of a CXC chemokine receptor polypeptide or a complex comprising a 5T4 polypeptide and a CXC chemokine receptor polypeptide may comprise a step of contacting the cell with an antibody that selectively binds said polypeptide or that selectively binds said complex. The antibody is preferably labelled or conjugated to a detectable signal to permit detection. A preferred method of identifying a cell that exhibits cell surface expression of said polypeptide or said complex involves use of FACS.

In accordance with this and other aspects of the invention, the antibody or fragment thereof may be for use in a method of treating a subject that has been determined to have pre-B ALL with elevated 5T4-expression, wherein the determination has been made in accordance with the method of the ninth aspect of the invention.

CXC chemokine receptors have been shown to be implicated in the progression of inflammatory diseases. For example, the chemokine receptors CXCR4 and CXCR6 are involved in the progression of inflammatory diseases including, but not limited to, rheumatoid arthritis [56], asthma [57], atherosclerosis [58], inflammatory bowel disease [59] and inflamed liver [60]. CXCR4 expression has been determined on multiple myeloid progenitor cells such as multipotent adult progenitor cell-derived progenitor cells (MDPC) [61] and mast cell progenitor cells [62], where the chemokine receptor is involved in recruitment of these cells to sites of inflammation. Disruption of CXCR4 function with low molecular weight chemical compounds has been proven to attenuate hyper-immune responses such as hypersensitivity-type pulmonary granuloma formation [63], allergic lung inflammation and airway hyperreactivity [57]. The involvement of CXC chemokine receptors CXCR4 and CXCR6 in inflammatory conditions in the following non-exhaustive lists:

CXCR4

Inflammatory bowel disease;

VEGFR1/CXCR4-positive progenitor cells modulate local inflammation and augment tissue perfusion by a SDF-1-dependent mechanism;

AMD3100, a CXCR4 antagonist, attenuates allergic lung inflammation and airway hyperreactivity;

Expressed on mast cell progenitors;

AMD3465 eliminates pulmonary granuloma formation.

CXCR6

Inflamed Liver

CXCR6 helps mediate the recruitment of activated CD8 lymphocytes in Graft versus host disease-induced hepatitis and may be a useful target to treat pathological inflammation in the liver.

Atherosclerosis

CXCR6 is proatherosclerotic through its involvement in the recruitment of CXCR6+ leukocytes into the atherosclerosis-prone aortic wall. In the absence of CXCR6, experimental models of atherosclerosis exhibit an approximately 50% reduction in lesion formation.

Rheumatoid Arthritis

CXCR6 has been shown to be expressed more frequently on synovial T cells than in peripheral blood. Furthermore, its specific ligand is also expressed in rheumatoid arthritis synovial and it is this interaction of CXCR6 and CXCL16 that results in T cell accumulation and stimulation in rheumatoid arthritis synovium.

Therefore, in accordance with the fourth aspect of the invention an antibody or fragment thereof as defined in connection with the second aspect of the invention may be for use in the prevention or treatment of an inflammatory condition selected from: rheumatoid arthritis, asthma, atherosclerosis, inflammatory bowel disease and inflamed liver.

The subject is preferably human. However, the subject may be a mammalian subject such as a dog, cat, rodent, non-human primate or a domesticated farm animal (e.g. cow, pig, sheep, goat). The subject may be a human child, e.g. a child having pre-B ALL. The subject may have previously been diagnosed as having a cancer or as being at risk of developing a cancer.

In a fifth aspect the present invention provides use of an antibody or fragment thereof as defined in connection with the second aspect of the invention in the preparation of a medicament for the prevention or treatment of metastasis or an inflammatory condition.

Preferably, said metastasis is of a cancer which comprises at least one 5T4 polypeptide-positive and CXC chemokine receptor polypeptide-positive (e.g. CXCR4-positive or CXCR6-positive) cell. The metastasis may be of a cancer of breast, ovarian, renal, prostate, gastric, oral, cervix, NSCLC, colorectal, glioma, neuroblastoma or acute lymphoblastic leukaemia (ALL) origin. The use in accordance with this aspect of the invention may be in the preparation of a medicament for the prevention or treatment of Pre-B ALL, in particular a high risk cytogenetic subtype of pre-B ALL (e.g. Ph+, iAMP21, MLL and/or hypodiploidy pre-B ALL). The pre-B ALL may be pre-B ALL exhibiting elevated expression of a 5T4, in particular elevated 5T4 gene expression, e.g. elevated expression in comparison with the 5T4 gene expression level of a bone marrow sample obtained from a subject having low risk ALL which exhibits hyperdiploidy and/or the TEL-AML1 fusion. The pre-B ALL may comprise extramedullary ALL. The use in accordance with this aspect of the invention may be in the preparation of a medicament for treatment of a subject as defined in connection with the fourth aspect of the invention.

Preferably, said inflammatory condition is selected from: rheumatoid arthritis, asthma, atherosclerosis, inflammatory bowel disease and inflamed liver.

In a sixth aspect the present invention provides a method of treating or preventing metastasis or an inflammatory condition in a subject in need of said treatment, comprising administering a therapeutically effective amount of an antibody or fragment thereof as defined in connection with the second aspect of the invention to the subject.

Preferably, said metastasis is of a cancer which comprises at least one 5T4-positive and CXC chemokine receptor polypeptide-positive (e.g. CXCR4-positive or CXCR6-positive) cell. The cancer may be as defined in connection with the fourth aspect of the invention. Preferably, said inflammatory condition is selected from: rheumatoid arthritis, asthma, atherosclerosis, inflammatory bowel disease and inflamed liver. The subject may be as defined in connection with the fourth aspect of the invention.

Current methods for identification of ALL patients who will develop extramedullary disease are far from optimal; these patients generally have a poor outcome. Although it is generally thought that 5T4 is not expressed by haematopoietic cells or haematological derived tumours, the present inventors have surprisingly found that a subset of high risk ALL exhibits elevated 5T4 gene expression. Given the functional synergy between 5T4 and CXCR4 reported herein, the present findings suggest a role for 5T4 in chemotaxis of leukaemic cells. Thus, 5T4/CXCR4-positive ALL cells having elevated 5T4 expression are believed to have an enhanced ability to home to extramedullary compartments producing CXCL12.

Accordingly, in a seventh aspect the present invention provides a method for assessing the prognosis of a subject having acute lymphoblastic leukaemia (ALL), particularly pre-B ALL, comprising measuring, directly or indirectly, 5T4 expression (e.g. 5T4 gene expression) in a sample which has been obtained from the subject, wherein elevated 5T4 expression in said sample in comparison with a reference level of 5T4 expression indicates that said subject has a poor prognosis. Said reference level of 5T4 expression (e.g. 5T4 gene expression) may be a pre-determined level that corresponds to the level of 5T4 expression in a bone marrow sample obtained from a subject having low risk ALL which exhibits hyperdiploidy and/or the TEL-AML1 fusion. The pre-determined reference level may be an average level derived from a population of subjects having low risk ALL. In some cases the method of this aspect of the invention may comprise a step of determining a reference level of 5T4 gene expression. Preferably, the reference level and the test sample level are measured in the same way, e.g. by processing the samples in parallel. An elevated level of 5T4 expression may be 10%, 20%, 50%, 100%, 200%, 300% or greater than said reference level.

The method of this aspect of the invention is useful for providing clinically relevant prognostic information about a subject having ALL. Said poor prognosis may comprise: an elevated risk of having or developing extramedullary ALL; an elevated risk of relapse; an elevated risk of therapeutic failure; and/or a lower likelihood of survival.

In accordance with the method of this aspect of the invention the subject may be as defined in connection with the fourth aspect of the invention. The sample preferably comprises lymphocytes. A preferred sample comprises bone marrow.

In accordance with this and other aspects of the invention 5T4 expression may be measured using any suitable technique and may comprise measurement of a nucleic acid encoding a 5T4 polypeptide, as defined herein, present in or extracted from said sample and/or measurement of the amount of a 5T4 polypeptide, as defined herein, present in or extracted from said sample. Preferably, measurement of 5T4 expression comprises: (a) detecting or determining mRNA levels expressed from the 5T4 gene; (b) determining the presence or amount of a 5T4 polypeptide; and/or (c) determining the presence or amount of a complex comprising a 5T4 polypeptide and a CXC chemokine receptor polypeptide (e.g. a CXCR4 polypeptide or a CXCR6 polypeptide). The method may further comprise a step of obtaining the sample from the subject (e.g. obtaining a bone marrow aspirate sample and/or a blood sample). The sample may be stored (e.g. frozen) and/or processed (e.g. to extract DNA, RNA or protein for analysis) prior to carrying out any measurement of 5T4 expression. The method of this aspect of the invention may further comprise measuring, directly or indirectly, expression of a CXC chemokine receptor polypeptide or gene encoding said polypeptide (e.g. a CXCR4 polypeptide, CXCR4 gene, CXCR6 polypeptide or CXCR6 gene) in the sample.

In an eighth aspect the present invention provides a kit for assessing the prognosis of a subject having acute lymphoblastic leukaemia (ALL), particularly pre-B ALL, comprising reagents for carrying out the determination 5T4 expression on a sample and instructions for carrying out the determination and, optionally, for interpreting the results. Preferred types of kit may comprise one or more reagents selected from the following:

(a) an antibody capable of recognising a 5T4 polypeptide or fragment thereof, or capable of recognising a complex comprising the 5T4 polypeptide and a CXC chemokine receptor polypeptide (e.g. a 5T4-CXCR4 complex or a 5T4-CXCR6 complex), for example for use in a binding assay such as an ELISA, in an immunohistochemical test or in a flow cytometry-based method. The antibody may be detected either by being directly labelled or through interaction with one or more other species, for example a labelled secondary antibody;

(b) one or more primers directed to the nucleic acid sequence of the 5T4 gene, for example for measuring 5T4 mRNA; and/or (c) an oligonucleotide probe directed to the nucleic acid sequence of the 5T4 gene, for example for detecting 5T4 gene expression. As for antibody reagents, the probes may conveniently be directly or indirectly labelled to enable them to be detected. The probe may be immobilised on a substrate, e.g. in the form of a microarray. The one or more primers may be selected from the Taqman Gene Expression library h5T4 primer set having the Applied Biosystems assay identifier Hs00272649_s1. The kit may further comprise a control, e.g. a sample to be used as a reference level. Preferred primers include primers designed around the portion of a 5T4 gene that encodes the transmembrane domain of the 5T4 polypeptide (e.g. primers based on the sequence encoding the transmembrane domain of the human or mouse 5T4 polypeptide or the human or mouse 5T4 paralogue polypeptide as shown in FIGS. 21 and 25, respectively).

Preferably, one or more primers or primer pairs are selected from the following primers which amplify a region spanning the extracellular domain and the whole TM domain of the 5T4 paralogue and 5T4, respectively:

```
                                   (SEQ ID NO: 9)
5T4para-F GCG GCT TCG CTG CGC GGA C

                                   (SEQ ID NO: 10)
5T4para-R ATC TGG TCC CGG CAC GCC TCG

                                   (SEQ ID NO: 11)
5T4-F AAT GGC ACC CTG GCT GAG TTG

                                   (SEQ ID NO: 12)
5T4-R TCT GGG GTC CGC ATT GAT TTC
```

In a ninth aspect the present invention provides a method for determining whether a subject having acute lymphocytic leukaemia (ALL), particularly pre-B ALL, is suitable for 5T4 polypeptide-targeted and/or CXC chemokine receptor polypeptide-targeted treatment comprising measuring, directly or indirectly, 5T4 expression, particularly cell surface expression (e.g. cell surface/cell membrane localisation of a 5T4 polypeptide), in a sample which has been obtained from the subject, wherein elevated 5T4 expression in said sample in comparison with a reference level of 5T4 expression indicates that said subject is suitable for said treatment. Said reference level of 5T4 expression (particularly cell surface expression) may be a pre-determined level that corresponds to the level of 5T4 expression in a bone marrow sample obtained from a subject having low risk ALL which exhibits hyperdiploidy and/or the TEL-AML1 fusion. The pre-determined reference level may be an average level derived from a population of subjects having low risk ALL. In some cases the method of this aspect of the invention may comprise a step of determining a reference level of 5T4 expression, particularly cell surface expression. Preferably, the reference level and the test sample level are measured in the same way, e.g. by analysing the samples in parallel. An elevated level of 5T4 expression (particularly cell surface expression) may be 10%, 20%, 50%, 100%, 200%, 300% or greater than said reference level. In accordance with the method of this aspect of the invention the subject may be determined to have a subtype of ALL that has greater sensitivity to 5T4-targeted and/or CXCR4-targeted therapy such that the subject is more likely to respond to such therapy. The method of this aspect of the invention may be carried out on a plurality of subjects having ALL, e.g. for stratifying a population of patients to identify those most suitable for 5T4 polypeptide-targeted and/or CXC chemokine receptor polypeptide-targeted therapy.

Preferably, when the subject is determined to be suitable for 5T4 polypeptide-targeted and/or CXC chemokine receptor polypeptide-targeted therapy, the method of this aspect of the invention further comprises administering or advising the administration of a therapeutically effective amount of an antibody or fragment thereof as defined in connection with the second aspect of the invention to the subject. Additionally or alternatively, when the subject is determined to be suitable for 5T4 polypeptide-targeted and/or CXC chemokine receptor polypeptide-targeted therapy, the method of this aspect of the invention further comprises administering or advising the administration of a therapeutically effective amount of 5T4-based super-antigen therapy (e.g. ABR-214936 see [50] or ANYARA see [53]).

The present invention includes the combination of the aspects and preferred features described except where such a combination is clearly impermissible or is stated to be expressly avoided. These and further aspects and embodiments of the invention are described in further detail below and with reference to the accompanying examples and figures. Any references to colours in the figures is for guidance only; the accompanying figures do not contain colour information.

DESCRIPTION OF THE FIGURES

FIGS. 1A-1I: Differentiating mES cells show 5T4dependent CXCL12 chemotaxis. Panel A, Quantitative RT-PCR of WT ES cells confirm microarray results (not shown) with changes in 5T4, CD26 and CXCL12 mRNA but not CXCR4 after 3 days differentiation, (triplicates of the WT ES differentiation; 5T4, CD26, CXCR4, CXCL12 changes respectively P=0.014, 0.057, 0.81, 0.012 by Student's t-test) Panel B, These transcriptional changes are reflected in altered surface expression determined by FACS of 5T4 (triangles) and CD26(circles) during the differentiation period; the pluripotent marker SSEA-1 does not change (diamonds) (n>3 a single representative time course shown). Panel C, Western blot analysis of PAGE separated reduced WT or 5T4KO ES cells either undifferentiated (U) or differentiating (D) probed with CXCR4 antibody identifies a band at 46 KDa with no difference in the total amount of CXCR4 between cell types or differentiation status. Panel D, Increased CXCL12levels were detected in the culture medium by ELISA, after 3 days of differentiation (black columns) compared to undifferentiated cells (white columns), (WT=71±4 vs 171±9 pg/ml, 5T4KO=40±2 vs 84±5 pg/ml). Panel E, Undifferentiated WT and 5T4KO ES cells (white columns) exhibit no CXCL12 chemotaxis but differentiating (black columns) WT but not 5T4KO ES cells, acquire significant chemotaxis. Panel F, CXCL12 dependent chemotaxis was determined over 6 days. Differentiating WT-ES cells (black columns) exhibited a peak in CXCL12 chemotaxis at 3 days following LIF withdrawal whilst 5T4KO ES cells (white columns) exhibit no CXCL12 chemotaxis in this time frame. Panel G, The chemotactic migration exhibited by differentiating WT-ES cells (black columns) towards CXCL12 was abolished in the presence of an antibody against CXCL12 (10 μg) but not in presence of an irrelevant control antibody (10 μg). Undifferentiated, (white columns) exhibited no change in chemotactic migration under any conditions. Panel H, Chemotaxis of differentiating WT-ES cells, (black columns) was shown to be mediated through CXCR4 by inhibition of the receptor by a 2 hr pre-incubation with 10 μM AMD3100 whilst there was no effect of 10 μM AMD3100 on undifferentiated WT-ES cells (white columns). Panel I, Undifferentiated (white columns) or differentiating (black columns) 5T4KO ES cells show no change in chemotactic response in the presence of the CD26 inhibitor diprotin A (10 μM). (−=no CXCL12, +=10 ng/well CXCL12). All chemotactic experiments were performed at least three times with triplicates for each condition.

FIGS. 5A and 5B: Disruption of cytoskeleton and CXCL12 dependent signaling in 5T4KO MEFS. Panel A, Disruption of F-actin filaments in differentiating 5T4KO MEFs in comparison to WT cells or in 5T4KO MEFs infected with RAd-m5T4 where F-actin cytoskeletal organization is restored. Panel B, WT MEFs exhibited an increase in ERK phosphorylation in response to CXCL12 stimulation that was prevented by the MEK1 inhibitor PD98059 and the CXCR4 inhibitor AMD3100 but not by the PI3K inhibitor LY294002. In contrast, 5T4KO MEFs did not respond to CXCL12 stimulation. However this was not due to an overall disruption of MAPK/ERK signaling in the 5T4 null cells as both genotypes exhibited an increase in ERK1/2 phosphorylation in response to PMA stimulation that was blocked by MEK1 inhibition but was independent of both CXCR4 and PI3K activity. Total ERK was used as a loading control (M=50 μM MEK1 inhibitor PD98059, P=50 μM PI3 kinase inhibitor LY294002 or C=10 μM CXCR4 inhibitor AMD3100).

FIGS. 6A and 6B: The transmembrane domain of 5T4 is necessary for CXCR4cell surface expression. Panel A, 5T4KO MEFs were transduced with retroviral vectors encoding both eGFP and full length or truncated 5T4 or chimeric 5T4/CD44 constructs (schematic representation are shown, with white, grey and black or spotted, diagonal striped and vertical striped boxes corresponding to the extracellular, TM and cytoplasmic regions of 5T4 and CD44 respectively). Successful infection was assessed by GFP expression (green) and the location of CXCR4, (red) assessed in these cells. Cell surface expression of CXCR4 is only seen with those constructs with 5T4 TM (viii, xvi, xxiv); the extracellular and cytoplasmic domains of 5T4 are not required. Panel B, Consistent with this CXCL12 chemotaxis of the retrovirally transduced GFP+5T4 null MEFs with 5T4 extracellular domain, (dark grey), 5T4extracellular domain CD44 transmembrane and cytosolic domains, (grid) and mock infected, (white) showing no affect whereas full length 5T4, (light grey), 5T4 extracellular and transmembrane domains, (spots)

and CD44 extracellular domain 5T4 transmembrane and cytosolic domains, (stripes) show comparable levels to wild-type (black columns) (−=no CXCL12, +=30 ng/well CXCL12).

Figure 7:
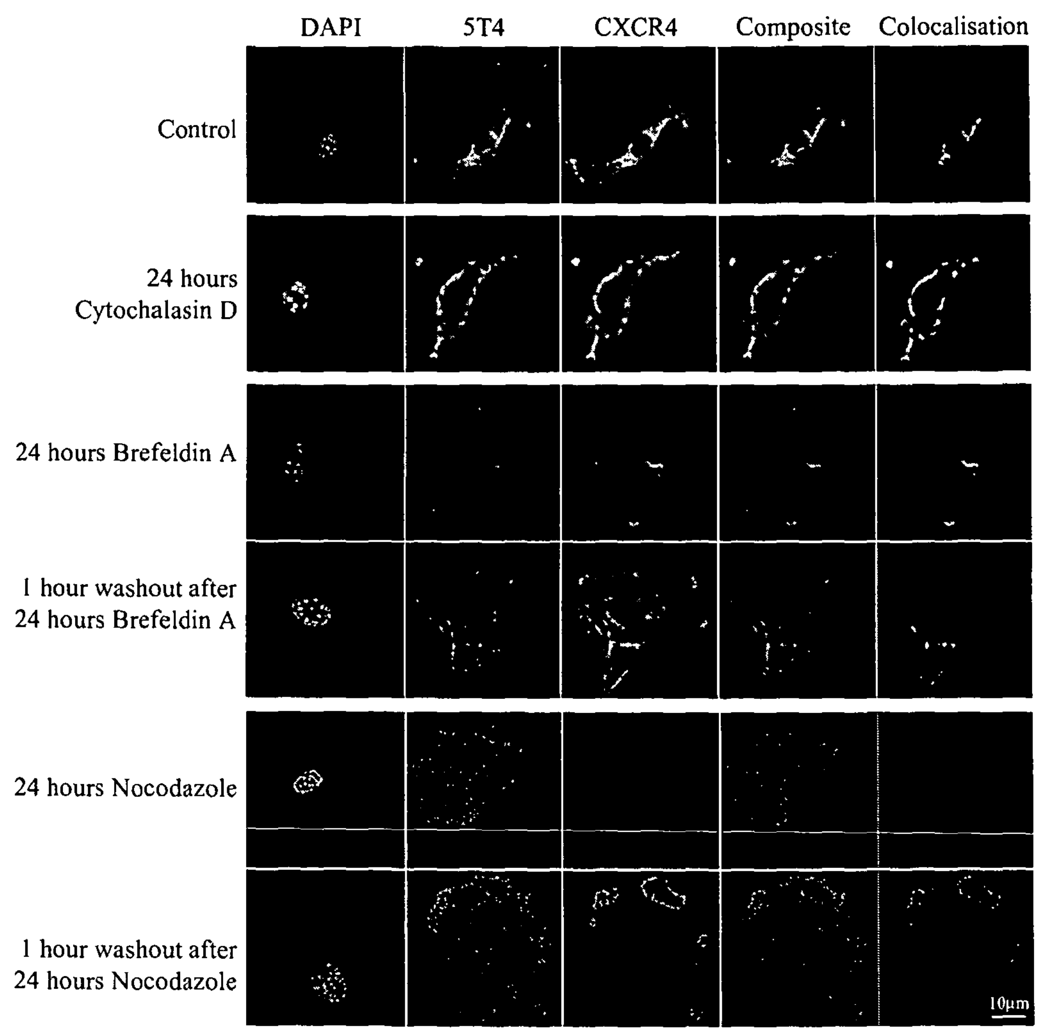

FIG. 7: Effects of cytoskeleton, microtubule and Golgi disruption on the co-localization pattern of 5T4 and CXCR4. Primary murine embryonic fibroblasts were assessed for their pattern of 5T4 and CXCR4 expression by immunofluorescence following disruption of the cytoskeleton, Golgi or microtubules for 24 hours with either 985 nM cytochalasin D, 3.6 μM brefeldin A or 332 nM nocodazole respectively. Untreated primary murine embryonic fibroblasts exhibit cell surface expression of both 5T4 and CXCR4 with regions of colocalisation (5T46=green, CXCR4=red, DAPI=blue) of the two antigens (seen as yellow) or in the colocalisation analysis. Cytoskeleton disruption was determined by immunofluorescence using AlexaFluor 633 conjugated phalloidin. Following 24 hours treatment with cytochalasin D, no polymerized actin filaments were detectable (data not shown). There were no detectable differences in the cell surface expression or colocalisation of 5T4 and CXCR4 in comparison to untreated controls. Golgi disruption following brefeldin A treatment was confirmed by immunofluorescence detection of sphingolipids using BODIPY labeled NBD C6 ceramide (data not shown). Brefeldin A reduced levels of cell surface expression of both antigens. However, some cell surface expression was detected with marked with colocalisation. One hour after brefeldin A washout cell surface expression of both antigens had returned to levels with marked cell surface colocalisation similar to that of controls. Microtubule disruption following nocodazole treatment was confirmed by immunofluorescence detection using an antibody against β-tubulin (data not shown). Following nocodazole treatment there was no cell surface detection of CXCR4 but with 5T4 still detectable at the cell surface albeit at a diminished level. One hour after nocodazole washout both antigens were detectable at the cell surface with marked colocalisation similar to controls.

FIGS. 8A-8E: Inhibition of chemotaxis by monoclonal antibodies recognizing 5T4. Panel A, shows the IgG subclasses of four m5T4 specific monoclonal antibodies (mAb) (made in 5T4 null mice) recognizing distinct epitopes in the proximal and distal LRR domains. Panel B, shows titration of mAb activity in m5T4 specific ELISA [27]. Panel C, The chemotactic migration exhibited by differentiating WT-ES cells towards CXCL12 was abolished in the presence of the m5T4 specific mAb B1C3 (10 μg) but not in presence of mAb P1C9 (10 μg) or an irrelevant control antibody (10 μg). MAbs B3F1 and B5C9 (10 μg) reduced the chemotactic response. (−= no CXCL12, +=10 ng/well CXCL12). Panel D, B1C3 and P1C9 mAb dose response of inhibition of chemotaxis towards CXCL12 in differentiating WT-ES cells. B1C3demonstrated an IC50 of 0.38 μg/ml ±0.14 μg. Panel E, The chemotactic migration exhibited by primary WT mouse embryo fibroblasts was abolished in the presence of the m5T4 specific mAb B1C3 (10 μg) but not in presence of mAb P1C9(10 μg) or an irrelevant control antibody (10 μg) . MAbs B3F1 and B5C9 (10 μg) reduced the chemotactic response. (−=no CXCL12, +=30 ng/well CXCL12). All chemotactic experiments were performed at least three times with triplicates for each condition.

FIGS. 9A-9D: 5T4 and CXCR4 expression and chemotaxis in solid human tumor cell lines. Panel A, Localisation of 5T4 (green), CXCR4 (red) and CD26 (blue) in two breast (MCF-7, MDA-MB231) and one choriocarcinoma (JEG-3) cell line. Typical punctuate cell surface staining of 5T4, and CXCR4, and some co-localisation of these molecules (yellow, composite) is illustrated; only JEG-3 showed CD26 expression (cell surface). Panel B, Shows the CXCL12 mediated chemotaxis of the breast cancer lines MCF-7 (black) and MDA-MB-231, (white) and the choriocarcinoma JEG-3 in the absence (grey) or presence of 10 μM diprotin A (striped grey). The requirement for inhibition of this CXCL12 specific dipeptidyl peptidase was consistent with the high levels of surface expression of CD26, by JEG-3 (not shown) (+ or −30 ng/well CXCL12). All chemotactic experiments were performed at least three times with triplicates for each condition. Panel C, Western blot analysis of PAGE separated unreduced MDA-MB-231, MCF-7 and JEG-3 membrane lysates probed with either CXCR4 or 5T4 antibodies identifies bands at 46 kDa for CXCR4 and 75-80 kD for 5T4, but in addition, both probes identify a higher molecular weight putative 5T4/CXCR4 complex at around 130 kDa. Denistometric scans of western blots between approximately 60-140 kDa (5T4 probe) and 30-140 kDa (CXCR4 probe). Panel D, Evidence for a 5T4/CXCR4 complex is also seen on western blot analysis of unreduced MDA-MB-231, MCF-7 and JEG-3 membrane lysate 5T4 and CXCR4 pull downs probed with antibodies against CXCR4 and 5T4, respectively. Under reducing conditions, the epitope recognized by 5T4 antibodies is destroyed but CXCR4 at 46 kD is detectable on the reduced gels of the 5T4 pulldown, (not shown). Thus, specific pull downs but not the controls, probed with either anti-CXCR4 or anti-5T4 detected molecules migrating ≈130 kDa in all the tumor lines.

FIGS.10A-10C: 5T4 and CXCR4 expression and chemotaxis in human ovarian carcinoma cell lines. Panel A, Localisation of 5T4 (green), and CXCR4 (red) in four ovarian carcinoma cell lines (SKOV3, CAOV3, OVCAR3 and PA1). Typical punctuate cell surface staining of 5T4, and CXCR4, and some co-localisation of these molecules (yellow, composite) is illustrated. Panel B, Western blot analysis of PAGE separated unreduced SKOV3, CAOV3, OVCAR3 and PA1 membrane lysates probed with either CXCR4 or 5T4 antibodies identifies bands at 46 kDa for CXCR4 and 75-80 kD for 5T4, but in addition, both probes identify a higher molecular weight putative 5T4/CXCR4 complex at around 130 kDa. Panel C, Shows the CXCL12 mediated chemotaxis of the ovarian cancer lines SKOV3(black) and CAOV3, (white) OVCAR3 (grey) and PA1 (striped) in the absence or presence of 10 μM diprotin A. The requirement for inhibition of this CXCL12 specific dipeptidyl peptidase was consistent with the high levels of surface expression of CD26, by SKOV3 and CAOV3 (not shown) (+ or −10 ng/well CXCL12). All chemotactic experiments were performed at least three times with triplicates for each condition.

FIGS. 11A and 11B: 5T4 shRNA inhibition of CXCL12 dependent chemotaxis in SKOV3 human ovarian carcinoma cells. Panel A, SKOV3 cells were transfected with plasmids encoding specific shRNA against human 5T4 and the marker gene eGFP. Levels of cell surface 5T4 expression (black solid) was assessed on eGFP positive cells 72 hours post transfection. SKOV3 cells transfected either with a control plasmid or shRNA#1 showed no decrease in cell surface expression of 5T4. SKOV3 cells transfected with shRNA#3 showed a decrease in cell surface expression (white solid=negative control, grey line=positive control). Panel B, Transfected cells were cell sorted on the basis of eGFP expression and placed onto a CXCL12chemotactic gradient. SKOV3 cells transfected with shRNA#3 exhibited no chemotaxis towards CXCL12 (+ or −10 ng/well CXCL12).

FIGS.12A-12E: 5T4 and CXCR4 expression in human paediatric leukemias. Panel A, Box plot diagram illustrating CXCR4 and 5T4 expression in childhood pre-B ALL. The x axis shows cytogenetic risk groups. High risk include those with Ph+, iAMP21, MLL and hypodiploidy. Low risk include hyperdiploidy and TEL-AML1, all the rest have been grouped as others. The y axis represents the relative gene expression level of CXCR4 or 5T4. Each box plot shows the distribution of expression levels from 25th to 75th percentile. The median is shown as a line across the box, whereas the + is the calculated mean expression level for the particular subtype. Values within the outer fence are shown as circles and those outside as asterisks. ANOVA shows that the high risk B-ALL have significantly higher levels of 5T4 (P=0.0005) but not CXCR4 (P=0.35) compared to low risk and "other" categories. Panel B, Quantitative RT-PCR of 5T4 on Pre B-ALL patient samples cells confirm microarray results with patients with high risk patients exhibiting increased levels of 5T4 transcript in comparison to low risk patients (P=0.002 by Mann Whitney U test). Panel C, All pre B-ALL human tumor cell lines show surface expression of CXCR4 with the cell lines Tom-1 and a subpopulation of the cell line SupB15 exhibiting 5T4 positive cells as determined by FACS. Panel D, Immunofluorescence detection of characteristic cell surface 5T4 expression (green) on live labelled cytospins of SupB15 but not REH human pre-B ALL cells (DAPI nuclear stain =blue). Panel E, Western analysis of PAGE separated unreduced SupB15 membrane lysates showing 46 Kda CXCR4 and 72-80 Kda 5T4 molecules as well as a higher molecular weight (≈130 kDa) 5T4/CXCR4 complex.

FIGS. 13A and 13B: Flow cytometric analyses for 5T4 surface expression in pre-B acute lymphoblastic leukemic bone marrow patient diagnostic samples. Panel A, Frozen bone marrow aspirate single cell suspensions from patients with childhood pre-B ALL were labelled with anti-5T4, CD19 and CD10 specific antibodies. Dead cells were excluded using the viability stain 7AAD. The B cell population was gated on cells double positive for CD19and CD10. 5T4 expression was assessed in this population and the percentage of positive cells was calculated. Panel B, Immunofluorescence detection of characteristic cell surface 5T4expression (green) on some cells in cytospins of 5T4 labelled pre-B ALL patient number 57biopsy sample (DAPI nuclear stain=blue).

FIGS. 14A-14C: Cellular location of CXCR6 and 5T4 in differentiating ES cells, MEFs and human tumour cell lines. Panel A, Following LIF withdrawal WT ES cells undergo an EMT with cells eventually becoming dispersed with an arborized morphology. The expression and cellular localization of 5T4 (green) and CXCR6 (red) molecules before and after differentiation was determined by immunofluorescence of fixed cells grown on glass plates. Undifferentiated WT-ES cells are 5T4-negative with CXCR6 expression low and intracellular; following differentiation both molecules can be detected at the cell surface with some areas of co-localisation (yellow). This phenomenon was also evident in WT murine embryonic fibroblasts with co-localisation of 5T4 (green) and CXCR6 (red) on the cell surface. By contrast, 5T4KO MEFs cells show only intracellular CXCR6 expression. In human tumour cell lines the breast cancer cell line MCF-7, and a choriocarcinoma cell line, JEG-3 show cell surface expression of 5T4 (green) and CXCR6 (red) with some areas of colocalisation (yellow). Panel B, Analysis of cell surface expression of CXCR6 (CXCR6=black line, negative control=black solid) by flow cytometry confirmed results obtained by immunocytochemistry with no evidence of CXCR6 cell surface expression on 5T4KO MEFs. Panel C, Differentiated WT ES cells were placed on a chemotactic gradient either towards the chemokine CXCL12 (as a positive control) or CXCL16. WT ES cells exhibited an approximately 2-fold increase in chemotaxis towards 10 ng/well CXCL16.

FIGS. 15A-15C: 5T4 is not required for chemotactic response to CXCL10 nor CXCR3 surface expression on ES cells. Panel A, immunofluroescence detection of 5T4(green) and CXCR3 (red) in WT-ES and 5T4KO differentiating ES cells. Cell surface expression of 5T4 is present only on WT-ES cells whilst cell surface expression of CXCR3 is evident in both WT and KO ES cells. Panel B, Undifferentiated WT (white columns) and 5T4KO (black columns) ES cells exhibit no CXCL10 dependent chemotaxis but differentiating WT and 5T4KO ES cells, acquire significant chemotaxis towards CXCL10. Panel C, Undifferentiated ES cells treated with the CD26 inhibitor Diprotin A (10 μM) acquire increased chemotaxis towards CXCL10. Panel D, Treatment of both WT and KO differentiating ES cells with the $G_i$ protein inhibitor pertussis toxin (10 ng/ml) inhibits CXCL10 related chemotaxis (+ or −100 ng/well CXCL10). All chemotactic experiments were performed at least three times with triplicates for each condition.

FIGS. 16A-16D: 5T4 is not required for CXCR7 surface expression. Panel A, Western blot analysis of PAGE separated reduced primary murine embryonic fibroblast membrane lysates probed with CXCR7 antibodies (Abcam, Genetex) identifies a 42 kDa band in 5T4KO cells. Panel B, Immunofluroescence detection of CXCR7 (green) in SV40transformed WT and KO murine embryonic fibroblasts. Cell surface expression of CXCR7 is evident on KO and not WT fibroblasts. Panel C, Immunofluroescence detection of 5T4 (red) and CXCR7 (green) in undifferentiated and differentiating WT-ES and 5T4KO ES cells. Cell surface expression of CXCR7 is high in undifferentiated ES cells (either WT or 5T4KO). In 3day differentiating WT-ES cells, CXCR7 is relatively downregulated from the cell surface whereas in differentiating 5T4KO ES surface CXCR7 is retained. Panel D, the patterns of CXCR4 and CXCR7 cell surface expression appear to be reciprocal in the ovarian cell lines SKOV3, CAOV3, OVCAR3 and PA1; increased CXCR7 correlating with decreased chemotaxis to CXCL12 (see FIG. 10C).

FIGS. 17A and 17B: Sequence comparison of 5T4 TM domains. Alignments were performed using the ClustalW2 multiple sequence alignment program (EMBL-EBI) to compare Panel A, the TM domains of 5T4 across species (SEQ ID NO: 15) and Panel B, the TM domain of human 5T4 with human LRRC4 (SEQ ID NO: 17) and human PL5 (SEQ ID NO: 16), identical residues shaded black, similar residues shaded grey.

FIG. 18: The genomic nucleotide sequence of the human 5T4 paralogue (PL5; SEQ ID NO: 18).

FIG. 19: Predicted mRNA sequence of the human 5T4 paralogue (SEQ ID NO: 19).

FIGS. 20A-20D: Evidence for alternative translation initiation site of human PL5. Panel A, translation of the DNA sequence commencing at the second in-frame ATG codon (SEQ ID NO: 20). Panel B, Comparison of the first (SEQ ID NO: 22) and second (SEQ ID NO: 23) in-frame AUG codons of human PL5 sequence to the Kozak consensus sequence (SEQ ID NO: 21) required for initiation of translation; R=A or G; bold font—initiation AUG codon. Panel C, comparison of alternative translation initiation sites in terms of the calculated likelihood of the amino-acid sequence being a signal peptide. The Y score line shows the probability of signal peptidase cleavage; for details, see www.cbs.dtu.dk/services/SignalP-3.0/output.php. Panel D, HEK 293 cells were transfected with expression vectors encoding a fusion protein either human or murine PL5 with myc-tag located directly downstream of the predicted signal peptide (see panel B). The cells were cultured for 3 days and stained with Alexa Fluor® 488-labelled anti-myc antibody.

FIG. 21: Sequence comparison of human 5T4 and human PL5. Alignments were performed using the ClustalW2 multiple sequence alignment program (EMBL-EBI) to compare human 5T4 (SEQ ID NO: 24) with human PL5 (SEQ ID NO: 20). Gaps are indicated by dashes, identical residues shaded black, transmembrane region highlighted by asterisks.

FIG. 22: The genomic nucleotide sequence of the murine 5T4 paralogue (SEQ ID NO: 25).

FIG. 23: The predicted mRNA sequence of the murine 5T4 paralogue (SEQ ID NO: 26).

FIG. 24: The predicted amino acid sequence of the murine 5T4 paralogue (SEQ ID NO: 27).

FIG. 25: Sequence comparison of murine 5T4 and murine PL5. Alignments were performed using the ClustalW2 multiple sequence alignment program (EMBL-EBI) to compare murine 5T4 (SEQ ID NO: 28) with murine PL5 (SEQ ID NO: 27). Gaps are indicated by dashes, identical residues shaded black, transmembrane region highlighted by asterisks.

FIG. 26: The nucleotide sequence of the murine 5T4 paralogue expressed sequence tags from mouse olfactory brain cDNA (SEQ ID NO: 29).

FIG. 27: The amino acid sequence of the murine 5T4 paralogue protein (SEQ ID NO: 30) deduced from the translation of the mRNA nucleotide sequence.

FIG. 28: Sequence comparison of murine PL5 and EST. Alignments were performed using the ClustalW2 multiple sequence alignment program (EMBL-EBI) to compare the amino acid sequence deduced from translation of the mouse olfactory brain cDNA (EST) (SEQ ID NO: 30) and the murine 5T4 paralogue protein and murine 5T4 (SEQ ID NO: 27). Gaps are indicated by dashes, identical residues shaded black, transmembrane region highlighted by asterisks.

FIGS.29A-29C: Isolation of human PL5 cDNA. Panel A, shows results of RT-PCR experiments using primers designed outside the transmembrane region of the putative human 5T4 paralogue. A specific product was detected in cDNA generated from the SHSY-5Y neuroblastoma cell line (see lane 2). Panel B, shows a BLAST sequence alignment between the sequence obtained by sequencing the SHSY-5Y neuroblastoma cDNA RT-PCR product (SEQ ID NO: 31) and the human 5T4 paralogue mRNA sequence (SEQ ID NO: 32). Identical nucleotides are shown by vertical lines; gaps are indicated by dashes. Panel C, shows results of RT-PCR experiments for the constitutive gene EEF2. The results show that the cDNA is not contaminated with genomic DNA.

DETAILED DESCRIPTION OF THE INVENTION

5T4 Polypeptide

5T4 oncofoetal glycoprotein (also known as trophoblast glycoprotein, TPBG; NCBI GeneID: 7162) is an approximately 72 kDa transmembrane glycoprotein with an N-glycosylated extracellular domain. As used herein the 5T4 polypeptide may comprise at least the transmembrane domain, and optionally the extracellular domain and/or cytoplasmic domain, of:

- (i) the human 5T4 polypeptide having the amino acid sequence disclosed at NCBI Accession No: NP_006661, GI: 5729718;
- (ii) a variant (such as a splice variant), paralogue, orthologue or derivative of (i) having at least 70%, at least 80%, at least 90%, at least 95% or at least 99% amino acid sequence identity to (i) calculated over the full-length of (i) or calculated over at least the transmembrane domain of (i);
- (iii) the human 5T4 paralogue polypeptide having the amino acid sequence shown in FIG. 20At;
- (iv) the mouse 5T4 polypeptide having the amino acid sequence disclosed at NCBI Accession No: NP_035757, GI: 31543887;
- (v) a variant (such as a splice variant), paralogue, orthologue or derivative of any one of (iii) or (iv) having at least 70%, at least 80%, at least 90%, at least 95% or at least 99% amino acid sequence identity to any one of (iii) or (iv) calculated over the full-length of (iii) or (iv) or calculated over at least the transmembrane domain of (iii) or (iv);
- (vi) the mouse 5T4 paralogue polypeptide having the predicted amino acid sequence disclosed at NCBI Accession No: XP_486328, GI: 51829389;
- (vii) the rat 5T4 polypeptide having the amino acid sequence disclosed at NCBI Accession No: AAH87011, GI: 56268820;
- (viii) a variant (such as a splice variant), paralogue, orthologue or derivative of any one of (vi) or (vii) having at least 70%, at least 80%, at least 90%, at least 95% or at least 99% amino acid sequence identity to any one of (vi) or (vii) calculated over the full-length of (vi) or (vii) or calculated over at least the transmembrane domain of (vi) or (vii);
- (ix) the rat 5T4 paralogue having the amino acid sequence disclosed at NCBI Accession No: XP00101215, GI: 109459106
- (x) a variant (such as a splice variant), paralogue, orthologue or derivative of (ix) having at least 70%, at least 80%, at least 90%, at least 95% or at least 99% amino acid sequence identity to (ix) calculated over the full-length of (ix) or calculated over at least the transmembrane domain of (ix);
- (xi) a fragment of any one of (i)-(x) having at least 20, at least 30, at least 50, at least 100 or at least 200 amino acids. Preferably, said fragment (xi) comprises a transmembrane domain. Preferably, the 5T4 polypeptide comprises a transmembrane domain having the amino acid sequence of the human 5T4 transmembrane domain shown in FIG. 9*a*. As can be seen from FIG. 9*a*, the transmembrane domain of a 5T4 polypeptide may be readily identified by alignment with, e.g. the human 5T4 polypeptide sequence. Most preferably, the 5T4 polypeptide comprises the full-length human 5T4 polypeptide as defined in (i) above.

CXC Chemokine Receptor Polypeptide

The CXC chemokine receptor subfamily comprises seven members all of which are 7 transmembrane-spanning proteins that are G protein linked receptors for cytokines of the CXC chemokine family. The CXC chemokine receptor subfamily is currently believed to comprise CXCR1-7.

CXCR3, although expressed primarily on activated T lymphocytes and NK cells, is also expressed on some epithelial cells and endothelial cells. Binding of the ligands CXCL9, CXCL10, and CXCL11 to CXCR3 elicits an increase in intracellular $Ca^{2++}$ levels with downstream activation of phosphoinositide 3-kinase and mitogen-activated protein kinase (MAPK). Detailed signaling pathway has not yet been established, but may include the same enzymes that play a role in the signaling cascade induced by other chemokine receptors.

The main focus of analysis of CXCR3 function to date has focused on its ability to regulate leukocyte trafficking. Binding of ligands to CXCR3 induces various cellular responses, most notably integrin activation, cytoskeletal changes and chemotactic migration. In addition, CXCL9, CXCL10 and CXCL11 are commonly produced by local cells in inflammatory lesion, suggesting that CXCR3 and its chemokines participate in the recruitment of inflammatory cells. Additionally, CXCR3 has been implicated in wound healing.

CXCR3 has also been implicated in the following diseases, atherosclerosis, multiple sclerosis, pulmonary fibrosis, type 1 diabetes, autoimmune myasthenia gravis, nephrotoxic nephritis, acute cardiac allograft rejection and possibly Celiac Disease. Development of agents to block CXCR3-ligand interactions may provide new ways to treat these diseases.

CXCR7, formerly called RDC1, was originally cloned from a dog cDNA library as a putative G-protein coupled receptor (GPCR) for the vasoactive intestinal peptide hormone VIP. The binding of VIP to CXCR7 was questioned shortly after discovery and instead, it was suggested that CXCR7 might be the receptor for adrenomedullin, however this finding was also eventually dismissed, and it is now accepted that CXCR7 is a receptor for the chemokines CXCL11 and CXCL12. Translocations involving this gene and HMGA2 on chromosome 12 have been observed in lipomas and alternatively spliced transcript variants encoding the same protein isoform have been found. CXCR7 is highly conserved between mammalian species, it is highly expressed in monocytes and mature B cells and it has been demonstrated to be a co-receptor for human immunodeficiency viruses (HIV). CXCR7 null mice have been produced however most CXCR7−/− mice died at birth with ventricular septal defects and semilunar heart valve malformation.

Upon ligand binding CXCR7 fails to initiate a classical chemokine receptor signaling response, such as intracellular calcium flux or activation of kinase pathways, which may be attributable to the receptor lacking a DRYLAIV motif deemed to be important for G-protein binding/signal transduction, however CXCR7 is able to recruit beta-arrestin in response to ligand binding leading to receptor internalization and in some cases ligand sequestration. Despite an apparent lack of intrinsic signaling capability CXCR7 has consistently been associated with roles in cell survival, metabolism and proliferation which may be mediated by interactions with other receptors, indeed CXCR7 can form homo- and heterodimers with other chemokine receptors, most notably CXCR4 in which heterodimer formation alters the magnitude and dynamics of the CXCR4 signalling response to CXCL12.

CXCR4 Polypeptide

Chemokine (C—X—C motif) receptor 4 (CXCR4; NCBI GeneID: 7852) is a 7 transmembrane region chemokine receptor that binds the chemokine ligand CXCL12 (also known as SDF-1; NCBI GeneID: 6387) and is involved in the chemotactic activity of lymphocytes. As used herein the CXCR4 polypeptide may have the amino acid sequence of:

(i) the human CXCR4 polypeptide having the amino acid sequence disclosed at NCBI Accession No: CAA12166, GI: 3059120;

(ii) a variant (such as a splice variant), paralogue, orthologue or derivative of (i) having at least 70%, at least 80%, at least 90%, at least 95% or at least 99% amino acid sequence identity to (i) calculated over the full-length of (i);

(iii) the mouse CXCR4 polypeptide having the amino acid sequence disclosed at NCBI Accession No: AAH98322, GI: 68226707;

(iv) a variant (such as a splice variant), paralogue, orthologue or derivative of (iii) having at least 70%, at least 80%, at least 90%, at least 95% or at least 99% amino acid sequence identity to (iii) calculated over the full-length of (iii);

(v) the rat CXCR4 polypeptide having the amino acid sequence disclosed at NCBI Accession No: AAL47855, GI: 17902281;

(vi) a variant (such as a splice variant), paralogue, orthologue or derivative of (v) having at least 70%, at least 80%, at least 90%, at least 95% or at least 99% amino acid sequence identity to (v) calculated over the full-length of (v);

(vii) a fragment of any one of (i)-(vi) having at least 100, at least 200, at least 250, or at least 300 amino acids. Preferably, said fragment (vii) comprises a CXCL12-binding domain. Most preferably, the CXCR4 polypeptide comprises the full-length amino acid sequence of human CXCR4 as defined in (i) above.

CXCR6 Polypeptide

Chemokine (C—X—C motif) receptor 6 (CXCR6; NCBI GeneID: 10663) is a 7 transmembrane region chemokine receptor that binds the chemokine ligand CXCL16 (NCBI GeneID: 58191). As used herein the CXCR6 polypeptide may have the amino acid sequence of:

(i) the human CXCR6 polypeptide having the amino acid sequence disclosed at NCBI Accession No: O00574, GI: 3121816;

(ii) a variant (such as a splice variant), paralogue, orthologue or derivative of (i) having at least 70%, at least 80%, at least 90%, at least 95% or at least 99% amino acid sequence identity to (i) calculated over the full-length of (i);

(iii) the mouse CXCR6 polypeptide having the amino acid sequence disclosed at NCBI Accession No: NP_109637, GI: 157266315;

(iv) a variant (such as a splice variant), paralogue, orthologue or derivative of (iii) having at least 70%, at least 80%, at least 90%, at least 95% or at least 99% amino acid sequence identity to (iii) calculated over the full-length of (iii);

(v) the rat CXCR6 polypeptide having the amino acid sequence disclosed at NCBI Accession No: NP_001096057, GI: 156564361;

(vi) a variant (such as a splice variant), paralogue, orthologue or derivative of (v) having at least 70%, at least 80%, at least 90%, at least 95% or at least 99% amino acid sequence identity to (v) calculated over the full-length of (v);

(vii) a fragment of any one of (i)-(vi) having at least 100, at least 200, at least 250, or at least 300 amino acids. Preferably, said fragment (vii) comprises a CXCL16 binding domain.

Chemotaxis

As used herein, chemotaxis refers to the motile response of a cell to a chemical stimulus. In particular, the movement towards a CXCL12-expressing tissue by a CXCR4-expressing cell or movement towards a CXCL16-expressing tissue by a CXCR6-expressing cell, such as a tumour cell is contemplated. Chemotaxis may be conveniently assessed using a cellular motility based assay wherein cell migration across a transwell chamber is quantified [16; the contents of which are expressly incorporated herein by reference in their entirety].

Metastasis

As used herein, metastasis refers to the spread of cancer cells from one site to another, in particular from a first organ or part to another organ or part that is not adjacent to the first organ or part. Metastasis may involve chemotaxis of cancer cells from a first site (e.g. the site of a primary tumour)

towards a distant site. As used herein inhibition of metastasis includes not only complete or partial reduction in the spread of cancer cells, but also a reduction in the speed of cancer spread and invasion of distant sites.

Cell Proliferation and Survival

Activation of CXC chemokine receptors by their ligands also results in functional consequences other than chemotaxis, such as cell proliferation and cell survival. Upon ligand binding the chemokine receptor CXCR4 is capable of eliciting multiple cellular functions. For example, the overexpression of CXCR4 in pituitary adenomas contributes to pituitary cell proliferation and possibly adenoma development [54]. Signals from the CXCR4 receptor have also been implicated in the regulation of the Bcl-2/Bax ratio to promote dendritic cell survival in the thymus [55].

Antibody Molecule

As used herein with reference to all aspects of the invention, the term "antibody" or "antibody molecule" includes any immunoglobulin whether natural or partly or wholly synthetically produced. The term "antibody" or "antibody molecule" includes monoclonal antibodies (mAb) and polyclonal antibodies (including polyclonal antisera). Antibodies may be intact or fragments derived from full antibodies (see below). Antibodies may be human antibodies, humanised antibodies or antibodies of non-human origin. "Monoclonal antibodies" are homogeneous, highly specific antibody populations directed against a single antigenic site or "determinant" of the target molecule. "Polyclonal antibodies" include heterogeneous antibody populations that are directed against different antigenic determinants of the target molecule. The term "antiserum" or "antisera" refers to blood serum containing antibodies obtained from immunized animals.

It has been shown that fragments of a whole antibody can perform the function of binding antigens. Thus reference to antibody herein, and with reference to the methods, arrays and kits of the invention, covers a full antibody and also covers any polypeptide or protein comprising an antibody binding fragment. Examples of binding fragments are (i) the Fab fragment consisting of $V_L$, $V_H$, $C_L$ and $C_H1$ domains; (ii) the Fd fragment consisting of the $V_H$ and $C_H1$ domains; (iii) the Fv fragment consisting of the $V_L$ and $V_H$ domains of a single antibody; (iv) the dAb fragment which consists of a $V_H$ domain; (v) isolated CDR regions; (vi) $F(ab')_2$ fragments, a bivalent fragment comprising two linked Fab fragments (vii) single chain Fv molecules (scFv), wherein a $V_H$ domain and a $V_L$ domain are linked by a peptide linker which allows the two domains to associate to form an antigen binding site; (viii) bispecific single chain Fv dimers (WO 93/11161) and (ix) "diabodies", multivalent or multispecific fragments constructed by gene fusion (WO94/13804; 58). Fv, scFv or diabody molecules may be stabilised by the incorporation of disulphide bridges linking the VH and VL domains. Minibodies comprising a scFv joined to a CH3 domain may also be made.

In relation to a an antibody molecule, the term "selectively binds" may be used herein to refer to the situation in which one member of a specific binding pair will not show any significant binding to molecules other than its specific binding partner(s). The term is also applicable where e.g. an antigen-binding site is specific for a particular epitope that is carried by a number of antigens, in which case the specific binding member carrying the antigen-binding site will be able to bind to the various antigens carrying the epitope.

Variants and Uses of the Antibodies

An antibody of the invention that selectively binds to a complex comprising a 5T4 polypeptide and a CXC chemokine receptor polypeptide (e.g. a 5T4-CXCR4 complex or a 5T4-CXCR6 complex) may be used in treatment, imaging and/or diagnosis of a cancer, particularly a 5T4 polypeptide-positive, CXC chemokine receptor polypeptide-positive cancer, a metastatic cancer and/or a cancer prone to metastasis.

In one aspect, the antibodies of the present invention may be linked to a detectable moiety. The term "detectable moiety" relates to a group that, when located at the target site following administration of the antibodies of the present to a patient, may be detected, typically non-invasively from outside the body and the site of the target located. Thus, the antibodies of the present invention are useful in imaging and diagnosis. Detectable moieties are entities that are detectable by imaging techniques such as Magnetic Resonance Imaging (MRI), Magnetic Resonance Spectroscopy (MRS), Single Photon Emission Computed Tomography (SPECT) and Positron Emission Tomography (PET) and optical imaging. Preferably, imaging moieties are stable, non-toxic entities that retain their properties under in vitro and in vivo conditions. Examples of such moieties include but are not limited to radioactive moieties, for example radioactive isotopes. Suitable radioactive atoms include technetium-99m or iodine-123 for scintigraphic studies. Other readily detectable moieties include, for example, spin labels for MRI such as iodine-123 again, iodine-131, indium-111, fluorine-18, carbon-13, nitrogen-15, oxygen-17, gadolinium, manganese or iron and optical moieties which include Cy5.5 and quantum dots.

Alternatively or additionally, the antibodies of the present invention may be conjugated or linked to a therapeutically active moiety, for example a moiety that is cytotoxic. Such antibodies may be useful for targeting cancer that is spreading or prone to spread and delivering the therapeutically active moiety to cancer cells.

A further class of groups that can be incorporated into the antibodies of the present invention are affinity tags that can be introduced into the antibodies to enable them to be manipulated or detected in one or more subsequent steps. A wide range of affinity tags are known in the art suitable affinity tags include members of specific binding pairs, antibodies and antigens, biotin which binds to streptavidin and avidin, polyhistidine (e.g. hexa-His or tri-His tags) or amino di- or tricarboxylates which bind to metal ions such as $Ni^{2+}$ or $Co^{2+}$, Flag or Glu epitopes which bind to anti-Flag antibodies, S-tags which bind to streptavidin, calmodulin binding peptide which binds to calmodulin in the presence of Ca2+; ribonuclease S which binds to aporibonuclease S; and c-Myc which recognises anti-c-Myc antibody. Examples of other affinity tags that can be used in accordance with the present invention will be apparent to those skilled in the art. Antibodies including these affinity tags can be easily purified and manipulated.

The term "therapeutically active moiety" encompasses a moiety having beneficial, prophylactic and/or therapeutic properties.

In one embodiment the therapeutically active moiety is a cytotoxic chemotherapeutic agent. Cytotoxic chemotherapeutic agents are well known in the art and include anticancer agents such as:

Alkylating agents including nitrogen mustards such as mechlorethamine (HN2), cyclophosphamide, ifosfamide, melphalan (L-sarcolysin) and chlorambucil; 10 ethylenimines and methylmelamines such as hexamethylmelamine, thiotepa; alkyl sulphonates such as busulfan; nitrosoureas such as carmustine (BCNU), lomustine (CCNLJ), semustine (methyl-CCN-U) and streptozoein (streptozotocin); and triazenes such as decarbazine (DTIC; dimethyltriazenoimidazolecarboxamide);

Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2'-deoxycofonnycin). Natural Products including vinca alkaloids such as vinblastine (VLB) and vincristine; epipodophyllotoxins such as etoposide and teniposide; antibiotics such as dactinomycin (actinomycin D), daunorabicin (daunomycin; rubidomycin), doxorubicin, bleomycin, plicamycin (mithramycin) and mitomycin (mitomycin Q; enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and antbracycline; substituted urea such as hydroxyurea; methyl hydrazine derivative such as procarbazine (N-methylhydrazine, MIH); and adrenocortical suppressant such as mitotane (o, p'-DDD) and aminoglutethimide; taxol and analogues/derivatives; and hormone agonists/antagonists such as flutamide and tamoxifen.

Methods of conjugating antibodies to therapeutic agents are well known in the art.

In a further embodiment, the cytotoxic moiety is a cytotoxic peptide or polypeptide moiety by which we include any moiety which leads to cell death.

Cytotoxic peptide and polypeptide moieties are well known in the art and include, for example, ricin, abrin, *Pseudomonas* exotoxin, RNase, tissue factor and the like.

The use of ricin as a cytotoxic agent is described in Burrows & Thorpe, *P.N.A.S. USA* 90: 8996-9000, 1993, incorporated herein by reference, and the use of tissue factor, which leads to localised blood clotting and infarction of a tumour, has been described by Ran et al., *Cancer Res.* 58: 4646-4653, 1998 and Huang et al., *Science* 275: 25 547-550, 1997. Tsai et al., *Dis. Colon Rectum* 38: 1067-1074, 1995 describes the abrin A chain conjugated to a monoclonal antibody and is incorporated herein by reference. Other ribosome inactivating proteins are described as cytotoxic agents in WO 96/06641. *Pseudomonas* exotoxin may also be used as the cytotoxic polypeptide moiety (see, for example, Aiello et al, *P.N.A.S. USA* 92: 10457-10461, 1995.

Certain cytokines, such as TNFα and IL-2, may also be useful as cytotoxic and/or therapeutic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the antibody of the invention are such that a dose of more than 4000 cGy, and more preferably at least 6000, 8000 or 10000 cGy, is delivered to the target site and, preferably, to the cells at the target site and their organelles, particularly the nucleus.

The radioactive atom may be attached to the binding moiety in known ways. For example, EDTA or another chelating agent may be attached to the binding moiety and used to attach 111In or 90Y. Tyrosine residues may be labelled with 125 I or 131I.

Alternatively, any of these systems can be incorporated into a prodrug system. Such prodrug systems are well known in the art and include ADEPT systems in which an antibody according to the present invention is conjugated or conjugatable or fused to an agent capable of converting a prodrug to a cytotoxic moiety is an enzyme for use in antibody directed enzyme prodrug therapy.

The following is presented by way of example and is not to be construed as a limitation to the scope of the claims.

EXAMPLES

Materials and Methods

5T4 KO Mice

We have constructed a 5T4 KO mouse by replacing the second exon of 5T4, which encodes the entire protein, with an IRES-LacZneo reporter gene in ES cells. These cells were used to produce chimeric mice and germline progeny; 5T4 KO heterozygote mice were backcrossed to the C57BL/6 background. The null 5T4 C57Bl/6 animals are viable but adult animals show some structural disorganisation within the brain and exhibit a high frequency of hydrocephalus. At the F10 generation the frequency of hydrocephalus is 19% with the median age of death, (animals requiring termination) at 49 days, (range 33-100). We have made and characterized 5T4 KO ES cells in order to study aspects of the role of 5T4 in EMT [16] and its relationship to CD26 expression. The 5T4 null mice were used to generate monoclonal antibodies specific for m5T4 (B3F1, IgG2a; P1C9, IgG2b; B5C9, IgG1; B1C3, IgG2a; unpublished).

Primary murine embryonic fibroblasts, (MEFs) of all three genotypes were prepared from day 13 embryos following mating of male and female 5T4 heterozygote C57B16 transgenic mice by methods previously described [28; the contents of which are expressly incorporated herein in their entirety].

Cell Lines

E14TG2a [29], (herein referred to as WT-ES) and 5T4KO ES cells [16] were cultured on pre-prepared 0.1% gelatine (Sigma) coated tissue culture flasks. ES cells were grown in Knockout DMEM, (Invitrogen) supplemented with 10% Hyclone foetal calf serum, (Perbio), 2 mM L-glutamine, 1% non-essential amino acids (eBioscience), nucleosides [6 ml of the following solution/500 ml DMEM: adenosine (80 mg), guanosine (85 mg), cytidine (73 mg), uridine (73 mg) and thymidine (24 mg) dissolved in 100 ml double distilled water; Sigma], 2-mercaptoethanol (50 μM; Invitrogen) and leukaemia inhibitory factor (LIF; 1000 units/ml of ESGRO; Chemicon Int.). For differentiation cells were grown in media that was not supplemented with LIF. Media was changed daily. Chromosome numbers were routinely determined by chromosome spread following a 2 hour incubation with 0.02 μg/ml colcemid. MCF-7, MDA-MB-231 were also cultured in the DMEM, 10% FCS plus 2 mM L-glutamine and 0.1 mg/ml penicillin and streptomycin, whilst JEG-3 (all obtained from American Tissue and Cell Collection, ATCC), SupB15, Nalm-6 and Tom-1 (obtained from the Deutsche Sammlung von Mikroorganismen and Zellkulturen, DSMZ), SD1 and REH (Cancer Research UK cell bank) cell lines were cultured in RPMI supplemented with 10% FCS, 2 mM L-glutamine, 0.1 mg/ml penicillin and streptomycin. SKOV3, CAOV3, OVCAR3 and PA1 ovarian carcinoma cells were cultured as described by ATCC who supplied the lines.

Microarray Analysis

We have utilized the associated loss of pluripotency of murine ES cells with the early upregulation of 5T4 expression to search for other changes in gene expression using an Affymetrix approach [30]. The ES cells were grown with or without leukaemia inhibitory factor (LIF) for 3 days and the disaggregated cells sorted for expression, or not, of cell surface 5T4. Two ES lines were investigated with samples showing minimal intra-replicate variance and the results presented using SAM techniques with gene lists selected on the basis of False Discovery Rate (FDR). Many established transcriptional changes that occur during differentiation were identified. Data were further subjected to RMA and/or MAS5 processing and this refined the number of candidate transcript changes of interest including several not previously identified. One gene which showed significant down-regulation during differentiation was CD26, a cell surface molecule with protease activity versus CXCL12/SDF-1 [19]. Concomitantly, transcription of CXCL12 was upregulated while its receptor CXCR4 levels were unchanged. Additional analysis on the ES cell 5T4 stratified microarray dataset showed significant fold changes in the chemokine ligands CXCL10, 11 and 16 along with CXCL12. CXCL10 and 11 both bind to CXCR3 whilst CXCL11 is also known to bind to CXCR7 (as does CXCL12). CXCL16 binds exclusively to the receptor CXCR6.

Chemotaxis Assay

Chemotaxis was assessed using transwell chambers as previously described for cellular motility assays [16; the contents of which are expressly incorporated herein in their entirety] in the presence or absence of the chemokine CXCL12 (R&D systems), at a concentration of 10 ng/well for ES cell experiments, and 30 ng/well for all others. Inhibition studies were performed in the presence of 10 μM Diprotin A (Sigma) for CD26, 10 μM AMD3100 (Sigma) for CXCR4 or 10 μg/well mouse anti-CXCL12 (R&D systems) or Pertussis Toxin (Sigma, 10 ng/ml). For m5T4 specific mAb inhibition of chemotaxis or control Ig; antibodies were premixed with 50,000 differentiating WT-ES or MEF cells/ml and added to the transwell chambers as above. CXCL16 (R&D 10 ng/ml), the ligand for CXCR6 and CXCL10 (R&D 100 ng/ml), a ligand for CXCR3 were used to assess chemotaxis in undifferentiated and/or differentiating WT and 5T4KO ES cells.

ELISA for CXCL12

CXCL12 concentration in 3-day conditioned medium from undifferentiated (+LIF) or following 3 days differentiation (−LIF) of WT-ES cells was determined by murine CXCL12 specific ELISA (R&D systems).

Flow Cytometry

Cell surface detection of human and murine 5T4 was performed as previously described [15, 16; the contents of which are expressly incorporated herein in their entirety]. Cells were briefly trypsinized, washed twice in PBS and resuspended at $2\times10^6$ cells/ml in FACS buffer, (0.1% sodium azide (Sigma); 0.2% bovine serum albumin (Sigma); in PBS). Cells were labelled with antibodies at 4° C. for 1 hour at the following concentrations: mouse IgM anti-SSEA-1 directly conjugated to phycoerithrin (PE; Santa Cruz) 2 μg/ml; mouse IgM conjugated PE isotype control (Santa Cruz) 2 μg/ml; 9A7 (rat $IgG_{2A}$ anti-m5T4 [27]) 20 μg/ml; B3F1 (mouse $IgG_{2a}$ anti-m5T4) 5 μg/ml; mouse $IgG_1$ anti-h5T4 1 μg/ml; rat $IgG_{2A}$ mouse $IgG_{2a}$ and mouse $IgG_1$ isotype controls (eBioscience) 20 μg/ml, 5 μg/ml and 1 μg/ml, respectively; 1 μg/ml PE-goat anti-mouse (DAKO); rat anti-mDPIV (CD26) directly conjugated to PE 5 μg/ml (R&D systems), rat $IgG_{2A}$ isotype control-PE 5 μg/ml (R&D systems); rabbit polyclonal anti-CXCR4 (Abcam) 5 μg/ml; rat IgG2b anti murine CXCR6 (R&D, 5 μg/ml) negative control rabbit or rat immunoglobulins (Dako Cytomation) 5 μg/ml. For B-ALL labelling B cells were identified using mouse IgG1 Qdot605 anti-CD10 (4 μM) (Invitrogen) and mouse IgG1 Alexa Fluor700 anti-CD19 (6 μg/ml) (CalTag). Dead cells were identified using 7-AAD at 10 μg/ml (Biotium Inc). After washing twice in FACS buffer were fixed in 300 μl 1% p-formaldehyde.

Quantitative PCR, (qPCR)

For each RNA sample, 2 μg of total RNA was reverse transcribed according to manufacturer's instructions (Promega). Murine primers were designed using Primer Express 2.0 (read 5' to 3'; forward-F, reverse-R):

```
                                       (SEQ ID NO: 1)
m5T4-F: agctcttcggtaccctcgtc,
                                       (SEQ ID NO: 2)
m5T4-R: gttgcggttcacgcactta,
                                       (SEQ ID NO: 3)
mCD26-F: ggcaatttgtaaaaatgggatt,
                                       (SEQ ID NO: 4)
mCD26-R: aggttacataccctccatatgacc,
                                       (SEQ ID NO: 5)
mSDF-1-F: tccaaattccccagcaga,
                                       (SEQ ID NO: 6)
mSDF-1-R: ctgaacccatcgctgcttagac,
                                       (SEQ ID NO: 7)
mCXCR4-F: caggacctgtggccaagttctt,
                                       (SEQ ID NO: 8)
mCXCR4-R: agctgaggatcacggctagctt.
```

Human primers were obtained from Applied Biosystems from the Taqman Gene Expression library, h5T4 (Hs00272649_s1); GAPDH (Hs02786624_g1); and β-2 microblobulin (Hs00984230_m1). SybrGreen qPCR reactions were performed in MicroAmp optical 384-well reaction plates (Applied Biosystems). Amplifications were carried out using a 7900 ABI Prism thermocycler (Applied Biosystems) and amplification analysed with SDS 2.1 software (Applied Biosystems). Amplification curves (derivative of fluorescence intensity versus time) were made and inspected to ensure that only one peak, indicating one amplicon product, was produced. Relative fold expression was calculated using the $\Delta\Delta C_T$ approximation method with the SupB15 cell line as the internal calibrator. For testing of relative gene expression, 10 ng cDNA was used per reaction.

Westerns and Immunoprecipitation

Western blots were carried out using a BioRad Mini-PROTEAN Tetra (Thermo Fisher) supplemented with protease and phosphatase inhibitor cocktails (Thermo Fisher). RIPA buffer (50 mM Tris-Cl pH 7.4, 150 mM NaCl, 1% NP40, 0.25% Na-deoxycholate, 1 mM PMSF and protease and phosphatase inhibitor cocktail) was used as an alternative method of cell lysis. The compound PD98059 (Thermo Fisher) was applied to cells to inhibit MEK1 at 100 μM for 1 h prior to CXCL12 stimulation. Other primary antibodies used were ERK1/2, phospho-ERK1/2 (Thr202/Tyr204/Thr185/Tyr187), AKT and phospho-AKT (Thr308) (Cell Signalling Technology) at 1:1000. Following secondary antibody labelling using appropriate HRP conjugates (AbSerotec) hybridizing bands were detected using SuperSignal West Dura (Thermo Fischer). For immunoprecipitation experiments cells were lysed in M-PER (Thermo Fischer) according to manufacturer's instructions and enriched for the membrane fraction on a 45% sucrose gradient by ultracentrifugation. 100 μg of the membrane enriched fraction was incubated with 1 μg of rabbit polyclonal anti-CXCR4 (Abcam) or 1 μg of mouse anti-monoclonal h5T4 or appropriate irrelevant control antibodies for 1 hour at room temperature. A 50% slurry of Protein G beads (Amersham) was then added and incubated for 1 hour at room temperature. Beads were subsequently washed 7 times with 1 ml PBS+

0.1% Triton X-100, and then resuspended in PAGE loading buffer (Thermo Fisher), boiled for 3 minutes and loaded onto 4-15% gradient gel and processed as described for Westerns above. Gels were run in Lamelli buffer (25 mM Tris-base, 192 mM glycine, 0.1% SDS). Antibodies to CXCR7 were used in western blot analysis of PAGE separated MEF cells solubilised 1%.

Immunofluorescence In Situ. These studies were performed using methods described previously (39), with cells grown on 24 well glass bottomed plates, (Iwaki, supplied through Jencons) for ES cells the wells were pre coated with 0.1% gelatine. Primary antibodies used were rabbit anti-CXCR4, (5 μg/ml) (Abcam), rat-anti-DPIV (5 μg/ml), (R&D), mAb anti-human 5T4 (10 μg/ml,), mAb anti-m5T4, 9A7 (20 μg/ml), B3F1 (5 μg/ml), rabbit anti-CXCR7 (AbCam, 5 μg/ml), rat mAb anti-CXCR6 (R&D, 5 μg/ml), rat mAb anti-CXCR3 (R&D, 5 μg/ml), Alexa Fluor 488 mouse anti-myc tag clone 4A6 (Millipore) or appropriate isotype controls. Secondary detection was performed by incubation for 1 hour at 4° C. with species or IgG sub-class specific Alexa Fluor conjugated secondary antibodies (Invitrogen) (6 μg/ml) as appropriate for multiple antigen detection. Labelling of the endoplasmic reticulum and Golgi apparatus was performed using NBD C6-Ceramide or Endotracker, (Invitrogen, Molecular Probes) as per manufacturer's instructions. Labeling of lipid rafts was performed using cholera toxin subunit B conjugated to FITC, 1 μg/ml (Sigma) for 30 minutes at room temperature after secondary antibody labeling. F-Actin was labeled using Phaloidin-633 Alexa Fluor (Invitrogen). Microtubules were visualised by murine IgG recognizing β-tubulin (Cancer Research UK). Cells were imaged on a Zeiss Axiovert 200M with a plan-fluar ×100 1.45NA objective lens and a Roper Cascade EMCCD 512B camera. Illumination was achieved using a 300W Xenon system, (Sutter) which presented the system as an even field of illumination in addition to the appropriate neutral density and Schott filters to modulate the light source. Wavelength selection was achieved using external filter wheels, (Applied Scientific Instrumentation) and the ETSedat set, (Chroma). Data sets were captured with an axial resolution of 100 nm using the MS-2000 stage (Applied Scientific Instrumentation) and a lateral resolution of 0.1645 microns per pixel. The system was full controlled and automated via the FRAP-AI software, (MAG Biosystems/Metamorph). All of the data sets were deconvolved using Huygens (Scientific Volume Imaging) after which visualization and analysis was carried out using Imaris, (Bitplane). Colocalisation was assessed by analysis of the deconvolved images utilising ImarisColoc software (Bitplane) in manual mode. A 2D scatter plot showing intensity pairs in the image was thresholded to include only colocalized points in the three dimensional volume. This data was then extracted to a separate channel containing three dimensional colocalized points only.

5T4 Constructs

A series of 5T4 constructs were built for this study and cloned into pCMVα, and the retroviral vector SFβ91 [32] that we had previously inserted the cDNA cassette eGFP under the transcriptional control of an IRES (Clonetech). Chimeric constructs of mouse 5T4/CD44 molecules with reciprocally exchanged TM and cytoplasmic domains were engineered. CD44 molecules are 80-95 kDa transmembrane glycoproteins expressed on a variety of normal cells as well as some tumours where particular spliced forms have been associated with increased metastasis [33]. E1/E3 replication deficient recombinant adenoviral vectors were constructed by cloning of the m5T4 or h5T4 cDNA into the adenoviral shuttle vector pAdlox [34]. GFP control adenoviral vector was generated by the sub-cloning of the eGFP cDNA into the pAdlox vector. Recombinant adenoviral particles (hereafter termed RAd-m5T4, RAd-h5T4 and RAd-GFP) were generated by co-transfection of CRE8 cells with the pAdlox vector and adenovirus C5 DNA as described [34]. High-titre stocks were prepared by double caesium chloride density gradient separation and titred as previously described [31]. Viral stocks were found to be free of replication-competent adenovirus using a supernatant rescue assay using HeLa cells able to detect 1 replication-competent virus within $10^9$ recombinant viruses [31]. A multiplicity of 30 infectious units per cell led to 100% of cells expressing m5T4 or h5T4 or GFP at 48 hours as assessed by FACS and when other biological assessments were made. Several putative specific shRNA plasmids against h5T4 and encoding EGFP (Superarray Biotech) were transfected (by calcium phosphate) into SKOV3 ovarian carcinoma cells. After 3 days, GFP positive cells were FACS sorted and assessed for 5T4 expression and chemotaxis to CXCL12.

Analysis of Paediatric Acute Leukaemia Samples Diagnostic bone marrow from children with acute leukaemia was obtained and processed as described previously [35, 36]. Sample hybridization was performed using the Human Genome U133 GeneChip set (Affymetrix, n=156) and supervised gene expression analysis was carried out using the GeneSpring platform (Agilent Technologies UK Ltd) [35, 36]. For validation of 5T4 expression using the quantitative polymerase chain reaction (n=15), 0.5 μg of total RNA (amount of RNA confirmed to be both within the range of the linearity and the efficiency of the reaction) was reverse transcribed (Promega) as above with β-2-microglobulin and GAPDH as internal reference controls. We evaluated 5T4 specific FACS or immunofluorescence labelling of cytospins in a pilot study. The nine patients analysed for expression of 5T4 came from diagnostic material obtained from participants in a phase II study. These are multiply treated patients most with more than one relapse.

None of these patients had CNS disease as this was an exclusion criteria.

Statistical Analysis

Quoted errors refer to standard errors of the mean. Statistical significance was calculated by either two-tailed unpaired Student's t-test, ANOVA, or non-parametric linear regression (Kendall correlation) test as appropriate.

Sequence and Sequence Alignments

Amino acid sequences were derived from the NCBI database as referenced herein. Sequence alignments were performed using the general purpose multiple sequence alignment program ClustalW2 (EMBL-EBI) and were edited using GeneDoc, a multiple sequence alignment editor, analyser and shading utility for Windows (NRBSC).

RT-PCR: Isolation hPL5 cDNA

To generate cDNA, 2 μg of total RNA was subjected to reverse transcription with the use of M-MLV reverse transcriptase (#M170A), dNTPs (#U1201, #U1211, #U1221, #U1231), RNase inhibitors (#N2511) and oligo$(dT)_{15}$ primer (#C1101), all from Promega, strictly following manufacturer's protocol. Negative samples contained no enzyme.

1 μL of the prepared cDNA was subjected to each PCR reaction, using the following program: 94° C. for 5 minutes, series of cycles of: 94° C., 60° C., 72° C. for 30 s, 30 s, 1 minute, respectively, 72° C. for 5 minutes. The number of cycles was 40 for all reactions, except for EEF2 gene with cDNA as template. For EEF2 amplification Taq polymerase was used (#11146173001), and for the GC-rich paralogue sequence was amplified with the use of GC-rich PCR system (#12140306001), both from Roche. Primers were as follows:

| Primer | sequence (5'-3') | |
|---|---|---|
| EEF2-F | CAT GGA GCC CAT CTA CCT TGT G | (SEQ ID NO: 13) |
| EEF2-R | GCT GTT GTC GAA GGG GTC TCC G | (SEQ ID NO: 14) |
| 5T4para-TM-F | GCG GCT TCG CTG CGC GGA C | (SEQ ID NO: 9) |
| 5T4para-TM-R | ATC TGG TCC CGG CAC GCC TCG | (SEQ ID NO: 10) |

Expression and Analysis of a Fusion Protein of Either Human or Murine PL5 with Myc-Tag HEK 293 cells were transfected (by calcium phosphate) with the pCMV mammalian expression vectors encoding a fusion protein of either human or murine PL5 with myc-tag located directly downstream of the predicted signal peptide. Three days post transfection cells were processed for immunocytochemistry as previous described and immunostained with Alexa Fluor® 488-labelled mouse anti-myc antibody (Millipore).

Example 1

Differentiating mES Cells Show 5T4-Dependent CXCL12 Chemotaxis

Figure 1B:
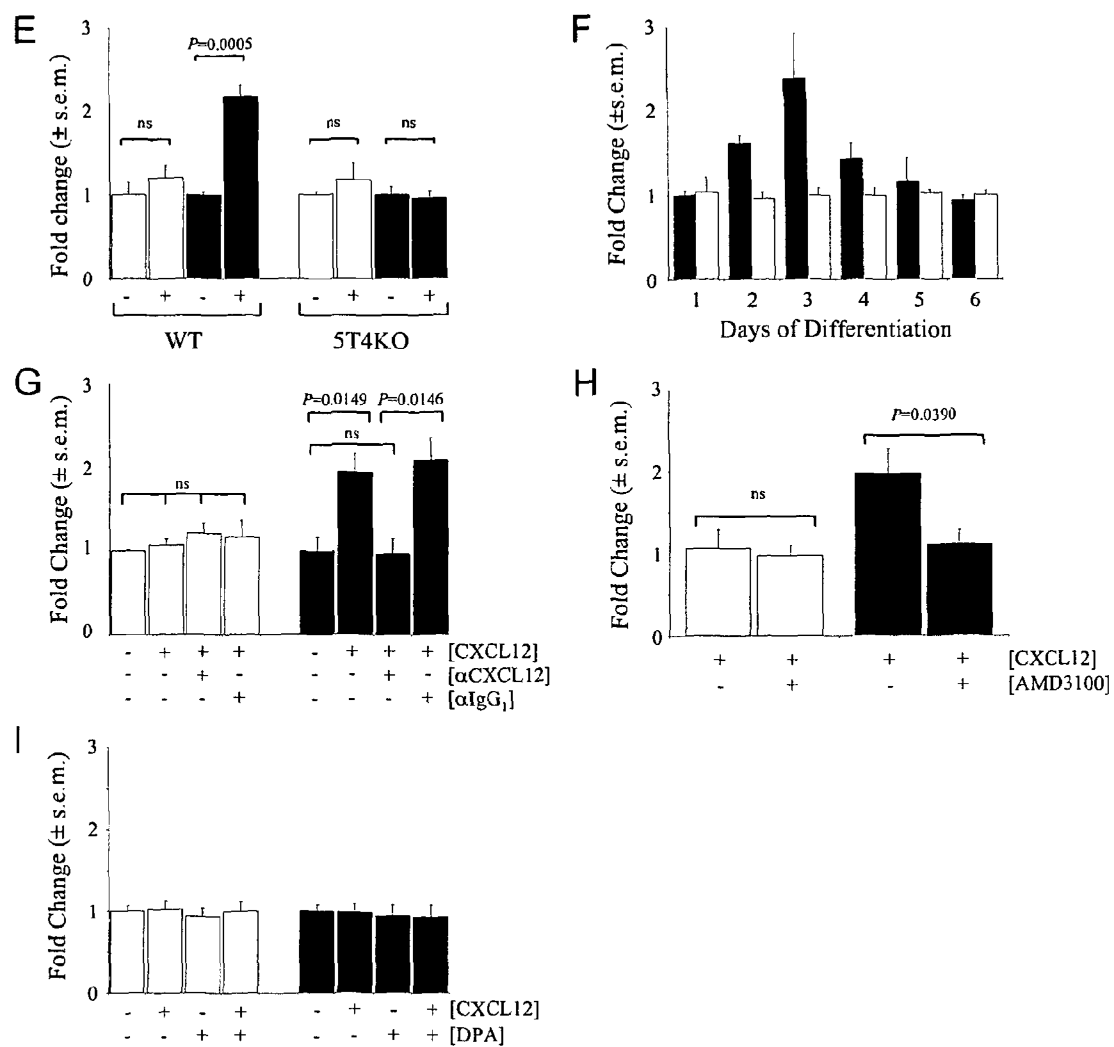
Figure 2:
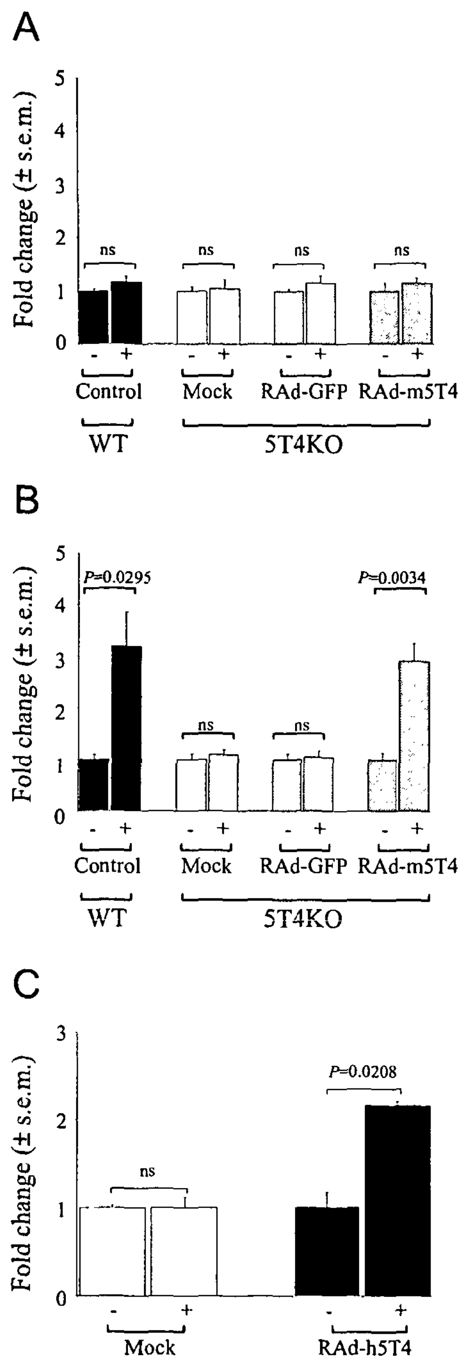
FIGS. 2A-2C: 5T4 restores CXCL12 dependent chemotaxis in differentiating 5T4KO-ES cells. Panel A, Undifferentiated 5T4KO ES cells forced to express 5T4 following infection with RAd-m5T4, (multiplicity of infection=30, dark grey columns) show no CXCL12 dependent chemotaxis comparable to undifferentiated WT-ES cells (black columns), mock (white columns), or RAd-eGFP (light grey columns) infection. Panel B, Differentiating 5T4KO ES cells with 5T4 expression restored by RAd-m5T4, (multiplicity of infection=30, dark grey columns) show CXCL12 chemotaxis comparable to differentiating WT-ES cells (black columns) but not following mock (white columns), or RAd-eGFP (light grey columns) infection. Panel C, Differentiating 5T4KO ES cells chemotactic response to CXCL12 is also restored following infection with a recombinant adenovirus encoding human 5T4 (multiplicity of infection=30, black columns), (−=no CXCL12, +=10 ng/well CXCL12). All chemotactic experiments were performed at least three times with triplicates for each condition.

A comparative microarray of undifferentiated (5T4 −ve) and early differentiating (5T4 +ve) mES cells identified a significant downregulation of CD26, upregulation of CXCL12 but no change in the CXCR4 transcripts [30]. These data were confirmed by qPCR (FIG. 1A) and FACS analysis showed that as the ES cells differentiate cell surface expression of CD26 decreases while 5T4 increases; by contrast the pluripotent ES marker SSEA-1 did not significantly change over this time (FIG. 1B). The adherent cells were harvested for FACS analysis using trypsin-EDTA and CXCR4 is trypsin sensitive so its cell surface expression could not be accessed by this method. Western blot analysis shows there is no change in the total CXCR4 expression upon differentiation of either WT or 5T4KO ES cells (FIG. 1C). Increased CXCL12 was detected in the culture medium by ELISA after 3 days of differentiation (74±4 vs 180±9 pg/ml) (FIG. 1D). To examine biological response to CXCL12, WT-ES and 5T4KO ES cells were tested for CXCL12 chemotaxis before and after differentiation. Both WT-ES and 5T4KO undifferentiated ES cells showed no chemotaxis towards CXCL12. In contrast differentiating WT-ES showed a >2-fold response but the differentiating 5T4KO ES did not (FIG. 1E); the latter cells can undergo EMT although their motility is reduced [16]. This was not simply a result of delayed kinetics in response since daily testing for up 6 days still provided no evidence for CXCL12 dependent chemotaxis (FIG. 1F). The differentiated WT-ES cell chemotaxis to CXCL12 was blocked by specific antibodies to the chemokine (FIG. 1G) or by blocking the CXCR4 receptor with the inhibitor AMD3100 (FIG. 1H). The lack of chemotaxis of differentiating 5T4KO ES cells was not the result of continued CD26 activity destroying CXCL12, since preincubation with the competitive CD26 inhibitor diprotin A did not restore chemotactic behaviour (FIG. 1I). To test whether 5T4 might play a role in CXCL12 dependent chemotaxis, undifferentiated and differentiating 5T4KO ES cells were infected with RAd-m5T4 or RAd-GFP control virus. FIG. 2A shows no change in chemotaxis of either WT or 5T4KO undifferentiated ES infected with the different vectors. FIG. 2 B shows that expression of m5T4 in differentiating 5T4KO ES cells restores CXCL12 chemotaxis comparable to that of differentiating WT-ES cells. A recombinant adenovirus encoding human 5T4 also restored chemotaxis (FIG. 2C).

Example 2

Cellular Location of CXCR4 in Differentiating ES Cells

Figure 3:
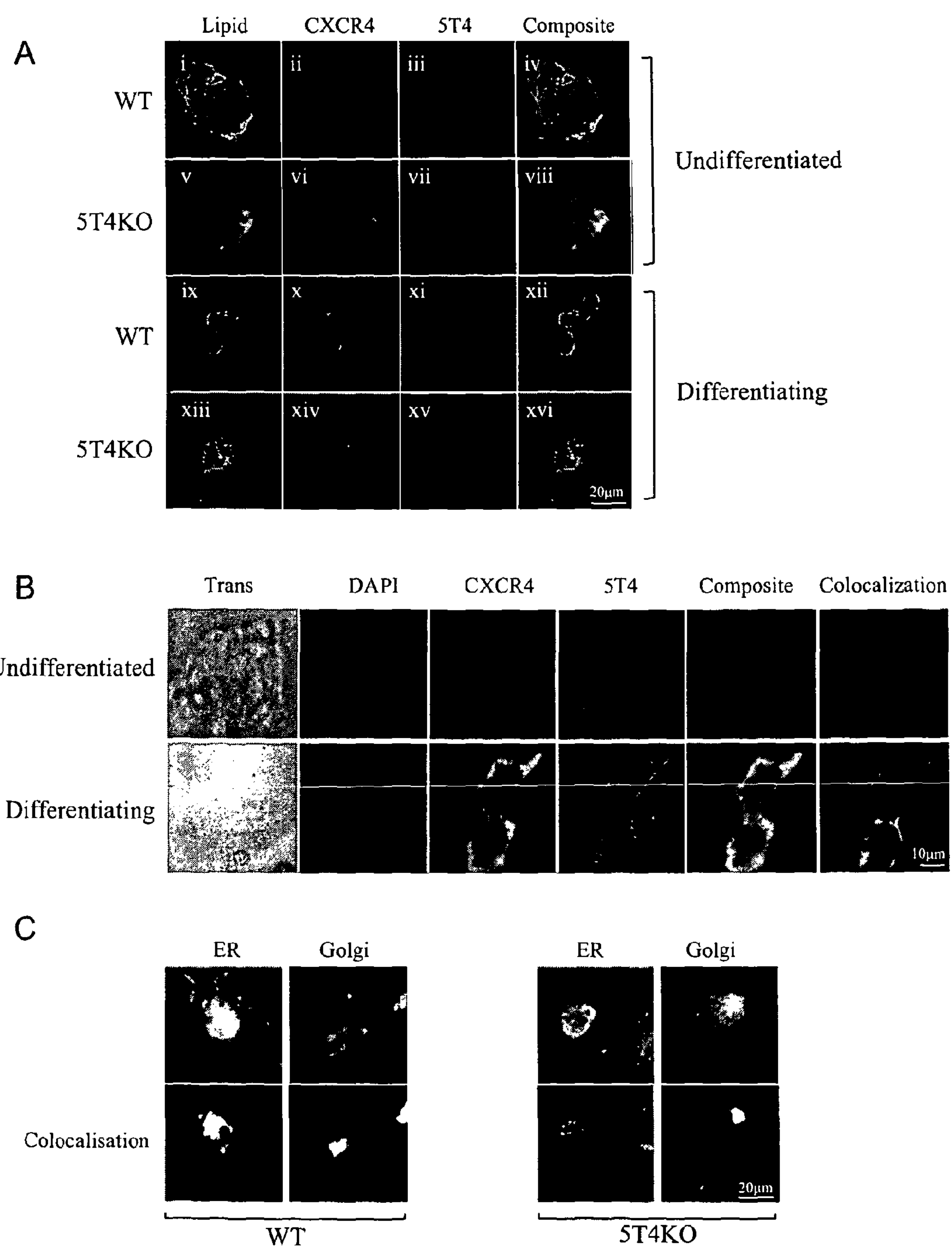
FIGS. 3A-3C: Cellular location of CXCR4, 5T4 in undifferentiated and differentiating WT and 5T4KO-ES cells. Panel A, shows lipid rafts in the membrane of all cells (green: i, v, ix, xiii); CXCR4 (red) is intracellular in undifferentiated WT-ES and all 5T4KO ES cells (ii, vi) and cell surface 5T4 (blue) is only expressed on differentiation of WT-ES cells (xi). The composite images show co-localization of 5T4 and CXCR4 (purple) including in lipid rafts (white) in differentiating WT-ES cells (xii) but no other cells (iv, viii, xvi). Panel B, RAd-m5T4 infection of 5T4KO ES cells leads to cell surface expression of both 5T4 (red) and CXCR4 (green) only in differentiating cells but not in undifferentiated cells which are seen to co-localize in the composite (yellow). Colocalisation was assessed by analysis of the deconvolved images utilising ImarisColoc software (Bitplane) in manual mode. A 2D scatter plot showing intensity pairs in the image was thresholded to include only colocalized points in the three dimensional volume. This data was then extracted to a separate channel containing three dimensional colocalized points only. RAd-GFP showed no effect on CXCR4 expression (not shown). Panel C, Upper panels, Double labeling of WT or 5T4KO ES cells with either NBD $C_6$-Ceramide (Golgi) or Endotracker (ER) (both red) shows that in the absence of 5T4, CXCR4 (green) accumulates predominately in the Golgi and to a lesser extent the smooth ER (yellow) whereas cell surface labeling is apparent only in the differentiating WT-ES cells. Lower panels, colocalisation channel of CXCR4 and the organelles.

Following LIF withdrawal, both WT and 5T4KO ES cells undergo an EMT with cells eventually becoming dispersed with an arborized morphology. The expression and cellular localization of 5T4 and CXCR4 molecules before and after differentiation was determined by immunofluorescence of fixed cells grown on glass plates (FIG. 3A). Undifferentiated WT-ES cells are 5T4-negative with CXCR4 expression low and intracellular; following differentiation both molecules can be detected at the cell surface with some areas of co-localization. By contrast, differentiated 5T4KO ES cells show only intracellular CXCR4 expression. It is apparent that at least some 5T4 and CXCR4 molecules co-localize to lipid rafts in differentiating WT but not 5T4KO differentiating ES cells where CXCR4 remains intracellular. However, when differentiating 5T4KO ES cells are infected with RAd-m5T4, CXCR4 can be detected at the cell surface co-localized with 5T4 molecules (FIG. 3B). RAd-m5T4 infected undifferentiated ES cells show only limited CXCR4 and 5T4 surface expression in a few outer cells of undifferentiated ES colonies. These are most likely spontaneously differentiating cells suggesting that differentiation is a necessary cofactor for coexpression of CXCR4 and 5T4 at the cell surface. In differentiating 5T4KO ES cells, CXCR4 accumulated in the Golgi and to a lesser extent in smooth endoplasmic reticulum (FIG. 3C). These data are consistent with 5T4 molecules being necessary for the surface expression of the CXCR4 receptor and chemotaxis to CXCL12 in differentiating ES cells.

Example 3

Role of 5T4 Expression in the CXCL12/CXCR4 Axis in Mouse Embryo Fibroblasts

A 5T4 dependency for CXCR4-mediated chemotaxis is also apparent in MEFs as shown by: (1) a 5T4 gene dose influence on CXCL12 chemotaxis in WT, heterozygote and KO MEFS (FIG. 3*a*); (2) the restoration of the chemotactic response of 5T4 null MEF by RAd-m5T4 (FIG. 3*b*); and (3) the co-localization of some CXCR4 molecules with typical punctuate 5T4 cell surface expression in WT MEFs while 5T4 null MEFs show only intracellular CXCR4 (FIG. 3*c*) that can be rescued at the cell surface by RAd-m5T4 (FIG. 3*d*).

We next examined the role of 5T4 in the CXCL12/CXCR4 axis by analyzing CXCL12-induced activation of key intracellular signalling effectors ERK and AKT in both WT and 5T4 null MEFs (FIG. 3*e*). These data demonstrate that in WT MEFs classical signal transduction pathways for the CXCL12/CXCR4 axis are active but in the absence of 5T4 both ERK and AKT pathways are disrupted and the phosphorylation status of these effectors is no longer responsive to CXCL12.

Example 4

The Transmembrane Domain of 5T4 is Necessary for CXCR4 Cell Surface Expression

In the embryonic cells investigated it appears that cell surface expression of, and chemotactic response through, CXCR4 can be regulated by 5T4 expression. A series of murine 5T4 gene constructs were designed and cloned into a retrovirus (also encoding eGFP as a reporter gene) to examine the role of the extracellular, transmembrane and cytoplasmic domains of 5T4 molecules and the cell surface expression of CXCR4. 5T4 null MEFs were infected with the retroviral constructs and cells were examined for both eGFP expression and CXCR4 localization by immunofluorescence (FIG. 6). 5T4 null fibroblasts (controls, FIG. 6A, panel i-iv); and infected with retroviruses encoding 5T4 full length (FIG. 4*a*, panels v-viii) showed surface expression of CXCR4. However, the 5T4 extracellular domain was insufficient (FIG. 6A, panels ix-xii) and the cytoplasmic domain unnecessary (FIG. 6A, panels xiii-xvi) for CXCR4 expression on the cell surface. To test whether the 5T4 transmembrane Domain™ was necessary and sufficient for cell surface CXCR4 expression, chimeric constructs of mouse 5T4/CD44 molecules with reciprocally exchanged TM and cytoplasmic domains were engineered. 5T4KO MEFs constitutively express mCD44 with no effect on surface CXCR4 expression. Importantly, cells infected with the retrovirus encoding the 5T4 extracellular domain fused to the transmembrane and cytoplasmic region of CD44 exhibited no cell surface expression of CXCR4 (FIG. 6A, panels xvii-xx), whereas the reciprocal construct did promote cell surface expression of CXCR4 (FIG. 6A, panels xxi-xxiv). Similar results were obtained with transfection of the plasmid constructs. These data suggest that the 5T4 transmembrane region is critical for either the transport and/or the stabilization of CXCR4 at the cell surface. Importantly the data shown in FIG. 6B illustrate that the chemotactic response is congruent with the ability of the constructs to promote cell surface expression of CXCR4.

Example 4A

Effects of Cytoskeleton, Microtubule and Golgi Disruption on the Co-Localization Pattern of 5T4 and CXCR4

Primary murine embryonic fibroblasts were assessed for their pattern of 5T4 and CXCR4 expression by immunofluorescence following disruption of the cytoskeleton, Golgi or microtubules for 24 hours with cytochalasin D, brefeldin A or nocodazole respectively. Cytoskeleton, Golgi and microtubule disruption was determined by immunofluorescence with AlexaFluor 633 conjugated phalloidin, BODIPY labeled NBD C6 ceramide and anti-tubulin antibodies respectively. Untreated primary murine embryonic fibroblasts exhibit cell surface expression of both 5T4 and CXCR4 with considerable colocalisation (FIG. 7). After cytochalasin treatment, there were no detectable differences in the cell surface expression or colocalisation of 5T4 and CXCR4 in comparison to untreated controls. Brefeldin A reduced levels of cell surface expression of both antigens and all residual CXCR4 or 5T4 labeling was colocalized at cell surface. One hour after brefeldin A washout, cell surface expression of both antigens had returned to normal levels with marked cell surface colocalisation. Following nocodazole treatment there was no cell surface detection of CXCR4 but accumulation intracelluarly while 5T4 remained detectable at the cell surface albeit at a diminished level. One hour after nocodazole washout both antigens were detectable at the cell surface with marked colocalisation. Clearly plasma membrane detection of co-localized 5T4/CXCR4 molecules is dependent on microtubules and the molecules are not obligatorily associated at the Golgi. Disruption of the Golgi or the actin cytoskeleton per se does not disrupt all 5T4/CXCR4 co-localization at the plasma membrane.

Example 4B

Inhibition of Chemotaxis by Monoclonal Antibodies Recognizing 5T4

We assessed four different monoclonal antibodies recognizing distinct epitopes in the proximal and distal LRR domains of m5T4 (FIG. 8). Each antibody showed different affinities in a m5T4 specific ELISA [27] decreasing in the order B3F1, P1C9, B5C9 and B1C3. The chemotactic migration exhibited by differentiating WT-ES cells towards CXCL12 was abolished in the presence of mAb B1C3 but not P1C9 while B3F1 and B5C9 showed less but still significant inhibition of the chemotactic response. Similar results were exhibited by primary WT mouse embryo fibroblasts. Thus the chemotactic response of both differentiated ES cells and MEF can be blocked by some but not all antibodies recognizing distinct parts or epitopes of m5T4 molecules. These data suggest that 5T4 contributes to functional integrity of the CXCR4 receptor expression at the cell surface. Mechanisms could include modulation of 5T4 molecules from the cell surface, and/or allosteric effects on CXCR4 ligand binding and/or direct blocking of ligand binding Example 5

Figure 9:
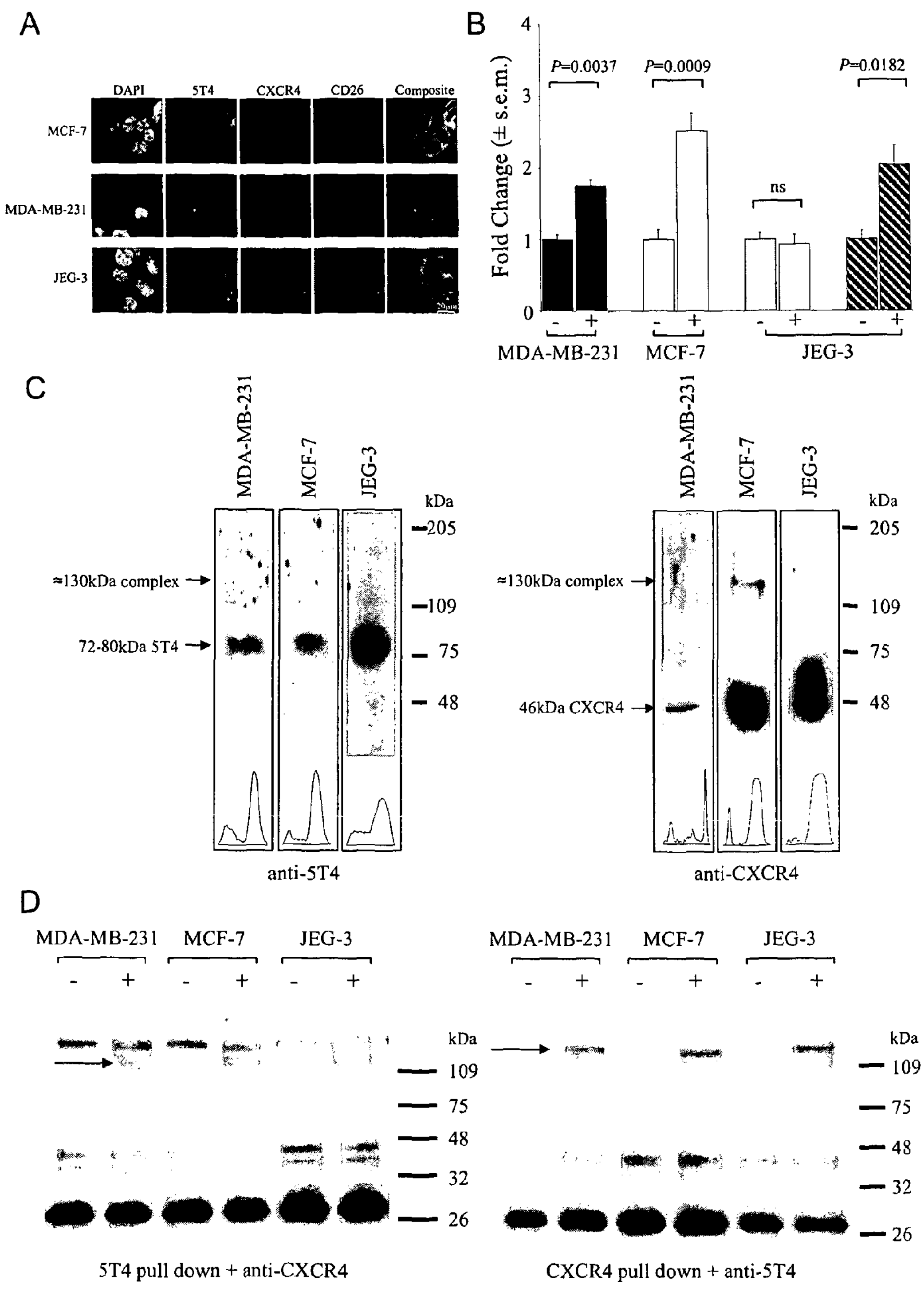

Expression and Molecular Interaction of CXCR4 and 5T4 Molecules in Human Tumour Cells We next investigated the relationship between expression of 5T4, CXCR4 and chemotaxis in human tumour cell lines. The breast cancer cell lines MCF-7 and MDA-MB-231, and a choriocarcinoma cell line, JEG-3, exhibited CXCL12-mediated chemotaxis. All the lines showed cell surface expression of 5T4 and CXCR4 but only the JEG-3 cells showed high levels of CD26 (FIG. 9A) and in JEG-3, chemotaxis was only evident in the presence of the specific CD26 inhibitor (FIG. 9B).

Unreduced solubilised membrane fractions from these cell lines were subject to PAGE and Western blotted with 5T4 and CXCR4 specific antibodies. FIG. 9C shows that in addition to the expected molecular weights of 5T4 (72-80 kDa) and CXCR4 (46 kDa) a "complex" of approximately 130 kDa was detected with either antibody probe. When membrane proteins were solubilised with RIPA buffer the complex was no longer detectable (not shown). To further investigate possible physical interaction of 5T4 and CXCR4, solubilised membranes were subject to pull down with antibodies against 5T4 or CXCR4 followed by native-PAGE and immunodetection with anti-CXCR4 or anti-5T4 respectively. For the anti-5T4 and CXCR4 pull downs but not the controls, anti-CXCR4 or anti-5T4 probes detected molecules migrating with an apparent molecular weight of ≈130 kDa from each of the tumour lines (FIG. 9D). Under reducing conditions, the epitope recognized by 5T4 antibodies is destroyed but CXCR4 at 46 kDa is detectable on the reduced gels of the 5T4 pulldown (not shown). These data suggest the existence of a complex between 5T4 and CXCR4 molecules in the membrane of human tumour cells which can survive non-ionic detergent solubilisation. These interactions appear to be necessary for a functional response to the chemokine CXCL12 at least in some cell types. FIG. 10 shows expression of 5T4, CXCR4 and chemotaxis in human ovarian carcinoma cell lines SKOV3, CAOV3, OVCAR3 and PA1. All the lines showed cell surface expression of 5T4 and CXCR4 with colocalization (FIG. 10A). Unreduced solubilised membrane fractions from these cell lines were subject to PAGE and Western blotted with 5T4 and CXCR4 specific antibodies FIG. 10B shows that in addition to the expected molecular weights of 5T4 (72-80 kDa) and CXCR4 (46 kDa) a "complex" of approximately 130 kDa was detected with either antibody probe (FIG. 10B). SKOV3 and CAOV showed significant CXCL12 chemotaxis which was further enhanced in the presence of the inhibitor of CD26; chemotaxis was less marked in OVCAR3 and PA1 cells (FIG. 10C). The level of chemotaxis is correlated to the intensity of cell surface colocalized 5T4/CXCR4 expression. Indeed, SKOV3 cells transfected with a 5T4 specific but not control shRNA exhibited downregulation of cell surface expression of 5T4 (FIG. 11A) and no chemotaxis towards CXCL12, (FIG. 11B).

Without wishing to be bound by any theory, it is presently believed that it is possible that there are additional molecules with related or unrelated mechanisms which can allow functional CXCR4 chemokine receptor expression.

Example 6

5T4 and CXCR4 Expression in Human B-ALL

CXCR4 is expressed by most leukemic cells of B-cell origin and a functional CXCR4 receptor appears to be critical for homing of pre-B acute lymphoblastic cells to the marrow niche [37]. 5T4, on the other hand, is not thought to be expressed by hematopoietic cells [2]. Our results indicate a functional synergy between 5T4 and CXCR4. We therefore looked for a correlation between 5T4 and CXCR4 expression in patients with pre-B ALL by interrogating data obtained from previous global gene expression profiling [35, 36].

Figure 4:
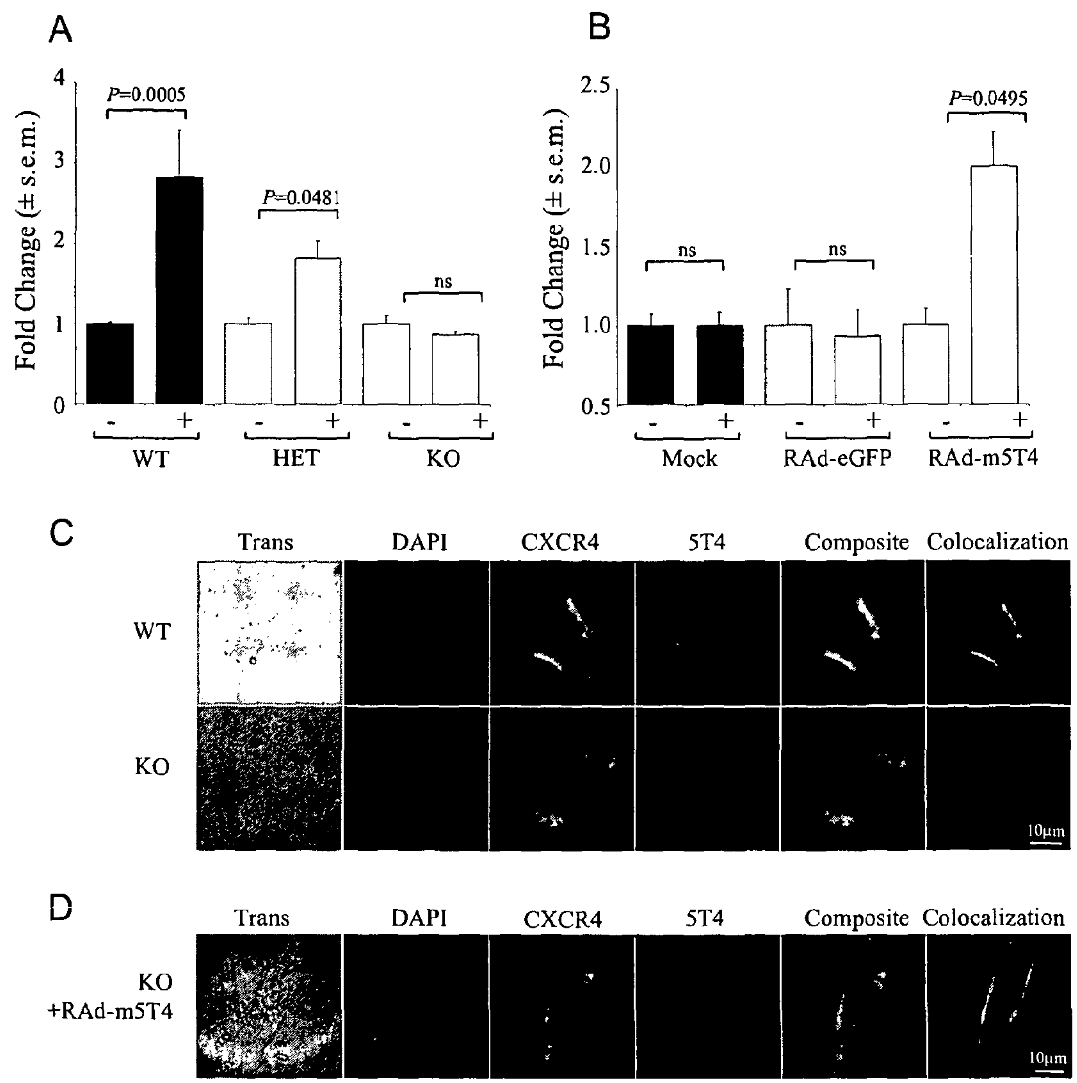
FIGS. 4A-4D: Role of 5T4 expression in the CXC12/CXCR4 axis in MEFs. Panel A, MEFs derived from wild-type, (WT, black columns), 5T4 heterozygote, (HET, grey columns) and 5T4 null, (KO, white columns) mice show 5T4 gene dose related CXCL12chemotaxis. Panel B, Chemotaxis of 5T4KO MEFs following mock infection, (black columns), or infection with RAd-eGFP, (grey columns), or RAd-m5T4, (white columns), CXCL12 chemotaxis is only restored by RAd-m5T4. (+ or −30 ng/m1 CXCL12). All chemotactic experiments were performed at least three times with triplicates for each condition. Panel C, Pattern of expression of CXCR4, (green) and 5T4, (red) in WT and 5T4KO MEFs. In WT cells, CXCR4 and 5T4 are seen at the cell surface and clearly co-localize (yellow, composite) while in 5T4KO cells CXCR4 is located intracellularly around the nucleus; compare to DAPI labeling (blue). Colocalisation was assessed by analysis of the deconvolved images utilising ImarisColoc software (Bitplane) in manual mode. A 2D scatter plot showing intensity pairs in the image was thresholded to include only colocalized points in the three dimensional volume. This data was then extracted to a separate channel containing three dimensional colocalized points only. Panel D, 5T4KO MEFs infected with RAd-m5T4exhibit cell surface expression of both 5T4 (green) and CXCR4 (red) also displayed by colocalization. This is consistent with the requirement for 5T4 to enable functional expression of CXCR4. RAd-GFP had no effect on CXCR4 expression (not shown).
Figure 12:
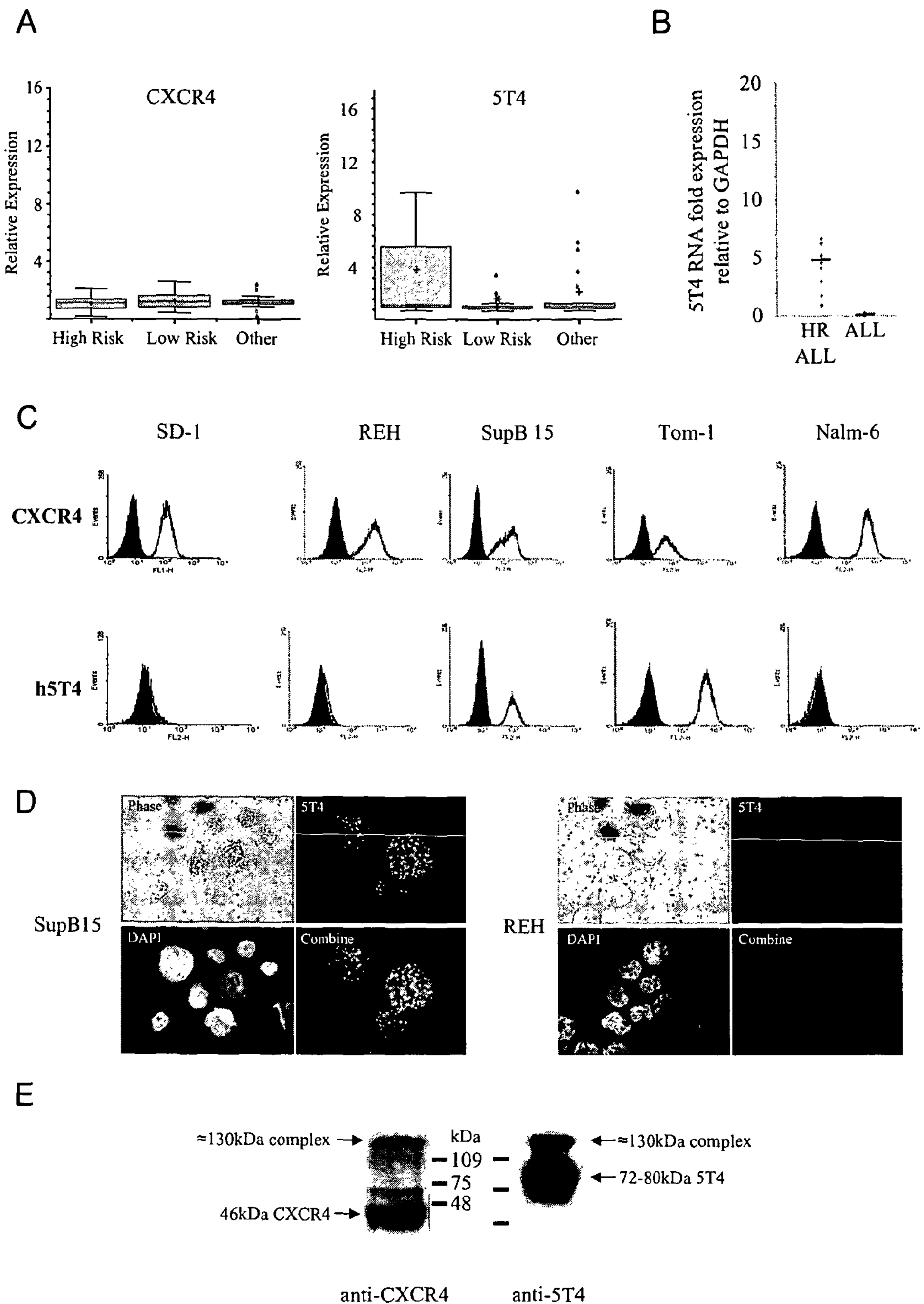

As shown in FIG. 12A, 5T4 but not CXCR4 transcription is significantly higher in high risk cytogenetic subtypes of pre-B ALL. It is these high risk patients who have a greater risk of therapeutic failure and often have disease in extramedullary sites which express CXCL12. The quantitative microarray results were validated by qPCR with RNA isolated from 15 available patients (range 1.0-9.7, median 3.4) (FIG. 12B). Significant correlation of the two measures was confirmed by Kendall's rank correlation analysis (tau b=0.785, $P<0.0001$).

We next screened five pre-B ALL cell lines SD1, REH, SupB15, Tom-1 and Nalm-6 for CXCR4 and 5T4 expression using FACS. SD1, SupB15 and Tom-1 are examples of high risk cytogenetic subtypes as they have a Philadelphia translocation (Ph+). REH is an example of a low risk cytogenetic subtype as it contains a TEL-AML1 fusion. Nalm-6 has an unusual translocation of unknown risk. While all cell lines were positive for CXCR4, only SupB15 and Tom-1 cells co-expressed 5T4 (sub-population) (FIG. 12C). The levels of 5T4 expression appears to vary with culture condition but Tom-1 are 100% positive while SupB15 generally show a subpopulation of antigen positive cells. 5T4 immunofluorescence labelling of cells analysed as cytospins showed no specific labelling of either SD1, Nalm-1 (not shown) or REH cells (FIG. 12D), a subpopulation of SupB15cells (FIG. 12D) and all Tom-1 cells (not shown). Unreduced solubilised membrane proteins from SupB15 were separated by PAGE and probed for 5T4 and CXCR4 expression. In addition to CXCR4 and 5T4 specific bands detected with the specific probes, an ≈130 kDa band was seen with both reagents consistent with the presence of a complex between the molecules (FIG. 12E); RIPA buffer solubilised membranes did not allow detection of the complex, only the individual molecules (not shown).

We evaluated 5T4 specific FACS or immunofluorescence labelling of cytospins in a pilot study. The nine patients analysed for expression of 5T4 came from diagnostic material obtained from participants in a phase II study. These are multiply treated patients most with more than one relapse. None of these patients had CNS disease as this was an exclusion criteria. This population was chosen as a first step in validation of the assay in human cells. FIGS. 13A and B illustrates the potential to phenotype 5T4 expression on the surface of lymphoblasts by FACS and/or using immunofluorescent labelling of cytospins.

These findings suggest a role for 5T4 in chemotaxis of leukaemic cells. 5T4/CXCR4 positive pre B-ALL cells of high risk cytogenetic type may have enhanced ability to home to extramedullary compartments producing CXCL12.

Example 7

Cellular Location of CXCR6 in Differentiating ES Cells

Following LIF withdrawal WT ES cells undergo an EMT with cells eventually becoming dispersed with an arborized morphology. The expression and cellular localization of 5T4 and CXCR6 molecules before and after differentiation was determined by immunofluorescence of fixed cells grown on glass plates (FIG. 10A). Undifferentiated WT-ES cells are 5T4-negative with CXCR6 expression low and intracellular; following differentiation both molecules can be detected at the cell surface with some areas of co-localisation.

This phenomenon was also evident in WT murine embryonic fibroblasts with co-localisation of 5T4 and CXCR6 on the cell surface. By contrast, 5T4KO MEFs cells show only intracellular CXCR6 expression.

We next investigated the relationship between expression of 5T4, and CXCR6 in human tumour cell lines. The breast cancer cell line MCF-7, and a choriocarcinoma cell line, JEG-3. Both lines showed cell surface expression of 5T4 and CXCR6 (FIG. 14A). Analysis of cell surface expression of CXCR6 by flow cytometry confirmed results obtained by immunocytochemistry with no evidence of CXCR6 cell surface expression on 5T4KO MEFs (FIG. 14B).

To examine whether cell surface expression of CXCR6 was biologically functional, differentiated WT ES cells were placed on a chemotactic gradient either towards the chemokine CXCL12 (as a positive control) or CXCL16. WT ES cells exhibited an approximately 2-fold increase in chemotaxis towards CXCL16 (FIG. 14C).

Example 7A

5T4 is not Required for Chemotactic Response to CXCL10 nor CXCR3 Surface Expression on ES Cells In contrast to CXCR4 and CXCR6, CXCR3 expression and its response to the chemokine CXCL10 does not require 5T4 expression. Thus, cell surface expression of CXCR3 is evident in both WT and KO undifferentiated ES cells (FIG. 15A). However chemotactic response to CXCL10 is not seen in undifferentiated WT and 5T4KO ES cells but is apparent in differentiating WT and 5T4KO ES cells (FIG. 15B). Further analysis of undifferentiated ES cells treated with the inhibitor Diprotin A (10 μM) suggests that lack of response in undifferentiated ES cells is due to CD26 activity (FIG. 15C). Treatment of both WT and KO differentiating ES cells with the inhibitor pertussis toxin (10 ng/ml) shows that Gi protein-chemokine interaction occurs irrespective of 5T4 expression at the cell surface allowing CXCL10 chemotaxis.

Example 7B

5T4 is not Required for CXCR7 Surface Expression

Figure 16:
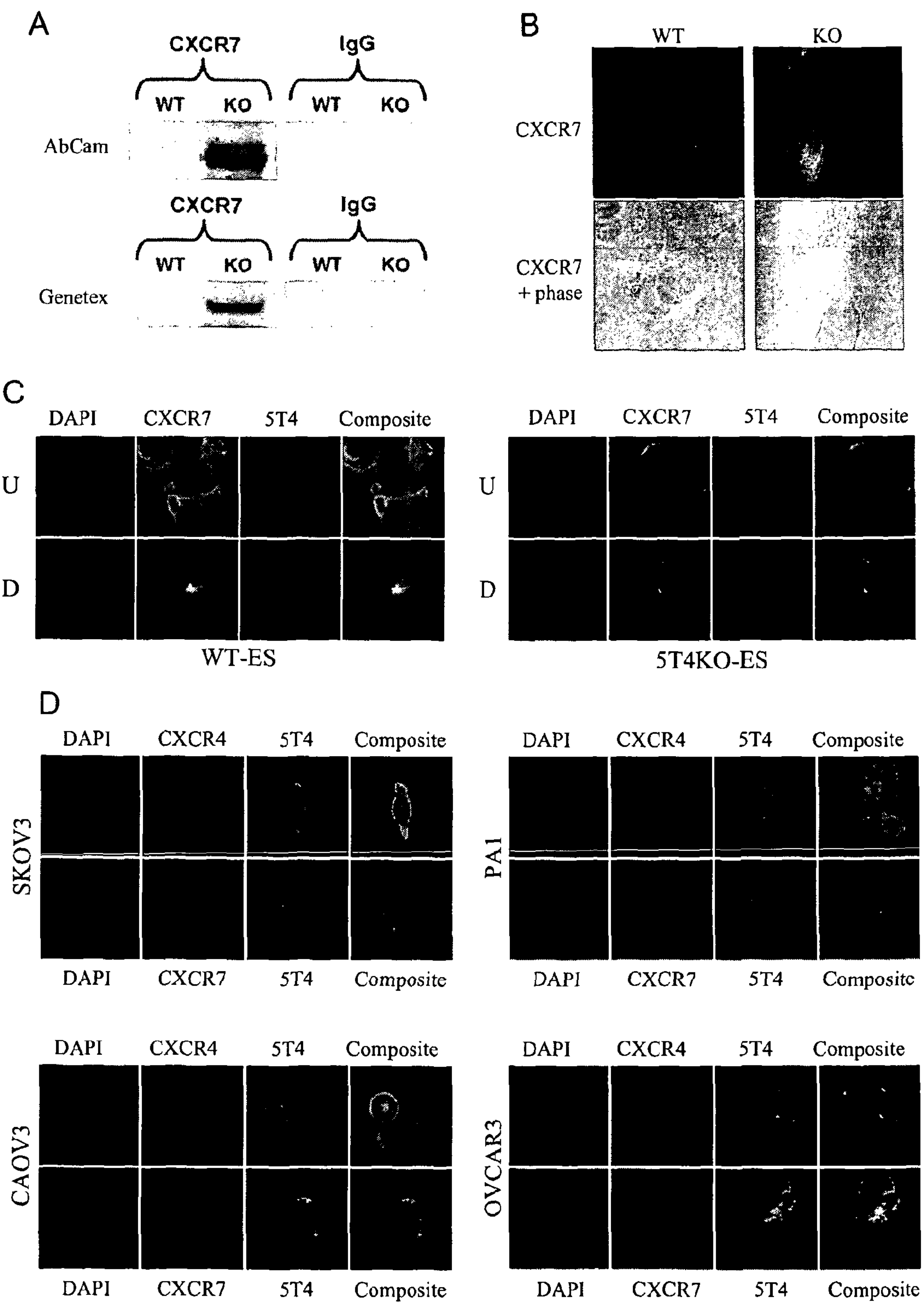

The data FIG. 16 establish that 5T4 is not required for CXCR7 surface expression. Western blot analysis of PAGE separated reduced primary murine embryonic fibroblast membrane lysates probed with CXCR7 antibodies identified a 42 kDa band in 5T4KO but not WT cells. Immunofluorescence detection of CXCR7 showed cell surface expression of CXCR7 evident on KO and not WT fibroblasts. Cell surface expression of CXCR7 is high in undifferentiated ES cells (either WT or 5T4KO). In 3 day differentiating WT-ES cells, CXCR7 is relatively downregulated from the cell surface whereas in differentiating 5T4KO ES surface CXCR7 is retained. The patterns of CXCR4 and CXCR7 cell surface expression appear to be reciprocal in the ovarian cell lines SKOV3, CAOV3, OVCAR3 and PA1; increased CXCR7 correlating with decreased chemotaxis to CXCL12 (see FIG. 10C).

Example 8

Identification of Human and Murine 5T4 Paralogues

Seventeen ESTs have been described for a putative 5T4 paralogue in humans from mixed, brain, eye, pancreas uncharacterized tissue, skin, liver and pineal gland cDNAs. In the mouse twenty ESTs have been discovered in mixed, eye, embryonic tissue, mammary gland, brain, liver, inner ear and uncharacterized tissue.

Furthermore, in the mouse, two mRNA sequences have been isolated from adult male olfactory brain cDNA and 16 days embryo head cDNA. RT-PCR experiments were performed with primers designed outside the transmembrane region of a putative human 5T4 paralogue. A specific product was detected in cDNA generated from the SHSY-5Y neuroblastoma cell line (FIG. 29A. The obtained product was cloned into a plasmid and sequenced. The resulting sequence was aligned using BLAST with the human transcript database and the returned sequence was that of the 5T4 paralogue (see FIG. 29B).

RT-PCR for the constitutive gene EEF2 proved that the cDNA was not contaminated with genomic DNA (see FIG. 29C). These results indicate that the putative 5T4 paralogue is conserved across species and shares a 19/21 amino acid identity with 5T4 within the transmembrane region. Expressed sequence tags (ESTs) of this gene have been identified proving that this area of the genome is transcribed, although reported human ESTs align only with genomic sequences coding for extracellular or intracellular regions of the paralogue. However, by using RT-PCR with primers designed outside the transmembrane region of the putative 5T4 paralogue we detected a specific product in cDNA generated from the SHSY-5Y neuroblastoma cell line to confirm that this area of the gene is transcribed.

FIG. 20 shows that the human paralogue is translated from an alternative initiation site. Both this human protein and the mouse 5T4 paralogue (with N-terminal myc tagging) are expressed at the plasma membrane in transfected HEK 293 cells.

Discussion

In this study, we have demonstrated that 5T4 glycoprotein can play a critical role in the chemotactic behaviour of embryonic and malignant cells in response to the chemokine CXCL12. We first showed that during ES cell differentiation, increased surface expression of 5T4 and CXCL12 production was accompanied by decreased membrane expression of the CXCL12 regulatory protease CD26. Total cell levels of CXCR4 were unchanged. Studies with 5T4 null and WT ES and MEFs established that 5T4 molecules are required for cell surface expression and intracellular signalling of the CXCL12 receptor CXCR4. Importantly, chemotaxis in response to CXCL12 is disrupted in the absence of 5T4. We also showed that 5T4 molecules bind directly and tightly to CXCR4 to facilitate trafficking to and/or retention of the receptor complex at the cell surface. The transmembrane region of 5T4 is critical for binding to CXCR4 and was sufficient in the context of CD44 molecules to allow functional surface CXCR4 expression and chemotaxis after introduction to 5T4 null cells. We studied the effects of cytoskeleton, microtubule and Golgi disruption on the co-localization pattern of 5T4 and CXCR4. Clearly plasma membrane detection of co-localized 5T4/CXCR4 molecules is dependent on microtubules and the molecules are not obligatorily associated at the Golgi. Disruption of the Golgi or the actin cytoskeleton per se does not disrupt all 5T4/CXCR4 co-localization at the plasma membrane. It is not clear whether the membrane interaction of CXCR4 and 5T4 molecules also induces conformational changes in the receptor to govern responsiveness to ligand.

Importantly, the chemotactic response of both differentiated ES cells and MEF can be blocked by some but not all antibodies recognizing distinct parts or epitopes of m5T4 molecules. These data suggest that 5T4 contributes to functional integrity of the CXCR4 receptor expression at the cell surface. Mechanisms could include modulation of 5T4 molecules from the cell surface, and/or allosteric effects on CXCR4 ligand binding and/or direct blocking of ligand binding. It is possible that additional molecules may be a component part of a "functional" complex. Indeed, 5T4 molecules influence aspects of cytoskeletal organization including through the cytoplasmic domain [3-5] and these may be an integrated component of chemotactic response/motility.

The present inventors have considered how 5T4 may interact with CXCR4. The 5T4 gene is highly conserved across different vertebrate species and the TM region is completely conserved (FIG. 17A). This explains why the h5T4 and m5T4 genes could equally restore CXCR4 cell surface expression in 5T4 null cells. Chemokine receptors, G-protein-coupled seven TM spanning proteins, are also highly conserved in evolution [38], with the hydrophobic amino acids of TM domains forming α-helical structures which anchor the receptors in the membrane [39]. Distinct binding sites within the CXCR4 transmembrane domain for CXCL12 and HIV-1 have been described [40] and the receptor can also be functionally regulated by intramembraneous interaction with other molecules [41]. Without wishing to be bound by any theory, the present inventors consider that the 5T4 transmembrane region specifically recognizes intramembrane residues of CXCR4. While the sequence variation across the extracellular chemokine receptor domains may provide for ligand specificity, mechanisms of transmembrane domain interaction with 5T4 molecules may be shared with other receptors in the CXC family such as CXCR6 but not CXCR3 or CXCR7. Interestingly, the LRR-containing protein LRRC4 has been reported to regulate both the expression and signal conduction of the CXCR4 receptor. Introduction of LRRC4 into glioblastoma cells reduced CXCR4 expression, CXCL12-induced ERK and AKT phosphorylation and MMP expression [42]. Crucially, the TM regions of 5T4 and LRRC4 are similar but contain significant differences (FIG. 17B). It is clear that not all CXCL12/CXCR4 responsive cells express 5T4 molecules. 5T4 cannot be an absolute requirement for CXCR4 activation because 5T4 knockout mice are viable, whereas both CXCL12 and CXCR4 KOs are lethal [43, 44]. Clearly there must be some redundancy and other molecules must be able to regulate CXCR4 trafficking to and/or retention at the cell surface. Since we have identified the TM region of 5T4 as the critical domain in CXCR4 regulation, we propose that if other molecules are able to substitute for 5T4 in this process then they are likely to have strikingly similar TM domains. Indeed we have identified a potential paralogue to 5T4 with an almost identical TM domain which is highly conserved across species (see Example 8 and FIGS. 18-29 herein). In particular FIG. 20 presents the data supporting the correct start site of the human 5T4 paralogue protein (PL5) and its TM alignment with the human 5T4 TM is shown in FIG. 17B.

Alternatively there is mounting evidence that chemokine receptors are able to form discrete functional units via heterodimerisation with other G-protein coupled receptors. In the case of CXCR4, heterodimerisation with the chemokine receptor CXCR7, which interestingly binds the same ligand CXCL12, can alter both the kinetics and the dynamics of CXCR4 responsiveness to CXCL12 [64]. It is noteworthy that there is an apparent reciprocity between the expression of 5T4 and CXCR7 in our embryonic tissues however even if CXCR7 does modulate CXCR4 function in these cells it is not sufficient to recover a chemotactic response. It is conceivable however that the functional consequence of CXCR4 activation can be altered by the presence of CXCR7 to promote cell growth/proliferation rather than chemotaxis as a result of changes in the kinetics of CXCR4 signal transduction that could lead to the activation of alternative intracellular signaling pathways.

CXCL12 is a homeostatic chemokine and exceptional angiogenic member of the ELR-CXC sub group and binds to the widely expressed CXCR4 (exclusively) and, as recently reported, the more restricted CXCR7 (also binds CXCL11) [24]. CXCL12 through CXCR4 regulates cardiac and neuronal development, stem cell motility, neovascularisation and tumourigenesis [21]. Besides acting as a cofactor for HIV, CXCR4 mediates the CXCL12-directed migration of cancer cells to metastatic sites through the promotion of angiogenesis and migration of tumour cells in breast, lung, ovarian, renal, prostate and neuroblastoma [20-22]. It is significant that all these tumour types are known to express the 5T4 glycoprotein [2, 9, 45]. Importantly, these CXCR4-positive tumours preferentially spread to tissues with high levels of CXCL12 such as lung, liver, lymph nodes, brain and bone marrow which are key metastatic sites [20-22]. In addition, the stromal environment (often 5T4 positive [2, 7, 8]) can have a tumour-imprinted promotional influence [46]; and chemokines can sometimes induce proliferation rather than chemotaxis enhancing tumourigenesis [24, 47]. In childhood ALL, extramedullary disease is rare at initial diagnosis (<2%) but is observed in a third of the 20% who relapse. High-risk cytogenetic subtypes such as Ph+ ALL not only have a higher relapse rate but also are more likely to relapse in extramedullary sites such as the CNS. This difference in disease patterns suggests that subgroups of leukemic cells with the ability to migrate to extramedullary sites are either more resistant to or protected against chemotherapy and give rise to disease recurrence. A number of tissues and in particular the blood-brain barrier express CXCL12 and ALL express CXCR4 [48]. We show here that a subset of pre-B ALL (≈50% of high risk) patients have high levels of 5T4 transcripts. The Ph+SupB15 and Tom-1 cell lines express 5T4 detectable at the cells surface by FACS or in cytospins and a pilot study of diagnostic material obtained from B-ALL patients in a phase II study showed these assays capable of 5T4 phenotyping biopsies. These results are compatible with the migration of leukemic cells to the CNS and invading across the blood brain barrier giving rise to extramedullary disease. Incidentally, CXCL12 is also critical for the normal development and homeostasis of the CNS [49] and notably 5T4 null mice have defective organization of their adult CNS. A drawback of the management of B-ALL hitherto has been that it has not been possible to identify those B-ALL patients who will develop extramedullary disease, and the outcome for these patients is poor. It is presently believed that 5T4 may be a predictive biomarker of extramedullary relapse and thus for therapeutic failure. Moreover, targeting the interaction of 5T4 with CXCR4 could inhibit the migration/invasion of leukemic cells preventing disease recurrence and improving overall outcome. For some types of B-ALL, the use of 5T4 directed superantigen therapy may be considered [50].

The regulation of CXCR4 surface expression by 5T4 molecules may provide a new way to control response to the chemokine CXCL12 in normal circumstances but could be selected to advantage the spread of a tumour from its primary site. If the latter events are preferentially and constitutively expressed properties of tumours then targeting the CXCR4/5T4 complex might offer new opportunities for therapeutic intervention.

All references cited herein are incorporated herein by reference in their entirety and for all purposes to the same extent as if each individual publication or patent or patent application was specifically and individually indicated to be incorporated by reference in its entirety. The specific embodiments described herein are offered by way of example, not by way of limitation. Any sub-titles herein are included for convenience only, and are not to be construed as limiting the disclosure in any way References 1. Hole, N. & Stern, P. L. A 72 kD trophoblast glycoprotein defined by a monoclonal antibody. *Br J Cancer* 57, 239-46 (1988).
2. Southall, P. J. et al. Immunohistological distribution of 5T4 antigen in normal and malignant tissues. *Br J Cancer* 61, 89-95 (1990).
3. Carsberg, C. J., Myers, K. A., Evans, G. S., Allen, T. D. & Stern, P. L. Metastasis-associated 5T4 oncofoetal antigen is concentrated at microvillus projections of the plasma membrane. *J Cell Sci* 108 (Pt 8), 2905-16 (1995).
4. Carsberg, C. J., Myers, K. A. & Stern, P. L. Metastasis-associated 5T4 antigen disrupts cell-cell contacts and induces cellular motility in epithelial cells. *Int J Cancer* 68, 84-92 (1996).
5. Awan, A. et al. 5T4 interacts with TIP-2/GIPC, a PDZ protein, with implications for metastasis. *Biochem Biophys Res Commun* 290, 1030-6 (2002).
6. Mulder, W. M. et al. Low intercellular adhesion molecule 1 and high 5T4 expression on tumor cells correlate with reduced disease-free survival in colorectal carcinoma patients. *Clin Cancer Res* 3, 1923-30 (1997).

7. Starzynska, T. et al. Prognostic significance of 5T4 oncofetal antigen expression in colorectal carcinoma. *Br J Cancer* 69, 899-902 (1994).

8. Starzynska, T. et al. 5T4 oncofetal antigen in gastric carcinoma and its clinical significance. *Eur J Gastroenterol Hepatol* 10, 479-84 (1998).

9. Wrigley, E. et al. 5T4 oncofetal antigen expression in ovarian carcinoma. *Int J Gynecol Cancer* 5, 269-274 (1995).

10. King, K. W., Sheppard, F. C., Westwater, C., Stern, P. L. & Myers, K. A. Organisation of the mouse and human 5T4 oncofoetal leucine-rich glycoprotein genes and expression in foetal and adult murine tissues. *Biochim Biophys Acta* 1445, 257-70 (1999).

11. Myers, K. A. et al. Isolation of a cDNA encoding 5T4 oncofetal trophoblast glycoprotein. An antigen associated with metastasis contains leucine-rich repeats. *J Biol Chem* 269, 9319-24 (1994).

12. Kobe, B. & Kajava, A. V. The leucine-rich repeat as a protein recognition motif. *Current Opinion in Structural Biology* 11, 725-732 (2001).

13. Ward, C. M., Barrow, K., Woods, A. M. & Stern, P. L. The 5T4 oncofoetal antigen is an early differentiation marker of mouse ES cells and its absence is a useful means to assess pluripotency. *J Cell Sci* 116, 4533-42 (2003).

14. Ward, C. M., Eastham, A. M. & Stern, P. L. Cell surface 5T4 antigen is transiently upregulated during early human embryonic stem cell differentiation: effect of 5T4 phenotype on neural lineage formation. *Exp Cell Res* 312, 1713-26 (2006).

15. Eastham, A. M. et al. Epithelial-mesenchymal transition events during human embryonic stem cell differentiation. *Cancer Res* 67, 11254-62 (2007).

16. Spencer, H. L. et al. E-cadherin inhibits cell surface localization of the pro-migratory 5T4 oncofetal antigen in mouse embryonic stem cells. *Mol Biol Cell* 18, 2838-51 (2007).

17. Cavallaro, U. & Christofori, G. Cell adhesion and signalling by cadherins and Ig-CAMs in cancer. *Nat Rev Cancer* 4, 118-32 (2004).

18. Guarino, M. Epithelial-mesenchymal transition and tumor invasion. *Int J Biochem Cell Biol* 39, 2153-60 (2007).

19. Christopherson, K. W., 2nd, Hangoc, G., Mantel, C. R. & Broxmeyer, H. E. Modulation of hematopoietic stem cell homing and engraftment by CD26. *Science* 305, 1000-3 (2004).

20. Balkwill, F. The significance of cancer cell expression of the chemokine receptor CXCR4. *Semin Cancer Biol* 14, 171-9 (2004).

21. Vandercappellen, J., Van Damme, J. & Struyf, S. The role of CXC chemokines and their receptors in cancer. *Cancer Lett* 267, 226-44 (2008).

22. Burger, J. A. & Kipps, T. J. CXCR4: a key receptor in the crosstalk between tumor cells and their microenvironment. Blood 107, 1761-7 (2006).

23. Nagasawa, T. et al. Molecular cloning and characterization of a murine pre-B-cell growth-stimulating factor/stromal cell-derived factor 1 receptor, a murine homolog of the human immunodeficiency virus 1 entry coreceptor fusin. *Proc Natl Acad Sci USA* 93, 14726-9 (1996).

24. Burns, J. M. et al. A novel chemokine receptor for SDF-1 and I-TAC involved in cell survival, cell adhesion, and tumor development. *J Exp Pled* 203, 2201-13 (2006).

25. Ganju, R. K. et al. The alpha-chemokine, stromal cell-derived factor-1alpha, binds to the transmembrane G-protein-coupled CXCR-4 receptor and activates multiple signal transduction pathways. *J Biol Chem* 273, 23169-75 (1998).

26. Zhang, J., Sarkar, S. & Yong, V. W. The chemokine stromal cell derived factor-1 (CXCL12) promotes glioma invasiveness through MT2-matrix metalloproteinase. *Carcinogenesis* 26, 2069-77 (2005).

27. Woods, A. M. et al. Characterization of the murine 5T4 oncofoetal antigen: a target for immunotherapy in cancer. *Biochem J* 366, 353-65 (2002).

28. Xu, J. Preparation, culture, and immortalization of mouse embryonic fibroblasts. *Curr Protoc Mol Biol* Chapter 28, Unit 28 1 (2005).

29. Hooper, M., Hardy, K., Handyside, A., Hunter, S. & Monk, M. HPRT-deficient (Lesch-Nyhan) mouse embryos derived from germline colonization by cultured cells. *Nature* 326, 292-5 (1987).

30. Smethurst, G. University of Manchester (2006).

31. Southgate, T. D., Kingston, P. A. & Castro, M. G. Gene transfer into neural cells in vitro using adenoviral vectors. *Curr Protoc Neurosci* Chapter 4, Unit 4 23 (2001).

32. Hildinger, M. et al. FMEV vectors: both retroviral long terminal repeat and leader are important for high expression in transduced hematopoietic cells. *Gene Ther* 5, 1575-9 (1998).

33. Naor, D., Wallach-Dayan, S. B., Zahalka, M. A. & Sionov, R. V. Involvement of CD44, a molecule with a thousand faces, in cancer dissemination. *Semin Cancer Biol* 18, 260-7 (2008).

34. Hardy, S., Kitamura, M., Harris-Stansil, T., Dai, Y. & Phipps, M. L. Construction of adenovirus vectors through Cre-lox recombination. *J Virol* 71, 1842-9 (1997).

35. Strefford, J. C. et al. Complex genomic alterations and gene expression in acute lymphoblastic leukemia with intrachromosomal amplification of chromosome 21. *Proc Natl Acad Sci USA* 103, 8167-72 (2006).

36. van Delft, F. W. et al. Prospective gene expression analysis accurately subtypes acute leukaemia in children and establishes a commonality between hyperdiploidy and t(12; 21) in acute lymphoblastic leukaemia. *Br J Haematol* 130, 26-35 (2005).

37. Sipkins, D. A. et al. In vivo imaging of specialized bone marrow endothelial microdomains for tumor engraftment. *Nature* 435, 969-73 (2005).

38. DeVries, M. E. et al. Defining the origins and evolution of the chemokine/chemokine receptor system. *J Immunol* 176, 401-15 (2006).

39. Strader, C. D., Fong, T. M., Graziano, M. P. & Tota, M. R. The family of G-protein-coupled receptors. *Faseb J* 9, 745-54 (1995).

40. Tian, S. et al. Distinct functional sites for human immunodeficiency virus type 1 and stromal cell-derived factor 1alpha on CXCR4 transmembrane helical domains. *J Virol* 79, 12667-73 (2005).

41. Pello, O. M. et al. Ligand stabilization of CXCR4/delta-opioid receptor heterodimers reveals a mechanism for immune response regulation. *Eur J Immunol* 38, 537-49 (2008).

42. Wu, M. et al. LRRC4 inhibits human glioblastoma cells proliferation, invasion, and proMMP-2 activation by reducing SDF-1 alpha/CXCR4-mediated ERK1/2 and Akt signaling pathways. *J Cell Biochem* 103, 245-55 (2008).

43. Ma, Q. et al. Impaired B-lymphopoiesis, myelopoiesis, and derailed cerebellar neuron migration in CXCR4- and SDF-1-deficient mice. *Proc Natl Acad Sci USA* 95, 9448-53 (1998).

44. Zou, Y. R., Kottmann, A. H., Kuroda, M., Taniuchi, I. & Littman, D. R. Function of the chemokine receptor CXCR4 in haematopoiesis and in cerebellar development. *Nature* 393, 595-9 (1998).
45. Griffiths, R. W. et al. Expression of the 5T4 oncofoetal antigen in renal cell carcinoma: a potential target for T-cell-based immunotherapy. *Br J Cancer* 93, 670-7 (2005).
46. Orimo, A. et al. Stromal fibroblasts present in invasive human breast carcinomas promote tumor growth and angiogenesis through elevated SDF-1/CXCL12 secretion. *Cell* 121, 335-48 (2005).
47. Thelen, M. & Thelen, S. CXCR7, CXCR4 and CXCL12: An eccentric trio? *J Neuroimmunol* 198, 9-13 (2008).
48. Bradstock, K. F. et al. Effects of the chemokine stromal cell-derived factor-1 on the migration and localization of precursor-B acute lymphoblastic leukemia cells within bone marrow stromal layers. *Leukemia* 14, 882-8 (2000).
49. Li, M. & Ransohoff, R. M. Multiple roles of chemokine CXCL12 in the central nervous system: a migration from immunology to neurobiology. *Prog Neurobiol* 84, 116-31 (2008).
50. Shaw, D. M. et al. A phase II study of a 5T4 oncofoetal antigen tumor-targeted superantigen (ABR-214936) therapy in patients with advanced renal cell carcinoma. *Br J Cancer* 96, 567-74 (2007).
51. Hu, W. et al. CXCR6 is expressed in human prostate cancer in vivo and is involved in the in vitro invasion of PC3 and LNCap cells. *Cancer Sci.* 99(7), 1362-9, (2008).
52. Xu, Y. et al. Evaluation of "credit card" libraries for inhibition of HIV-1 gp41 fusogenic core formation. *J. Comb. Chem.* 8(4), 531-9, (2006).
53. Forsberg, G. et al. Therapy of human non-small-cell lung carcinoma using antibody targeting of a modified superantigen. *British Journal of Cancer.* 85(1), 129-136, (2001).
54. Barbieri, F. et al. Overexpression of stromal cell-derived factor 1 and its receptor CXCR4 induces autocrine/paracrine cell proliferation in human pituitary adenomas. *Clin Cancer Res* 14(16), 5022-32, (2008).
55. Hernández-López, C. et al. CXCL12/CXCR4 signaling promotes human thymic dendritic cell survival regulating the Bcl-2/Bax ratio. *Immunol Lett* 120(1-2), 72-8, (2008).
56. Nanki, T. et al. Pathogenic role of the CXCL16-CXCR6 pathway in rheumatoid arthritis. *Arthritis Rheum* 52(10), 3004-14, (2005).
57. Lukacs, N. W. et al. AMD3100, a CXCR4 antagonist, attenuates allergic lung inflammation and airway hyperreactivity. *Am J Pathol* 160(4), 1353-60, (2002).
58. Aslanian, A. M. and Charo, I. F. Targeted disruption of the scavenger receptor and chemokine CXCL16 accelerates atherosclerosis. *Circulation* 114(6), 583-90, (2006).
59. Mikami, S. et al. Bloackade of CXCL12/CXCR4 axis ameliorates murine experimental colitis. *J Pharmacol Exp Ther* [Epub ahead of print] (2008).
60. Heydtmann, M. et al. CXC chemokine ligand 16 promotes integrin-mediated adhesion of liver-infiltrating lymphocytes to cholangiocytes and hepatocytes within the inflamed human liver. *J Immunol* 174(2), 1055-62, (2005).
61. Wragg, A. et al. VEGFR1/CXCR4-positive progenitor cells modulate local inflammation and augment tissue perfusion by a SDF-1-dependent mechanism. *J Mol Med* [Epub ahead of print] (2008).
62. Juremalm, M. et al. The chemokine receptor CXCR4 is expressed within the mast cell lineage and its ligand stromal cell-derived factor-1 acts as a mast cell chemotaxin. *Eur J Immunol* 30(12), 3614-22, (2000).
63. Hu, J. S. et al. AMD3465, a novel CXCR4 receptor antagonist abrogates schistosomal antigen-elicited (type-2) pulmonary granuloma formation. *Am J Pathol* 169(2), 424-32, (2006).
64. Sierro F et al. Disrupted cardiac development but normal hematopoiesis in mice deficient in the second CXCL12/SDF-1 receptor, CXCR7. *Proc Natl Acad Sci USA.* 104 (37), 14759-64 (2007).

The invention claimed is:

1. A method for identifying a chemotaxis inhibitor, comprising:

(a) providing a 5T4 polypeptide comprising at least a 5T4 transmembrane domain, a CXC chemokine receptor polypeptide, which is selected from a CXCR4 polypeptide or a CXCR6 polypeptide, and a test agent under conditions in which, in the absence of the test agent, the 5T4 polypeptide and the CXC chemokine receptor polypeptide are able to interact; and (b) determining whether the test agent inhibits the interaction between 5T4 polypeptide and the CXC chemokine receptor polypeptide;

wherein inhibition of said interaction indicates that said test agent is a chemotaxis inhibitor.

2. The method according to claim 1, wherein determining whether the test agent inhibits said interaction comprises detecting a complex comprising the 5T4 polypeptide and the CXC chemokine receptor polypeptide, and wherein a decrease in the level of said complex and/or a decrease in the formation of said complex in the presence of the test agent, as compared with in the absence of the test agent, indicates that the test agent is a chemotaxis inhibitor.

3. The method according to claim 1, wherein the 5T4 polypeptide and the CXC chemokine receptor polypeptide are expressed by a cell and the cell is contacted with the test agent.

4. The method according to claim 3, wherein determining whether the test agent inhibits said interaction comprises detecting cell surface expression of the CXC chemokine receptor polypeptide and/or a complex comprising the CXC chemokine receptor polypeptide, and wherein a decrease in the cell surface expression of the CXC chemokine receptor polypeptide and/or said complex in the presence of the test agent, as compared with in the absence of the test agent, indicates that the test agent is a chemotaxis inhibitor.

5. The method according to claim 3, further comprising assessing CXC chemokine receptor polypeptide-mediated chemotaxis of the cell in the presence of the test agent, as compared with in the absence of the test agent.

6. The method according to claim 3, further comprising assessing CXC chemokine receptor polypeptide-mediated cell proliferation and/or cell survival in the presence of the test agent, as compared with in the absence of the test agent.

7. The method according to claim 3, wherein the cell is a cancer cell.

8. The method according to claim 7, further comprising an in vivo step of assessing metastasis of a cancer in a non-human animal model to which the test agent has been administered, as compared with metastasis of a cancer in a control non-human animal model to which the test agent has not been administered.

9. The method according to claim 8, wherein said non-human animal model is a 5T4 null rodent having an implanted 5T4-positive and CXC chemokine receptor-positive tumour.

10. The method according to claim 1, wherein the 5T4 polypeptide further comprises at least one of a 5T4 extracellular domain and a 5T4 cytoplasmic domain.

11. The method according to claim 1, wherein the CXC chemokine receptor polypeptide comprises a CXC chemokine receptor subfamily member other than CXCR3 and CXCR7.

12. The method according to claim 1, where the test agent comprises an agent selected from:

(a) an antibody or fragment thereof capable of binding the 5T4 polypeptide;

(b) an antibody or fragment thereof capable of binding the CXC chemokine receptor polypeptide;

(c) an antibody or fragment thereof capable of binding to both the 5T4 polypeptide and the CXC chemokine receptor polypeptide; and (d) an antibody or fragment thereof which selectively binds a complex which comprises the 5T4 polypeptide and the CXC chemokine receptor polypeptide.

13. The method according to claim 12, wherein the 5T4 polypeptide comprises an extracellular domain and wherein the test agent comprises an antibody or fragment thereof that binds the extracellular domain of the 5T4 polypeptide.

14. The method according to claim 1, wherein the test agent is found to inhibit the interaction between 5T4 polypeptide and the CXC chemokine receptor polypeptide.

15. The method according to claim 1, wherein the CXC chemokine receptor polypeptide comprises a CXCR4 polypeptide or a CXCR6 polypeptide.

* * * * *

UNITED STATES PATENT AND TRADEMARK OFFICE

CERTIFICATE OF CORRECTION

PATENT NO. : 8,715,947 B2
APPLICATION NO. : 13/502893
DATED : May 6, 2014
INVENTOR(S) : Stern et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 34 days.

Signed and Sealed this
Twenty-ninth Day of September, 2015

Michelle K. Lee

Michelle K. Lee
*Director of the United States Patent and Trademark Office*